US008629168B2

(12) United States Patent
Gerspacher et al.

(10) Patent No.: US 8,629,168 B2
(45) Date of Patent: Jan. 14, 2014

(54) BENZOXAZOLES AND OXAZOLOPYRIDINES BEING USEFUL AS JANUS KINASES INHIBITORS

(76) Inventors: Marc Gerspacher, Basel (CH); Pascal Furet, Basel (CH); Eric Vangrevelinghe, Basel (CH)

( * ) Notice: Subject to any disclaimer, the term of this patent is extended or adjusted under 35 U.S.C. 154(b) by 813 days.

(21) Appl. No.: 12/440,298

(22) PCT Filed: Sep. 13, 2007

(86) PCT No.: PCT/EP2007/007983
§ 371 (c)(1), (2), (4) Date: Mar. 6, 2009

(87) PCT Pub. No.: WO2008/031594
PCT Pub. Date: Mar. 20, 2008

(65) Prior Publication Data

US 2010/0009978 A1 Jan. 14, 2010

(30) Foreign Application Priority Data

Sep. 15, 2006 (EP) .................................... 06120733

(51) Int. Cl.

| | |
|---|---|
| ***C07D 263/58*** | (2006.01) |
| ***C07D 263/60*** | (2006.01) |
| ***C07D 413/00*** | (2006.01) |
| ***C07D 498/00*** | (2006.01) |
| ***A01N 43/76*** | (2006.01) |
| ***A61K 31/42*** | (2006.01) |

(52) U.S. Cl.
USPC ............ 514/377; 548/222; 514/374; 514/375

(58) Field of Classification Search
None
See application file for complete search history.

(56) References Cited

FOREIGN PATENT DOCUMENTS

| | | | |
|---|---|---|---|
| WO | WO 2004/099204 | A1 | 11/2004 |
| WO | 2005/037829 | A1 | 4/2005 |
| WO | WO 2007/025897 | A2 | 3/2007 |

OTHER PUBLICATIONS

Silverman, The Organic Chemistry of Drug Design and Drug Action, 2nd ed., 2004, pp. 25-34.*
Kawai et al. "Structure-activity relationship study of novel NR2B-selective antagonists with arylamides to avoid reactive metabolites formation", Bioorg.Med.Chem.Lett., 2007, vol. 17, pp. 5537-5542.*
Sandberg et al. "Jak2 Tyrosine Kinase: A True Jak of All Trades?", CellBiochem.Biophys., 2004, vol. 41, pp. 207-231.*
Silverman, The Organic Chemistry of Drug Design and Drug Action, 2nd ed., 2004, pp. 25-51.*
Patani et al. "Bioisosterism: A Rational Approach in Drug Design", Chem.Rev., 1996, vol. 96, pp. 3147-3176.*
Neidle, Cancer Drug Design and Discovery, Elsevier/Academic Press, 2008, pp. 427-431.*

* cited by examiner

*Primary Examiner* — James D Anderson
*Assistant Examiner* — Stephanie Springer
(74) *Attorney, Agent, or Firm* — Laura Madden; Novartis Institutes for Biomedical Research, Inc.

(57) ABSTRACT

The invention relates to 2,7-disubstituted benzoxazole and 2,4-disubstituted oxazolo[5,4-c]pyridine compounds of the formula I given below, as well as salts thereof, processes for the preparation thereof, the application thereof in a process for the treatment of the human or animal body, these compounds for use in the treatment (including prophylaxis) of the animal, especially human, body (especially with regard to a proliferative disease), the use thereof—alone or in combination with one or more other pharmaceutically active compounds—for the treatment especially of a protein tyrosine kinase mediated disease (such as a tumor disease) or for the manufacture of a pharmaceutical preparation for use in the treatment of such a disease, a method for the treatment of such a disease and a pharmaceutical preparation for the treatment of a disease as mentioned. The compounds are of the formula I, (I)

$R^1$, N, H, N, O, $R^4$, $R^3$, X, $R^2$ wherein the symbols are as defined in the description. The compounds inhibit, for example, JAK2 and JAK3.

11 Claims, No Drawings

BENZOXAZOLES AND OXAZOLOPYRIDINES BEING USEFUL AS JANUS KINASES INHIBITORS

This application is a U.S. National Phase filing of International Serial No. PCT/EP2007/007983 filed Sep. 13, 2007, and claims priority to EP Application Serial No. 06120733.8 filed Sep. 15, 2006, the content of which are incorporated herein by reference in their entirety.

The invention relates to 2,7-disubstituted benzoxazole and 2,4-disubstituted-oxazolo[5,4-c]pyridine compounds of the formula I given below, as well as salts thereof, processes for the preparation thereof, the application thereof in a process for the treatment of the human or animal body, these compounds for use in the treatment (including prophylaxis) of the animal, especially human, body (especially with regard to a proliferative disease), the use thereof—alone or in combination with one or more other pharmaceutically active compounds—for the treatment especially of a protein tyrosine kinase mediated disease (such as a tumor disease) or for the manufacture of a pharmaceutical preparation for use in the treatment of such a disease, a method for the treatment of such a disease and a pharmaceutical preparation for the treatment of a disease as mentioned.

Janus kinases (JAKs) form a family of intracellular protein tyrosine kinases with four members, JAK1, JAK2, JAK3 and TYK2. These kinases are important in the mediation of cytokine receptor signaling which induces various biological responses including cell proliferation, differentiation and apoptosis. Knock-out experiments in mice have shown that JAKs are inter alia important in hematopoiesis. In addition, JAK2 was shown to be implicated in myeloproliferative diseases and cancers. JAK2 activation by chromosome re-arrangements and/or loss of negative JAK/STAT (STAT=signal transducing and activating factor(s)) pathway regulators has been observed in hematological malignancies as well as in certain solid tumors.

It has now been found that the 2,7-substituted benzoxazole and 2,4-disubstituted-oxazolo[5,4-c]pyridine compounds of the formula I, described below, have advantageous pharmacological properties and inhibit, for example, the tyrosine kinase activity of Janus kinases, such as JAK2 kinase and/or JAK3-(but also JAK-1-) kinase. Hence, the compounds of formula I are suitable, for example, to be used in the treatment of diseases depending on the tyrosine kinase activity of JAK2 (and/or JAK3) kinase, especially proliferative diseases such as tumor diseases, leukaemias, polycythemia vera, essential thrombocythemia, and myelofibrosis with myeloid metaplasia. Through the inhibition of JAK-3 kinase, compounds of the invention also have utility as immunosuppressive agents, for example for the treatment of diseases such as organ transplant rejection, lupus erythematodes, multiple sclerosis, rheumatoid arthritis, psoriasis, dermatitis, Crohn's disease, type-1 diabetes and complications from type-1 diabetes.

The invention relates to compounds of the formula I, (I)

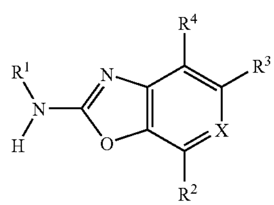

wherein

X is N or $CR^5$, wherein $R^5$ is halo, cyano, hydroxyl, $C_1$-$C_7$-alkoxy, $C_1$-$C_7$-alkyl, amino, N-mono- or N,N-di-$C_1$-$C_7$-alkyl or preferably hydrogen;

$R^1$ is unsubstituted or substituted aryl or is unsubstituted or substituted heterocyclyl; and $R^2$ is unsubstituted or substituted aryl or is unsubstituted or substituted heterocyclyl which is bound via a ring carbon atom (to the carbon at position 7 of the benzoxazole ring in formula I or (if X is N) to the carbon at position 4 in the oxazolopyridine ring of formula I);

$R^3$ is cyano, hydroxyl, $C_1$-$C_7$-alkyl, amino, N-mono- or N,N-di-$C_1$-$C_7$-alkyl or preferably hydrogen; and $R^4$ is hydroxyl, amino or preferably hydrogen;

or salts thereof.

Preferably, the invention relates to a compound of the formula I wherein

X is $CR^5$ or N, wherein $R^5$ is halo, cyano, hydroxyl, $C_1$-$C_7$-alkoxy, $C_1$-$C_7$-alkyl, amino, N-mono- or N,N-di-$C_1$-$C_7$-alkyl or preferably hydrogen;

$R^1$ is unsubstituted or substituted aryl or is unsubstituted or substituted heterocyclyl, especially $R^1$ is phenyl, naphthyl, indanyl, pyridyl, oxo-1H-pyridyl, indolyl, dihydroindolyl or oxo-dihydroindolyl, each of which is bound via a ring carbon atom and is unsubstituted or substituted by one to three moieties independently selected from the group consisting of $C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidine oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, cyano and nitro, $R^2$ is phenyl, naphthyl, indanyl, pyridyl, oxo-1H-pyridyl, pyrazolyl, thiophenyl, indolyl, dihydroindolyl, oxo-dihydroindolyl, quinolinyl, isoquinolinyl or 1H-benzoimidazolyl, each of which is bound via a ring carbon atom and is unsubstituted or substituted by one to three moieties independently selected from the group consisting of $C_1$-$C_7$-alkyl, hydroxyl-$C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, $C_1$-$C_7$-alkanesulfonyl-$C_1$-$C_7$-alkyl, $C_1$-$C_7$-alkanesulfinyl-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, 4-($C_1$-$C_7$-alkanoyl)-piperazin-1-yl-$C_1$-$C_7$-alkyl, oxo-piperazin-1-yl-$C_1$-$C_7$-alkyl, pyrrolidin-1-carbonyl-$C_1$-$C_7$-alkyl, piperidin-1-carbonyl-$C_1$-$C_7$-alkyl, piperazin-1-carbonyl-$C_1$-$C_7$-alkyl, 4-($C_1$-$C_7$-alkyl)piperazin-1-carbonyl-$C_1$-$C_7$-alkyl, morpholin-1-carbonyl-$C_1$-$C_7$-alkyl, thiomorpholin-1-carbonyl-$C_1$-$C_7$-alkyl, S-oxo- or S,S-dioxothiomorpholin-1-carbonyl-$C_1$-$C_7$-alkyl, $C_1$-$C_7$-alkoxy-$C_1$-$C_7$-alkyl, halo-$C_1$-$C_7$-alkyl, $C_1$-$C_7$-alkanoyl or $C_3$-$C_{10}$-cycloalkyl)-oxo-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, imidazol-1-yl-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidine, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkane-sulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, S-oxo-thiomorpholinosulfonyl, S,S-dioxothiomorpholinosulfonyl, cyano and nitro, preferably in the meta, (more preferably once) in the meta (preferably up to once) and the para or in the para position $R^3$ is cyano, hydroxyl, $C_1$-$C_7$-alkyl, amino, N-mono- or N,N-di-$C_1$-$C_7$-alkyl or preferably hydrogen; and $R^4$ is hydroxyl, amino or preferably hydrogen;

or a pharmaceutically acceptable salt thereof.

Also preferably, the invention relates to a compound of the formula I wherein

X is $CR^5$ or N, wherein $R^5$ is halo, cyano, hydroxyl, $C_1$-$C_7$-alkoxy, $C_1$-$C_7$-alkyl, amino, N-mono- or N,N-di-$C_1$-$C_7$-alkyl or preferably hydrogen;

$R^1$ is unsubstituted or substituted aryl or is unsubstituted or substituted heterocyclyl, $R^2$ is phenyl, naphthyl, pyridyl, pyrazolyl, thiophenyl, quinolinyl, isoquinolinyl or 1H-benzo-imidazolyl, each of which is bound via a ring carbon atom and is unsubstituted or substituted by one to three moieties independently selected from the group consisting of $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, $C_1$-$C_7$-alkane-sulfonylamino, carbamoyl, N-mono- or N,N-di-($C_1$-$C_7$-alkyl)-carbamoyl, sulfo, $C_1$-$C_7$-alkane-sulfonyl, sulfamoyl, N-mono- or N,N-di-($C_1$-$C_7$-alkyl)-sulfamoyl, morpholinosulfonyl, thiomorpholinosulfonyl, cyano and nitro, preferably in the meta, (more preferably once) in the meta (preferably up to once) and the para or in the para position $R^3$ is cyano, hydroxyl, $C_1$-$C_7$-alkyl, amino, N-mono- or N,N-di-$C_1$-$C_7$-alkyl or preferably hydrogen; and $R^4$ is hydroxyl, amino or preferably hydrogen;

or a pharmaceutically acceptable salt thereof.

More preferably, the invention relates to a compound of the formula I wherein

X is $CR^5$ or N, wherein $R^5$ is halo, cyano, hydroxyl, $C_1$-$C_7$-alkoxy, $C_1$-$C_7$-alkyl, amino, N-mono- or N,N-di-$C_1$-$C_7$-alkyl or preferably hydrogen;

$R^1$ is unsubstituted or substituted aryl or is unsubstituted or substituted heterocyclyl, $R^2$ is phenyl, naphthyl, pyridyl, pyrazolyl, thiophenyl, quinolinyl, isoquinolinyl or 1H-benzo-imidazolyl, each of which is bound via a ring carbon atom and is unsubstituted or substituted by one to three moieties independently selected from the group consisting of $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, $C_1$-$C_7$-alkanesulfonylamino, carbamoyl, N-mono- or N,N-di-($C_1$-$C_7$-alkyl)-carbamoyl, sulfo, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, cyano and nitro, $R^3$ is cyano, hydroxyl, $C_1$-$C_7$-alkyl, amino, N-mono- or N,N-di-$C_1$-$C_7$-alkyl or preferably hydrogen; and $R^4$ is hydroxyl, amino or preferably hydrogen;

or a pharmaceutically acceptable salt thereof.

The invention relates very especially to a compound of the formula I, wherein

X is CH or N;

$R^1$ is phenyl, (especially 3,4,5-)trimethoxyphenyl*, (especially 3,4- or 3,5-)dimethoxyphenyl*, (especially 4-)morpholinophenyl, (especially 4-) N-(2-methoxyethyl)-carbamoylphenyl*, or (especially 4-)N,N-(2-dimethylamino-ethyl)-carbamoylphenyl*, (especially 4-)dimethylamino-carbonyl-(especially 3-)methyl-phenyl*, (especially 4-)-(preferably 4-)-(2-methoxy-ethyl-piperazin-(especially 1-)yl-(especially 3-)-methyl-phenyl, (especially 4-)pyrrolidin-1-carbonyl-(especially 3-)methyl-phenyl*, (especially 3-)methyl-(especially 4-)-4-methylpiperazin-1-carbonyl-phenyl, (especially 3- or 4-)4-methyl-piperazin-1-yl-phenyl*, (especially 4-)-4-ethyl-piperazin-1-yl-(especially 3-)methyl-phenyl*, (especially 4-)-4-methyl-piperazin-1-yl-(especially 3-)cyano-phenyl, (especially 4-)-piperazin-1-yl-phenyl, (especially 4-)-4-cyclopropyl-piperazin-1-yl-phenyl, (especially 4-)-4-(2-dimethylaminoethyl)-piperazin-1-yl-(especially 3-)methyl-phenyl*, (especially 4-)4-isopropyl-piperazin-1-yl)-(especially 3-)methyl-phenyl*, (especially 4-)N,N-diethylaminocarbonyl-(especially 3-)methyl-phenyl*, (especially 4-)4-ethylpiperazin-1-carbonyl-(especially 3-)methyl-phenyl, (especially 4-)-(4-ethylpiperazin-1-ylmethyl)-(especially 3-)methyl-phenyl, (especially 4-)N-methylaminocarbonyl-(especially 3-)methylphenyl, (especially 4-)-4-(3,3,3-trifluoropropyl)-piperazin-1-yl-(especially 3-)methyl-phenyl, (especially 4-)-4-(2-(N',N'-dimethylamino)ethyl-aminocarbonyl-(especially 3-)methyl-phenyl, (especially 4-)-methanesulfonyl-phenyl*, (especially 4-)[(especially 2-)-oxo-pyrrolidin-1-yl]-phenyl, (especially 4-)N,N-diethylaminocarbonyl-(especially 3-)methoxyphenyl, (especially 3-)-4-methylpiperazin-1-yl-(especially 4-)methyl-phenyl, (especially 3-)-4-methylpiperazin-1-yl-(especially 4-)methoxy-phenyl*, (especially 3- or 4-)-morpholinomethyl-(especially 4- or 3-)methyl-phenyl, (especially 2-)acetylamino-indan-(especially 5-)yl, (especially 2-)oxo-2,3-dihydroindol-(especially 5-)yl, (especially 4-)methylsulfinylphenyl, (especially 4-)methoxyphenyl, (especially 4-)methyl-(especially 3-)methoxyphenyl, (especially 4-)-N-(2-methoxyethyl)-aminocarbonyl-phenyl, (especially 4-)N,N-dimethylcarbamoyl-phenyl, (especially 3-)methanesulfonylamino-phenyl, (especially 4-)methoxy-carbonyl-(especially 3-)methoxy-phenyl, (especially 4-)N,N-dimethylcarbamoyl-(especially 3-)methoxy-phenyl, (especially 4-)-(4-cyclopropyl-piperazin-1-yl)-(especially 3-)methyl-phenyl*, (especially 4-)-N-(2-(N',N'-dimethylaminoethyl)-N-methyl-carbamoyl-(especially 3-)methyl-phenyl*, 1,3-dimethyl-oxo-1H-pyridine-5-yl, (especially 3- or 4-)morpholino-(especially 4- or 3-)methyl-phenyl*, (especially 4-)morpholinomethyl-(especially 3-)methyl-phenyl, (especially 4-)morpholin-1-carbonyl-(especially 3-)methyl-phenyl, (especially 4-)-N-2-(methoxyethyl)aminocarbonyl-(especially 3-)methyl-phenyl, (especially 4-)-N-(3-N',N'-dimethylaminopropyl)amino-carbonyl-(especially 3-)methyl-phenyl, (especially 5-)-methyl-(especially 6-)methoxy-pyridin-3-yl, (especially 4-)dimethylcarbamoyl-(especially 3,5-)dimethyl-phenyl, (especially 4-)dimethyl-carbamoyl-(especially 3-)ethyl-phenyl, (especially 4-(4-)N,N-dimethylcarbamoyl-(especially 3-)methyl-phenyl or (especially 4-)morpholino-(especially 3-)cyano-phenyl;

$R^2$ is phenyl, (especially 4-)methylphenyl, (especially 3-)methylphenyl, (especially 2-)methylphenyl, (especially 4-)-hydroxymethyl-phenyl, (especially 4-)aminomethyl-phenyl, (especially 3-)aminomethyl-phenyl, (especially 4-)acetylaminomethyl-phenyl*, (especially 4-)methanesulfonylaminomethyl-phenyl, (especially 3-)acetylaminomethyl-phenyl, (especially 3-)methanesulfonylaminomethyl-phenyl*, (especially 4-)methanesulfonylaminomethyl-phenyl, (especially 4-)(N-methylcarbamoyl)-methylphenyl*, (especially 4-)methanesulfinylmethyl-phenyl, (especially 4-)methanesulfonylmethylphenyl, (especially 3-)chlorophenyl, (especially 3-)hydroxyphenyl, (especially 4-)methoxyphenyl, (especially 3-)methoxyphenyl*, (especially 2-)methoxyphenyl, (especially 4-)aminophenyl, (especially 3-)aminophenyl, (especially 2-)aminophenyl, (especially 3-)N-methylamino-phenyl, (especially 4-)N,N-dimethylamino-phenyl*, (especially 4-)acetylamino-phenyl, (especially 3-)acetylamino-phenyl, (especially 4-)methanesulfonylamino-phenyl*, (especially 4-)methanesulfonylamino-phenyl, (especially 3-)methanesulfonylamino-phenyl*, (especially 4-)carbamoylphenyl, (especially 3-)carbamoyl-phenyl, (especially 4-)(N-methyl-carbamoyl)-phenyl, (especially 4-)(N,N-dimethyl-carbamoyl)-phenyl, (especially 4-)methanesulfonylphenyl*, (especially 3-)methanesulfonylphenyl, (especially 4-)sulfamoylphenyl*, (especially 4-)(N-methylsulfamoyl)-phenyl*, (especially 4-)[N,N-(dimethyl)-sulfamoyl]-phenyl, (especially 4-)morpholinosulfonylphenyl, (especially 4-)cyanophenyl, (especially 3-)cyanophenyl, (especially 3-)nitrophenyl, (especially 3-)amino-4-methyl-phenyl, (especially 3-)amino-4-methoxyphenyl, (especially 3-)amino-4-chlorophenyl, (especially 4-)methoxy-3-nitrophenyl, (especially 4-)morpholin-4-ylmethyl-phenyl, (especially 3-)methyl-(especially 4-)morpholin-4-ylmethyl-phenyl*, (especially 3-)fluoro-(especially 4-)morpholin-4-ylmethyl-phenyl*, (especially 4-)S,S-dioxothiomorpholin-4-ylmethylphenyl*, (especially 3,5-)difluoro-(especially 4-) morpholin-4-ylmethyl-phenyl, (especially 3-)fluoro-(especially 4-)S,S-dioxothiomorpholin-4-ylmethyl-phenyl*, (especially 3,5-)difluoro-(especially 4-)S,S-dioxothiomorpholin-4-ylmethyl-phenyl*, (especially 3-)trifluoromethyl-(especially 4-)morpholin-4-ylmethyl-phenyl, (especially 3,5-)difluoro-(especially 4-)[(preferably 4-)acetyl-piperazin-1-yl]methyl-phenyl, (especially 3,5-)difluoro-(especially 4-)(preferably 4-)piperazin-1-yl]methyl-phenyl, (especially 4-)[(preferably 4-)methyl-piperazin-1-yl]methyl-phenyl, (especially 3,5-)difluoro-(especially 4-)[(especially 3-)oxo-piperazin-1-yl]methyl-phenyl (especially 3,5-)difluoro-(especially 4-)[(preferably 4-)methyl-(especially 3-)oxo-piperazin-1-yl]methyl-phenyl, (especially 4-)imidazol-1-ylmethyl-phenyl, (especially 4-)-4-methylpiperazin-1-carbonyl-phenyl, (especially 4-)morpholin-4-carbonyl-phenyl*, (especially 2- or 3-)fluoro-(especially 4-)morpholin-4-carbonyl-phenyl*, (especially 3-)methyl-(especially 4-)morpholin-4-carbonyl-phenyl*, (especially 3,5-)difluoro-(especially 4-)morpholin-4-carbonyl-phenyl, (especially 4-)S,S-dioxothiomorpholin-4-carbonyl-phenyl, (especially 3-)-fluoro-(especially 4-)S,S-dioxothiomorpholin-4-carbonyl-phenyl*, (especially 4-)morpholin-4-carbonylmethyl-phenyl*, (especially 3-)fluoro-(especially 4-)morpholin-4-carbonylmethyl-phenyl*, [(especially 4-)morpholin-4-carbonyl-(1,1,dimethyl)-methyl]-phenyl, (especially 4-)S,S-dioxothiomorpholin-4-carbonylmethyl-phenyl*, (especially 3-)fluoro-(especially 4-)S,S-dioxothiomorpholin-4-carbonylmethyl-phenyl*, 2H-pyrazol-(especially 3-)yl, (especially 5-)N-methylcarbamoyl-thiophenyl, (especially 4-)pyridyl, (especially 3-)pyridyl, (especially 2-)pyridyl, (especially 6-)methoxy-pyridin-(especially 3-)yl, 1H-benzoimidazol-(especially 5-)yl, quinolin-(especially 6-)yl or isoquinolin-(especially 4-)yl, (where the moieties marked with an asterisk (*) are especially preferred, as are the moieties where the position after "especially" is given) and each of $R^3$ and $R^4$ is hydrogen;

or a pharmaceutically acceptable salt thereof.

The invention relates especially also to a compound of the formula I, wherein

X is CH or N;

$R^1$ is (especially 3,4,5-)trimethoxyphenyl, (especially 3,4- or 3,5-)dimethoxyphenyl, (especially 4-)morpholinophenyl, (especially 4-) N-(2-methoxyethyl)-carbamoylphenyl, or (especially 4-)N,N-(2-dimethylamino-ethyl)-carbamoylphenyl, $R^2$ is phenyl, (especially 4-)methylphenyl, (especially 3-)methylphenyl, (especially 2-)methylphenyl, (especially 4-)aminomethyl-phenyl, (especially 3-)aminomethyl-phenyl, (especially 4-)acetylaminomethyl-phenyl*, (especially 4-)methanesulfonylaminomethyl-phenyl, (especially 3-)acetylaminomethyl-phenyl, (especially 3-)methanesulfonylamino-methyl-phenyl, (especially 4-)methanesulfonylaminomethyl-phenyl, (especially 4-)(N-methylcarbamoyl)-methylphenyl, (especially 4-)methanesulfinylmethylphenyl, (especially 4-)methanesulfonylmethylphenyl, (especially 3-)chlorophenyl, (especially 3-)hydroxyphenyl, (especially 4-)methoxyphenyl, (especially 3-)methoxyphenyl*, (especially 2-)methoxyphenyl, (especially 4-)aminophenyl, (especially 3-)aminophenyl, (especially 2-)aminophenyl, (especially 3-)N-methylamino-phenyl, (especially 4-)N,N-dimethylamino-phenyl, (especially 4-)acetylamino-phenyl, (especially 3-)acetylamino-phenyl, (especially 4-)methanesulfonyl-amino-phenyl*, (especially 4-)methanesulfonylamino-phenyl, (especially 3-) methanesulfonyl-amino-phenyl*, (especially 4-)carbamoylphenyl, (especially 3-)carbamoylphenyl, (especially 4-)(N-methyl-carbamoyl)-phenyl, (especially 4-)(N,N-dimethyl-carbamoyl)-phenyl, (especially 4-)methanesulfonylphenyl*, (especially 3-)methanesulfonylphenyl, (especially 4-)sulfamoylphenyl*, (especially 4-)(N-methylsulfamoyl)-phenyl, (especially 4-)[N,N-

(dimethyl)-sulfamoyl]-phenyl, (especially 4-)morpholinosulfonylphenyl, (especially 4-)cyanophenyl, (especially 3-)cyanophenyl, (especially 3-)nitrophenyl, (especially 3-)amino-4-methyl-phenyl, (especially 3-)amino-4-methoxyphenyl, (especially 3-)amino-4-chlorophenyl, (especially 4-)methoxy-3-nitrophenyl, 2H-pyrazol-(especially 3-)yl, (especially 5-)N-methylcarbamoyl-thiophenyl, (especially 4-)pyridyl, (especially 3-)pyridyl, (especially 2-)pyridyl, (especially 6-)methoxy-pyridin-(especially 3-)yl, 1H-benzoimidazol-(especially 5-)yl, quinolin-(especially 6-)yl or isoquinolin-(especially 4-)yl, (where the moieties marked with an asterisk (*) are especially preferred, as are the moieties where the position after "especially" is given) and each of $R^3$ and $R^4$ is hydrogen;

or a pharmaceutically acceptable salt thereof.

The invention relates especially to the compounds of the formula I given in the Examples, as well as the methods of manufacture described therein.

The general terms used hereinbefore and hereinafter preferably have within the context of this disclosure the following meanings, unless otherwise indicated (where one or more up to all more general expressions in embodiments characterized as preferred above or below can be replaced with a more specific definition, thus leading to a more preferred embodiment of the invention, respectively):

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present.

Any asymmetric carbon atoms (for example in compounds of formula I carrying a substituent with an asymmetric carbon atom) may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention also relates to tautomers where tautomeric forms are possible.

The prefix "lower" or "$C_1$-$C_7$" denotes a radical having up to and including a maximum of 7, especially up to and including a maximum of 4 carbon atoms, the radicals in question being either linear or branched with single or multiple branching.

$C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Halogen (or halo) is especially fluorine, chlorine, bromine, or iodine, especially fluorine, chlorine, or bromine.

That a heterocyclyl is bound via a ring carbon atom means that it is not bound via a nitrogen atom to the rest of the molecule in formula I (that is, to the 7-position of the central benzoxazole ring or if X is N to the 4-position of the central oxazolopyridine ring).

In unsubstituted or substituted aryl, aryl is preferably an aromatic moiety with 6 to 14 ring carbon atoms, more preferably with 6 to 10 ring carbon atoms, such as phenyl or naphthyl, which is unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxopyrrolidino, $C_1$-$C_7$-alkyl-pyrrolidinyl, 2,5-di-($C_1$-$C_7$alkyl)pyrrolidinyl, such as 2,5-di-($C_1$-$C_7$alkyl)-pyrrolidino, tetrahydrofuranyl, thiophenyl, $C_1$-$C_7$-alkylpyrazolidinyl, pyridinyl, $C_1$-$C_7$-alkylpiperidinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkyl-piperazino, morpholino, thiomorpholino, S-oxo-thiomorpholino or S,S-dioxothiomorpholino; $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxyl]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$-alkanoylamino, $C_1$-$C_7$-alkanesulfonylamino, carboxy, lower alkoxy carbonyl, e.g.; phenyl- or naphthyl-lower alkoxycarbonyl, such as benzyloxy-carbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, sulfo (—$SO_3H$), lower alkanesulfonyl, phenyl- or naphthyl-sulfonyl, phenyl- or naphthyl-lower alkylsulfonyl, alkylphenylsulfonyl, halogen-lower alkylsulfonyl, such as trifluoromethanesulfonyl; sulfonamido, benzosulfonamido, azido, azido-$C_1$-$C_7$-alkyl, especially azidomethyl, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxycarbonyl, carbamoyl, cyano and/or sulfamoyl.

In a preferred embodiment, the substituents of substituted aryl are up to three substituents independently selected from the group consisting of $C_1$-$C_7$-alkyl, hydroxyl-$C_1$-$C_7$-alkyl, $C_1$-$C_7$-alkoxy-$C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, ($C_1$-$C_7$-alkoxy-$C_1$-$C_7$-alkyl, $C_1$-$C_7$-alkanoyl or $C_3$-$C_{10}$-cycloalkyl)-oxo-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, 4-($C_1$-$C_7$-alkanoyl)-piperazin-1-yl-$C_1$-$C_7$-alkyl, oxo-piperazin-1-yl-$C_1$-$C_7$-alkyl, imidazol-1-yl-$C_1$-$C_7$-alkyl, pyrrolidin-1-carbonyl-$C_1$-$C_7$-alkyl, piperidin-1-carbonyl-$C_1$-$C_7$-alkyl, piperazin-1-carbonyl-$C_1$-$C_7$-alkyl, 4-($C_1$-$C_7$-alkyl)piperazin-1-carbonyl-$C_1$-$C_7$-alkyl, morpholin-1-carbonyl-$C_1$-$C_7$-alkyl, thiomorpholin-1-carbonyl-$C_1$-$C_7$-alkyl, S-oxo- or S,S-dioxothiomorpholin-1-carbonyl-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl) piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, S-oxo-thiomorpholinosulfonyl, S,S-dioxothiomorpholinosulfonyl, cyano and nitro.

In the case of $R^1$, unsubstituted or substituted aryl is preferably phenyl, naphthyl or indanyl, each of which is unsubstituted or substituted by one to three moieties independently selected from the group consisting of $C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, cyano and nitro; for example, it can be preferably be phenyl or naphthyl that is substituted by one or more, especially one to four substituents independently selected from the group consisting of $C_1$-$C_7$-alkoxy, carbamoyl, N-mono- or N,N-di-($C_1$-$C_7$-alkyl and/or $C_1$-$C_7$-alkyloxy-$C_1$-$C_7$-alkyl)-carbamoyl, N-mono- or N,N-di-{[unsubstituted, N'-mono- or N',N'-di-($C_1$-$C_7$-alkyl)-substituted]-carbamoyl, sulfamoyl, N-mono- or N,N-di-($C_1$-$C_7$-alkyl)-sulfamoyl, piperidino, piperazino, N—$C_1$-$C_7$-alkylpiperazino, morpholino, thiomorpholino, S-oxothiomorpholino and S,S-dioxothiomorpholino, in the case of $R^2$, unsubstituted or substituted aryl is preferably phenyl or naphthyl that is unsubstituted or substituted by one or more, especially up to three, more especially up to two, substituents, preferably not in ortho-position, more preferably with not more than one substituent in meta-position, most preferably with one substituent in meta- and/or one substituent in para position, most preferably with one substituent in meta-position or especially one in para-position, where the substituents are independently selected from the group consisting of $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, $C_1$-$C_7$-alkanesulfonyl-amino, carbamoyl, N-mono- or N,N-di-($C_1$-$C_7$-alkyl)-carbamoyl, $C_1$-$C_7$-alkanesulfonyl, sulfamoyl, N-mono- or N,N-di-($C_1$-$C_7$-alkyl)-sulfamoyl, morpholino-sulfonyl, thiomorpholino-sulfonyl, cyano and nitro.

In the case of unsubstituted or substituted aryl $R^2$, $R^2$ is preferably phenyl which is unsubstituted or substituted by one to three moieties independently selected from the group consisting of $C_1$-$C_7$-alkyl, hydroxyl-$C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, $C_1$-$C_7$-alkanesulfonyl-$C_1$-$C_7$-alkyl, $C_1$-$C_7$-alkanesulfinyl-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, 4-($C_1$-$C_7$-alkanoyl)-piperazin-1-yl-$C_1$-$C_7$-alkyl, oxo-piperazin-1-yl-$C_1$-$C_7$-alkyl, pyrrolidin-1-carbonyl-$C_1$-$C_7$-alkyl, piperidin-1-carbonyl-$C_1$-$C_7$-alkyl, piperazin-1-carbonyl-$C_1$-$C_7$-alkyl, 4-($C_1$-$C_7$-alkyl)piperazin-1-carbonyl-$C_1$-$C_7$-alkyl, morpholin-1-carbonyl-$C_1$-$C_7$-alkyl, thiomorpholin-1-carbonyl-$C_1$-$C_7$-alkyl, S-oxo- or S,S-dioxothiomorpholin-1-carbonyl-$C_1$-$C_7$-alkyl, $C_1$-$C_7$-alkoxy-$C_1$-$C_7$-alkyl, halo-$C_1$-$C_7$-alkyl, $C_1$-$C_7$-alkanoyl or $C_3$-$C_{10}$-cycloalkyl)-oxo-piperazin-1-yl-$C_1$-$C_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, imidazol-1-yl-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkane-sulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, S-oxo-thiomorpholinosulfonyl, S,S-dioxothiomorpholinosulfonyl, cyano and nitro, preferably in the meta, (more preferably once) in the meta (preferably up to once) and the para or in the para position.

In unsubstituted or substituted-heterocyclyl, heterocyclyl is preferably a heterocyclic radical that is unsaturated (=carrying the highest possible number of conjugated double bonds in the ring(s)), saturated or partially saturated and is preferably a monocyclic or in a broader aspect of the invention bicyclic or tricyclic ring; and has 3 to 24, more preferably 4 to 16, most preferably 4 to 10 and most preferably 6 ring atoms; wherein one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; which heterocyclic radical (heterocyclyl) is unsubstituted or substituted by one or more, especially 1 to 3, substituents independently selected from the group consisting of the substituents defined above for substituted alkyl; and where heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]-dioxol-5-yl and 2,3-dihydro-benzo[1,4]dioxin-6-yl, each of these radicals being un-substituted or substituted by one or more, preferably up to three, substituents selected from those mentioned above for substituted aryl and/or from oxo.

In the case of $R^1$, unsubstituted or substituted heterocyclyl is preferably pyrrolyl, oxo-pyrrolyl, 2,3-dihydroindolyl, 2-oxo-2,3-dihydroindolyl or 1H-pyridin-2-onyl, each of which is unsubstituted or substituted by one to three substituents independently selected from those mentioned above for unsubstituted or substituted aryl $R^1$.

In the case of $R^2$, unsubstituted or substituted heterocyclyl is preferably pyridyl, pyrazolyl, thiophenyl, quinolinyl, isoquinolinyl or 1H-benzoimidazolyl, each of which is unsubstituted or substituted by one to three moieties independently selected from those mentioned above as substituents for aryl $R^2$, or especially from the group consisting of $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkane-sulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, $C_1$-$C_7$-alkanesulfonylamino, carbamoyl, N-mono- or N,N-di-($C_1$-$C_7$-alkyl)-carbamoyl, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, cyano and nitro.

X is preferably CH (especially for JAK2 inhibitors of the formula I) or preferably N (especially for JAK3 inhibitors of the formula I).

In $R^2$, preferably not more than one substituent (if a substituent is present at all) is present in ortho-position and in meta position. That is, the substituent or substituents is or are present preferably in para-position and not more than one is present in ortho- and meta-position.

As $R^3$ and $R^4$, hydrogen is especially preferred, respectively.

"Treatment" includes both prophylactic and therapeutic treatment.

Protein tyrosine kinase (especially JAK2 and/or JAK3 kinase) mediated diseases are especially such disorders that respond in a beneficial way (e.g. amelioration of one or more symptoms, delay of the onset of a disease, up to temporary or complete cure from a disease) to the inhibition of a protein tyrosine kinase, especially inhibition of a JAK (preferably JAK2 and/or JAK3) kinase or TYK2, more especially inhibition of JAK2 kinase (where among the diseases to be treated, especially proliferative diseases such as tumor diseases, leukaemias, polycythemia vera, essential thrombocythemia, and myelofibrosis with myeloid metaplasia may be mentioned) and/or of JAK3 kinase (where preferably the treatment (e.g. by immunosuppression) of diseases such as organ transplant rejection, lupus erythematodes, multiple sclerosis, rheumatoid arthritis, psoriasis, dermatitis, Crohn's disease, type-1 diabetes and complications from type-1 diabetes are to be mentioned as preferred.

Salts (which, what is meant by "or salts thereof" or "or a salt thereof", can be present alone or in mixture with free compound of the formula I) are preferably pharmaceutically acceptable salts.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I thereof have valuable pharmacological properties, as described hereinbefore and hereinafter.

They inhibit various protein tyrosine kinases, and especially JAK2 and/or JAK3-receptor tyrosine kinase.

The efficacy of the compounds of the invention as inhibitors of JAK2-receptor tyrosine kinase activity can be demonstrated as follows ("alternative method to that given in the examples"):

Baculovirus including the amino acid domain ASP751-VAL1129 of the JAK2 protein is obtainable by ProQinase, Freiburg, Germany. The virus is scaled up as following: Virus containing media is collected from the transfected cell culture and used for infection to increase its titer. Virus containing media obtained after two rounds of infection is used for large-scale protein expression. For large-scale protein expression 100 $cm^2$ round tissue culture plates are seeded with $5\times10^7$ cells/plate and infected with 1 mL of virus-containing media (approx. 5 MOIs). After 3 days the cells are scraped off the plate and centrifuged at 500 rpm for 5 min. Cell pellets from 10-20, 100 $cm^2$ plates, are re-suspended in 50 mL of ice-cold lysis buffer (25 mMTris-HCl, pH7.5, 2 mMEDTA, 1% NP-40, 1 mM DTT, 1 mMP MSF). The cells are stirred on ice for 15 min and then centrifuged at 5000 rpms for 20 min. The protein is purified by loading the centrifuged cell lysate onto a 2 mL glutathione-sepharose column and washed three times with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% Glycerol and stored at −70° C.

The activity of JAK2 is assayed in the presence or absence of inhibitor measuring the incorporation of 33P from [γ33P] ATP into appropriate substrates [Garcia-Echeverria C, Pearson M A, Marti A, et al (2004) In vivo antitumor activity of NVP-AEW541—A novel, potent, and selective inhibitor of the IGF-IR kinase. Cancer Cell; 5: 231-239]. The test compound is dissolved in DMSO (10 mM) and stored at −20° C. Serial dilutions are freshly made in DMSO and are 1000 times concentrated than test solutions ("pre-dilution plates"). They are further diluted with pure water to yield "master plates" containing 3 times concentrated test solutions in 3% DMSO. The final volume of the assay is 30 μL containing 10 μL of test solution (1% DMSO), 10 μL assay mix including the assay components described by Garcia-Echeverria (2004) and in the following section as well as 10 μL enzyme. The pipetting steps can be programmed to be performed either on the MultiPROBE Iix, MultiPROBE IILx or HamiltonSTAR robots in the 96 well format.

The protein kinase assays are carried as described in details by Garcia-Echeverria (see above). The assay for JAK2 is carried out in 96-well plates at ambient temperature for 10 min (filter-biding method) or 30 min (flash plates) in a finial volume of 30 μL including the following components: 300 ng of GST-JAK2, 20 mM Tris-HCl, pH 7.5, 1.0 mM $MnCl_2$, 10 mM $MgCl_2$, 1 mM DTT, 3 μg/mL poly(Glu, Tyr) 4:1, 1% DMSO and 1.0 μM ATP (γ-[$^{33}$P]-ATP 0.1 μCi); The assays are terminated by the addition of 20 μl of 125 mM EDTA. The capturing of the phosphorylated peptides by the filter-binding method is performed as following: 40 μL of the reaction mixture are transferred onto Immobilon-PVDF membranes previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μl 0.5% $H_3PO_4$. Free membranes are removed and washed 4× on a shaker with 1.0% H3PO4, once with ethanol. Membranes are counted after drying at ambient temperature, mounting in Packard TopCount 96-well frame, and addition of 10 μl/well of Microscint. The plates are eventually sealed and counted in a microplate scintillation counter (TopCount NXT, TopCount NXT HTS, PerkinElmer, Brussels, Belgium).

The assays for the flash plate method is carried out in a total volume of 30 μL at RT in conventional 96-well flash plates. The reaction is stopped after 30 min by the addition of 20 μL of 125 mM EDTA The assay plates are then washed three times with PBS and dried at room temperature. The plates are sealed and counted in a microplate scintillation counter (TopCount NXT, TopCount NXT HTS). IC50 values are calculated by linear regression analysis of the percentage inhibition of the compound either in duplicate, at four concentrations (usually 0.01, 0.1, 1 and 10 μM) or as 8 single point $IC_{50}$ starting at 10 μM following by 1:3 dilutions. With compounds according to the invention, $IC_{50}$ values in the range from 5 nM to 5 μM can be found with compounds of the formula I.

Alternatively, the following assays are made:

1. JAK Kinase Assays ("Lance Assays")

JAK-2 or JAK-3 enzymatic activity is determined using a time-resolved fluorescence energy transfer technology. The phosphorylation of a synthetic biotinylated peptide substrate (GGEEEEYFELVKKKK, SEQ ID NO: 3)) by either JAK-2 or JAK-3 in the presence of ATP is quantified using Europium labeled anti phosphotyrosine antibody and Streptavidin-Allophycocyanin Both JAK-2 and JAK-3 enzymes used in these assays contain the kinase domain (JH-1 domain) of the full length proteins and are used as glutathione S-transferase (GST) fusion proteins.

Inhibitors are dissolved in dimethylsulfoxide (DMSO). Dilutions are prepared in 90% DMSO followed by additional dilutions steps as required to perform a 8-point concentration-response.

The reaction mix consists of 5 μL of diluted compound, 10 μL of assay buffer and 5 μL of enzyme dilution. After incubation for 60 minutes at room temperature the reaction is stopped by the addition of EDTA. For detection of the product anti-phosphotyrosine antibody and Streptavidin-APC are added and after 60 minutes the samples are measured in an EnVision 2102 Multilabel Reader (Perkin Elmer, Inc., Wellesley, Mass., USA, in the following mentioned as "PerkinElmer") with excitation wavelength of 320 nm and emission at 665 nm.

Alternatively, the kinase assays are performed as described in details by Garcia-Echeverria et al [(2004), Cancer Cell; 5:231-239] in 96-well plates at ambient temperature for 10 min (filter-biding method) or 30 min (flash plates) in a final volume of 30 μL including the following components: GST-JAK-2 or GST-JAK-3, 20 mM Tris-HCl, pH 7.5, 0-1.0 mM $MnCl_2$, 1-10 mM $MgCl_2$, 1 mM dithiothreitol (DTT), 3 μg/mL poly(Glu, Tyr) 4:1, 1% DMSO and 1.0 μM ATP (γ-[$^{33}$P]-ATP 0.1 μCi); The assays are terminated by the addition of 20 μl of 125 mM ethylendiamine tetraacetate (EDTA). The capturing of the phosphorylated peptides by the filter-binding method is performed as following: 40 μL of the reaction mixture are transferred onto Immobilon-PVDF membranes previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μl 0.5% $H_3PO_4$. Free membranes are removed and washed 4× on a shaker with 1.0% $H_3PO_4$, once with ethanol. Membranes are counted after drying at ambient temperature, mounting in Packard TopCount 96-well frame (now PerkinElmer), and addition of 10 μl/well of Microscint (PerkinElmer). The plates are eventually sealed and counted in a microplate scintillation counter (TopCount NXT, TopCount NXT HTS, PerkinElmer, Brussels, Belgium).

In these assays, the compounds of the invention have $IC_{50}$ values of from ca. 0.1-1000 nM.

2. JAK-2 and JAK-3 Assays (Filter Binding/Flash Plate Kinase Assays):

Enzyme activities: Enzyme activities are measured by mixing 10 μL of a 3-fold concentrated compound solution with 10 μL of the corresponding substrate mixture (peptidic substrate, ATP and [γ$^{33}$P]ATP) and the reactions are initiated by the addition of 10 μL of a 3-fold concentrated solution of GST- JAK-2 and GST-JAK-3 respectively, in assay buffer. The enzymatic reactions are stopped by the addition of 20 μL of 125 mM EDTA. The incorporation of $^{33}P$ into the substrates is quantified by either filter binding (FB) or flash-plate (FP) method:

Kinase reaction: The assays are carried out in 96-well plates at room temperature for 10 min (FB) in a finial volume of 30 μL including the following components:

JAK-2: 200 ng GST-JAK-2, 20 mM Tris-HCl, pH 7.5, 10 mM $MgCl_2$, 1.0 mM $MnCl_2$, 1 mM DTT, 3 μg/mL poly-EY, 1% DMSO and 1.0 μM ATP (γ-[$^{33}P$]-ATP 0.1 μCi);

JAK-3: 15 ng GST-JAK-3, 20 mM Tris-HCl, pH 7.5, 10 mM $MgCl_2$, 1 mM DTT, 1% DMSO, 3 μg/mL poly-EY and 3.0 μM ATP (γ-[$^{33}P$]-ATP 0.1 μCi);

Filter binding method: The capturing of the phosphorylated peptides by the FB method is performed as following: 40 μL of the stopped reaction mixture were transferred onto Immobilon-PVDF (Millipore, Eschborn, Germany) membranes previously soaked for 5 min with methanol, rinsed with water, soaked for 5 min with 0.5% $H_3PO_4$ and mounted on vacuum manifold with disconnected vacuum source. After spotting, vacuum is connected and each well rinsed with 200 μL 0.5% $H_3PO_4$. Free membranes are removed and washed 4 times on a shaker with 1% $H_3PO_4$ and once with ethanol. Membranes are counted after drying, mounting in Packard TopCount 96-well frame, and addition of 10 μL/well of Microscint™. The plates are eventually sealed and counted in a microplate scintillation counter (TopCount NXT, TopCount NXT HTS).

Flash plate method: For the capturing of the phosphorylated substrates (60 min, RT), 96-well standard FPs (i.e. polystyrene microplates in which the interior of each well is permanently coated with a thin layer of polystyrene-based scintillant) are used. The assay plates are then washed three times with PBS and dried at room temperature. The plates are sealed and counted in a microplate scintillation counter (TopCount NXT, TopCount NXT HTS).

Calculation of $IC_{50}$'s: A 4 Parameter logistic equation is used to calculate $IC_{50}$ values (IDBS XLfit) of the percentage inhibition of each compound at 8 concentrations (usually 10, 3.0, 1.0, 0.3, 0.1, 0.030, 0.010 and 0.003 μM).

Preferably, the test system as described in Example 186 is used.

Preferably, $IC_{50}$ values in the range from 0.1 nM to 10 μM, e.g. from less than 3 nM to 5 μM, most preferably from 0.1 nM to 1000 nM can be found in the above-mentioned test systems.

The activity of the compounds of the formula I can also be determined in vivo:

JAK-2 In Vivo

The assay can be performed as described by G. Wernig, T. Mercher, R. Okabe, R. L. Levine, B. H. Lee, D. G. Gilliland, Blood First Edition paper, published online Feb. 14, 2006; DOI 10, 1182/blood-2005-12-4824.

On the basis of these studies, a compound of formula I according to the invention shows therapeutic efficacy especially against disorders dependent on protein kinase, especially proliferative diseases mediated JAK2 kinase activity.

In addition, further protein kinases can be inhibited by compounds of the present invention, such as Tyk 2, c-src, Flt-3, KDR and others, for each of which test systems are known in the art.

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of a compound of the formula I or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, divided preferably into 1 to 3 single doses which may, for example, be of the same size. Usually, children receive half of the adult dose.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Thus, a compound of the formula I may be used to advantage in combination with other anti-proliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Further, alternatively or in addition they may be used in combination with other tumor treatment approaches, including surgery, ionizing radiation, photo-dynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C (PKC) and Raf family of serine/threonine kinases, members of the MEK. SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitory as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt.

Somatostatin receptor antagonists as used herein refers to compounds which target, treat or inhibit the somatostatin receptor such as octreotide, and SOM230.

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al. *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al. *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium. Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammator or antihistamine drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

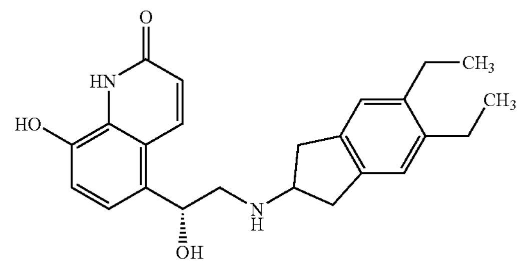 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, or the PDGF receptor tyrosine kinase, e.g. STI571 (Glivec®), a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The above-mentioned compounds, which can be used in combination with a compound of the formula I, can be prepared and administered as described in the art, such as in the documents cited above.

By "combination", there is meant either a fixed combination in one dosage unit form, or a kit of parts for the combined administration where a compound of the formula (I) and a combination partner may be administered independently at the same time or separately within time intervals, especially where these time intervals allow that the combination partners show a cooperative, e.g. synergistic effect.

The invention also provides a pharmaceutical preparation, comprising a compound of formula I as defined herein, or a pharmaceutically acceptable salt of such a compound, or a hydrate or solvate thereof, and at least one pharmaceutically acceptable carrier.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned diseases (=disorders), of a compound of formula I or a pharmaceutically acceptable salt thereof together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approximately 1% to approximately 20%, active ingredients).

Additionally, the present invention provides a compound of formula I or an N-oxide or a tautomer thereof, or a pharmaceutically acceptable salt of such a compound, for use in a method for the treatment of the human or animal body, especially for the treatment of a disease mentioned herein, most especially in a patient requiring such treatment.

Furthermore, the invention relates to a method for the treatment of a disease which responds to an inhibition of JAK-2 and/or Jak-3 kinase, which comprises administering a compound of formula I or a pharmaceutically acceptable salt thereof, wherein the radicals and symbols have the meanings as defined above, especially in a quantity effective against said disease, to a warm-blooded animal requiring such treatment.

Furthermore, the invention relates to a pharmaceutical composition for treatment of a disease, e.g. of solid or liquid tumours in warm-blooded animals, including humans, comprising a dose effective in the treatment of said disease of a compound of the formula I as described above or a pharmaceutically acceptable salt of such a compound together with a pharmaceutically acceptable carrier (=carrier material).

Processes of Manufacture

A compound of the formula I may be prepared by processes that, though not applied hitherto for the new compounds of the present invention where they thus form new processes, are known per se: preferably, a process for the manufacture of a compound of the formula I comprises either a) reacting a compound of the formula II, (II)

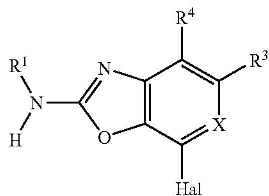

wherein X, $R^1$, $R^3$ and $R^4$ are as defined for a compound of the formula I and Hal is halo, especially bromo, under Suzuki coupling conditions with a boronic acid of the formula III,

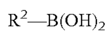

(III)

wherein $R^2$ is as defined for a compound of the formula I, or a reactive derivative thereof, or b) reacting a compound of the formula II, (II)

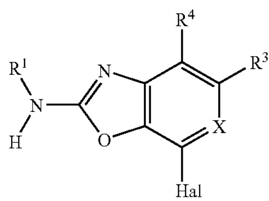

wherein X, $R^1$, $R^3$ and $R^4$ are as defined for a compound of the formula I and Hal is halo, especially bromo, under Stille coupling conditions with an organotin compound of the formula III*

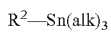

(III*)

wherein $R^2$ is as defined for a compound of the formula I and alk is alkyl, preferably $C_1$-$C_7$-alkyl, and, if desired, converting an obtainable compound of the formula I into a different compound of the formula I, converting an obtainable salt of a compound of the formula I into a different salt thereof, converting an obtainable free compound of the formula I into a salt thereof, and/or separating an obtainable isomer of a compound of the formula I from one or more different obtainable isomers of the formula I.

The reaction a) preferably takes place under Suzuki(-Miyaura) conditions, that is, by palladium-catalyzed cross-coupling of organoboranes, by reacting the halo-carrying compound of the formula II with the boronic acid of the formula III, or a reactive derivative thereof.

A reactive derivative of a boronic acid of the formula III is preferably one wherein instead of the hydroxyl groups at the boron atom an aryl, alkenyl or especially alkyl moiety is present, or wherein the OH groups are present in bridged form, e.g., together with the boron atom, forming a group of the formula (A)

(A)

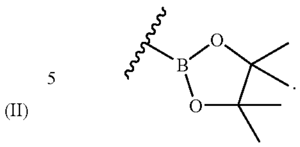

The reaction preferably takes place in a mixture of a polar aprotic solvent, such as dimethylformamide (DMF) or tetrahydrofurane, and water in the presence of a catalyst for the crosscoupling, especially a noble metal catalyst, preferably a palladium catalyst, such as palladium(II) complex, for example bis(triphenylphosphine)palladium (II) dichloride, in the presence of a base, such as potassium carbonate, sodium hydroxide or sodium carbonate, at a preferred temperature in the range from 60° C. to 130° C., e.g. at about 80° C.; or according to a another preferred method in an ether solvent, e.g. tetrahydrofurane or 1,2-dimethoxyethane, in the presence of a catalyst for the cross coupling, especially a noble metal catalyst, preferably a palladium (0) complex, for example tris(dibenzylideneacetone)-dipalladium(0) or tetrakis (triphenylphosphin)palladium(0), in the presence of a base, such as sodium hydroxide, potassium carbonate of sodium carbonate, if desired in the presence of an appropriate ligand, such as 2-dicyclohexylphosphino-2',6'-dimethoxybiphenyl (SPhos), at a preferred temperature in the range from 60 to 150° C., preferably from 70 to 110° C.; if required conducting the reaction in a sealed vessel (e.g. a seal reactor) if the boiling point of the reaction mixture is exceeded and especially if the heating is effected by microwave excitation. Preferably, oxygen is excluded, e.g. by the presence of an inert gas, such as nitrogen or especially argon.

The reaction b) given above is wherein in formula III* alk is alkyl, preferably $C_1$-$C_7$-alkyl, more preferably methyl, is preferably conducted under Stille coupling conditions, or in analogy thereto, preferably in an appropriate polar solvent, such as N,N-dimethylacetamide or N,N-dimethylformamide, an ether, such as tetrahydrofurane or dimethoxy-ethane, and/or a mixture of two or more such solvents, in the presence of a palladium catalyst, especially a palladium (0) complex, for example tetrakistriphenylpalladium, e.g. at temperatures in the range from 80 to 160° C., if required conducting the reaction in a sealed vessel (e.g. a seal reactor or a microwave vessel) if the boiling point of the reaction mixture is exceeded and/or especially if (as is a preferred embodiment) the heating is effected by microwave excitation.

Where temperatures are given hereinbefore or hereinafter, "about" has to be added, as minor deviations from the numeric values given, e.g. variations of ±10%, are tolerable.

Protecting Groups

If one or more other functional groups, for example carboxy, hydroxy, amino, sulfhydryl or the like are or need to be protected in a starting material of the formula II or III or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which is groups that are added at a starting material or intermediate stage and removed to obtain a final compound. Also in the case of conversions of a compound of the formula I into a different compound of the formula I, protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/l, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Optional Reactions and Conversions

A compound of the formula I may be converted into a different compounds of the formula I.

For example, in a compound of the formula I wherein $R^1$ or especially $R^2$ carries an amino or amino-$C_1$-$C_7$-alkyl substituent, the amino can be converted into acylamino, e.g. $C_1$-$C_7$-alkanoylamino or $C_1$-$C_7$-alkanesulfonylamino, by reaction with a corresponding $C_1$-$C_7$-alkanoylhalogenide or $C_1$-$C_7$-alkanesulfonylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

In a compound of the formula I wherein $R^1$ or especially $R^2$ carries a cyano substituent, the cyano may be converted to an aminomethyl group, e.g. by hydrogenation in the presence of an appropriate metal catalyst, such as Raney Nickel or Raney Cobalt, in an appropriate solvent, e.g. a lower alkanol, such as methanol and/or ethanol, for example at temperatures in the range from −20 to 50° C., e.g. at about room temperature.

In a compound of the formula I wherein $R^1$ or especially $R^2$ carries a carboxyl (COOH) substituent, the latter can be converted into an amide group, e.g. an N—$C_1$-$C_7$-alkyl-carbamoyl group, by reaction with the corresponding amine, e.g. in the presence of a coupling agent, that forms a preferred reactive derivative of the carboxyl group in situ, for example dicyclohexylcarbodiimide/1-hydroxybenzotriazole (DCC/HOBT); bis(2-oxo-3-oxazolidinyl)phosphinic chloride (BOPCI); 0-(1,2-dihydro-2-oxo-1-pyridyl)-N,N,N',N'-tetramethyl-uronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluoro-phosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* (1972), 453-463. The reaction mixture is preferably stirred at a temperature of between approximately −20 and 50° C., especially between 0° C. and 30° C., e.g. at room temperature.

In a compound of the formula I wherein $R^1$ or especially $R^2$ carries two vicinal amino groups, the two nitrogen atoms of the two amino groups can be bridged by a —CH═ group (thus forming, together with the two carbon atoms that bind the original amino groups and the bond between them, an 1H-imidazolo ring annelated to $R^1$ or $R^2$; for example, (vicinal diamino)-phenyl can be converted into benzoimidazolyl according to this method. The reaction preferably takes place by first reacting the compound of the formula I carrying the two vicinal amino groups with formic acid, e.g. in the presence of a coupling agent as mentioned in the preceding paragraph, such as EDC hydrochloride, a base, such as N,N-dimethylaminopyridine (DMAP) and preferably an appropriate solvent, such as methylene chloride, e.g. at temperatures in the range from −20 to 50° C., e.g. at about room temperature, thus converting one (especially a para-positioned) of the vicinal amino groups into a formylamino group. In a second step, the amino and formylamino group are then reacted to —N═C—N— by heating in the presence of an acid, especially acetic acid, e.g. at temperatures in the range from 50 to 110° C., for example at about 100° C.

Note that the intermediate with the formylamino group obtainable by the first reaction in the preceding paragraph is also a compound of the formula I, so that this first reaction also is a conversion reaction according to the invention.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates (and are thus useful in the preparation of corresponding starting materials).

Starting Materials:

The starting materials of the formulae II and III, as well as other starting materials mentioned herein, e.g. below, can be prepared according to or in analogy to methods that are known in the art, are known in the art and/or are commercially available. Novel starting materials, as well as processes for the preparation thereof, are likewise an embodiment of the present invention. In the preferred embodiments, such starting materials are used and the reaction chosen are selected so as to enable the preferred compounds to be obtained.

In the starting materials (including intermediates), which may also be used and/or obtained as salts where appropriate and expedient, $R^1$, $R^2$, $R^3$, $R^4$ and X are preferably as defined for a compound of the formula I. Hal is halogen, especially chloro or bromo.

A compound of the formula II can, for example, be obtained by reacting a thiourea compound of the formula IV,

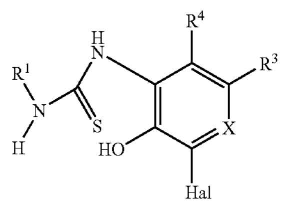

(IV)

under cyclization in the presence of an organic sulfonyl chloride, such as toluene-4-sulfonyl chloride, in an appropriate solvent, e.g. a cyclic ether, such as tetrahydrofurane, in the presence of water and a base, such as sodium hydroxide, at temperatures in the range from −20 to 50° C., e.g. at about room temperature.

A thiourea compound of the formula IV can, for example, be prepared from an amino phenol of the formula V,

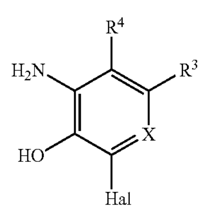

(V)

by reacting it with an isothiocyanate of the formula VI, $$R^1\text{—N═C═S} \quad (VI)$$

e.g. in an appropriate solvent, e.g. a cyclic ether, such as tetrahydrofurane, at temperatures e.g. in the range from −20 to 50° C., e.g. at about room temperature.

A compound of the formula V may, for example, be prepared by reducing a nitro compound of the formula VII,

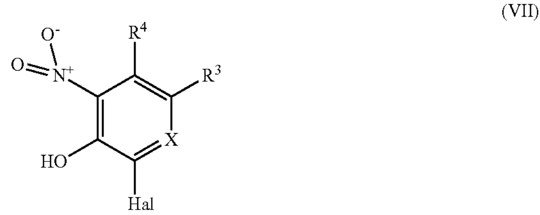

(VII)

e.g. with hydrogen in the presence of a catalyst, such as Raney-Nickel (Ra—Ni) or Raney Cobalt or the like, in an appropriate solvent, such as an alcohol, e.g. methanol, and/or a cyclic ether, such as tetrahydrofurane, at temperatures e.g. in the range from −20 to 50° C., e.g. at about room temperature.

Alternatively, a compound of the formula II can be prepared by reacting a methyl sulfanyl compound of the formula VIII,

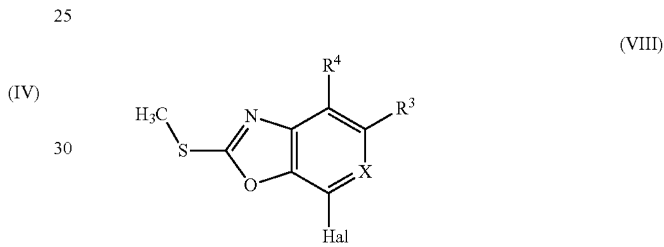

(VIII)

with an amine of the formula IX, $$R^1\text{NH—} \quad (IX)$$

e.g. without solvent (e.g. in a melt or by dissolving the compound of the formula VIII in the amine of the formula IX) at elevated temperatures e.g. in the range from 50 to 150° C., e.g. at about 100° C. This reaction can preferably be conducted, in the presence of an agent capable of oxidising the methanesulfanyl at the oxazole ring to the methanesulfinyl, e.g. in the presence of a peroxide, such as m-chloroperbenzoic acid, and appropriate solvent, such as dichloromethane, preferably at temperatures in the range from 0 to 50° C., e.g. at about room temperature.

A compound of the formula VIII can, for example, be prepared by reacting a thiol compound of the formula X,

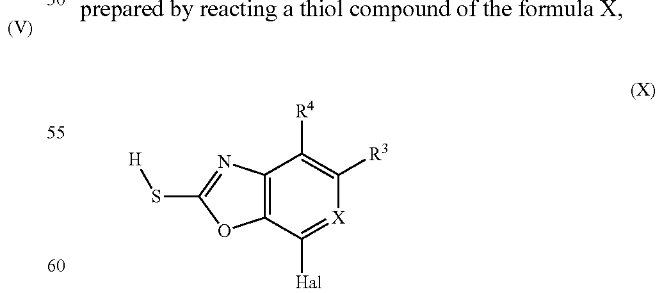

(X)

in an appropriate solvent, e.g. a dialkyl carboxylic acid amide, such as dimethylformamide, in the presence of a base, e.g. an alkali metal (such as potassium) carbonate, at temperatures e.g. in the range from −20 to 50° C., e.g. at about room temperature, with a methyl halogenide, e.g. methyl iodide.

A compound of the formula X can, for example, be prepared from a compound of the formula V described (and obtainable as) above by reacting it with an alkali metal ethyl xanthogenate, such as potassium ethyl xanthogenate, in an appropriate solvent, such as an alcohol, e.g. ethanol, preferably at elevated temperatures, e.g. in the range from 50° C. to the reflux temperature of the reaction mixture, e.g. under reflux.

A compound of the formula III* can, for example, be prepared from a compound of the formula XI, $$R^2\text{-Hal} \quad \text{(XI)}$$

wherein Hal is halo, especially bromo, by reaction with a hexa-alkyl tin, especially hexa-$C_1$-$C_7$-alkyl-tin, e.g. hexamethyltin, in an appropriate solvent, such as toluene, and a customary noble metal catalyst, such as tetrakis(triphenylphosphine)palladium, preferably at elevated temperatures e.g. in the range from 50 to 150° C.

Other starting materials, e.g. those of the formula VI, VII, IX, X and XI, are known in the art, can be prepared according to or in analogy to methods that are known in the art or in analogy to methods described in the Examples, and/or they are commercially available.

The following examples serve to illustrate the invention without limiting the scope thereof.

If not indicated otherwise, reactions take place at room temperature. Abbreviations used are:

Ac acetate

Ahx aminohexanoic acid

Brij 35 Polyoxyethylene(23)-laurylether (trademark of ICI Americas, Inc.)

BSA bovine serum albumine

DMAP N,N-dimethylaminopyridine

DMF dimethyl formamide

DTT Di-thiothreitol

DMSO dimethyl sulfoxide

EDC 1-(3-dimethylaminopropyl)-3-ethylcarbodiimide

EDTA ethylenediamine tetraacetate $Et_3N$ triethylamine

EtOAc ethyl acetate

FITC fluoresceine-isothiocyanate derived fluoresceine moiety h hour(s)

Hepes 4-(2-hydroxyethyl)-1-piperazineethanesulfonic acid

HOBT 1-hydroxybenzotriazole

MeOH methanol min minute(s)

MS Mass Spectrometry

Ra—Ni Raney-Nickel $R_t$ Retention time

RT room temperature sat. saturated (at RT)

TFA trifluoro acetic acid

THF tetrahydrofurane

Tween 20 Polyoxyethylen(20)-sorbitan-monolaurate (ICI Americas, Inc.)

EXAMPLE 1

(7-m-Tolyl-benzooxazol-2-yl)-(3,4,5-trimethoxy-phenyl)-amine

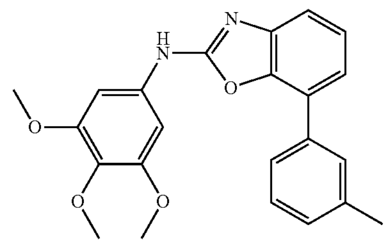

0.12 g (0.316 mmol) (7-bromo-benzooxazol-2-yl)-(3,4,5-trimethoxy-phenyl)-amine and 0.048 g (0.353 mmol) 3-tolyl boronic acid are dissolved in 4 ml 1,2-dimethoxy-ethane, a solution of 0.1 g (0.95 mmol) $Na_2CO_3$ (in 0.5 ml water) is added and a stream of argon is bubbled through the mixture in order to exclude oxygen from the reaction mixture. Tetrakis (triphenylphosphine) palladium (76 mg, 0.064 mmol) is added and the reaction mixture is stirred at 100° C. or 3 h. After that the reaction mixture is poured on water and extracted 3× with EtOAc. The combined organic layers are washed with water, dried over $MgSO_4$, filtered and the filtrate is concentrated in vacuo. The residue is purified by chromatography (silicagel, hexane:EtOAc=3:1=>1:1) to afford the title compound as an off-white solid, m.p. 153-155° C. $R_t$=2.54 min (Waters Symmetry C8, 2.1×50 mm, detection 210-250 nM, 5% to 100% $CH_3CN$ in $H_2O$ in 2 min+0.05% TFA, flow rate 1.0 ml/min). MS: 391 $(M+1)^+$; m.p. 155-158° C.

The starting materials can be prepared as follows:

a) (7-Bromo-benzooxazol-2-yl)-(3,4,5-trimethoxy-phenyl)-amine

To a suspension of 0.798 mg (1.93 mmol) 1-(3-bromo-2-hydroxy-phenyl)-3-(3,4,5-trimethoxy-phenyl)-thiourea in 8 ml THF, 0.197 g (4.8 mmol) NaOH (in 5 ml water) and 0.419 g (2.12 mmol) toluene-4-sulfonyl chloride are added. The reaction mixture is stirred at room temperature for 1.5 h. Then the reaction mixture is concentrated in vacuo. To the residue EtOAc and sat. NaCl-solution are added and the layers are separate. The water layer is extracted 3× with EtOAc. The combined organic layers are washed with water, dried over $MgSO_4$, filtered and the filtrate is concentrated in vacuo. The residue is stirred in diethyl ether, filtered and dried to afford the title compound.

b) 1-(3-Bromo-2-hydroxy-phenyl)-3-(3,4,5-trimethoxy-phenyl)-thiourea

A mixture of 0.376 g (2.0 mmol) 2-amino-6-bromo-phenol and 0.46 g (2.0 mmol) 3,4,5-trimethoxy-isothiocyanate in 10 ml THF is stirred at room temperature for ca. 20 h. The reaction mixture is concentrated in vacuo, followed by the addition of toluene and concentration. The toluene addition and evaporation is repeated one more time to afford the title compound as a brown solid.

c) 2-Amino-6-bromo-phenol 5 g (22.9 mmol) 2-nitro-6-bromo-phenol (Fluka 67211) is hydrogenated in the presence of 0.1 g Ra—Ni (B113W EtOH, Degussa) in 100 ml of THF:MeOH=1:1. for 4 h. The reaction mixture is filtered (2 glass fiber filters used) and the filtrate is concentrated in vacuo. The residue is purified by chromatography (silicagel, hexane:EtOAc=2:1) to afford the title compound as a reddish oil which slowly solidifies.

Using the same synthetic methods as described in example 1, reaction of (7-bromo-benzooxazol-2-yl)-(3,4,5-trimethoxy-phenyl)-amine and the appropriate boronic acid derivative leads to the following examples:

EXAMPLE 2

(7-Phenyl-benzooxazol-2-yl)-(3,4,5-trimethoxy-phenyl)-amine $R_t$=2.47 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 377 $(M+1)^+$; m.p. 182-185° C.

EXAMPLE 3

(7-Pyridin-3-yl-benzooxazol-2-yl)-(3,4,5-trimethoxy-phenyl)-amine $R_t$=1.80 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 378 $(M+1)^+$; m.p. 165-170° C.

EXAMPLE 4

[7-(3-Methoxy-phenyl)-benzooxazol-2-yl]-(3,4,5-trimethoxy-phenyl)-amine $R_t$=2.45 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 407 $(M+1)^+$; m.p. 167-170° C.

EXAMPLE 5

[7-(2-Methoxy-phenyl)-benzooxazol-2-yl]-(3,4,5-trimethoxy-phenyl)-amine $R_t$=2.40 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 407 $(M+1)^+$; m.p. 185-187° C.

EXAMPLE 6

[7-(3-Hydroxy-phenyl)-benzooxazol-2-yl]-(3,4,5-trimethoxy-phenyl)-amine $R_t$=2.22 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 393 $(M+1)^+$.

EXAMPLE 7

[7-(4-Methoxy-phenyl)-benzooxazol-2-yl]-(3,4,5-trimethoxy-phenyl)-amine $R_t$=2.44 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 407 $(M+1)^+$; m.p. 179-182° C.

EXAMPLE 8

(7-Isoquinolin-4-yl-benzooxazol-2-yl)-(3,4,5-trimethoxy-phenyl)-amine $R_t$=1.90 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 428 $(M+1)^+$; m.p. 201-203° C.

EXAMPLE 9

[7-(3-Chloro-phenyl)-benzooxazol-2-yl]-(3,4,5-trimethoxy-phenyl)-amine $R_t$=2.60 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 411 $(M+1, {}^{35}Cl)^+$; m.p. 199-201° C.

EXAMPLE 10

[7-(3-Amino-phenyl)-benzooxazol-2-yl]-(3,4,5-trimethoxy-phenyl)-amine $R_t$=1.88 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 392 $(M+1)^+$; m.p. 145-170° C.

EXAMPLE 11

[7-(4-Amino-phenyl)-benzooxazol-2-yl]-(3,4,5-trimethoxy-phenyl)-amine $R_t$=1.86 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 392 $(M+1)^+$; m.p. 192-196° C.

EXAMPLE 12

[7-(6-Methoxy-pyridin-3-yl)-benzooxazol-2-yl]-(3,4,5-trimethoxy-phenyl)-amine $R_t$=2.31 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 408 $(M+1)^+$; m.p. 192-193° C.

EXAMPLE 13

[7-(3-Amino-4-methyl-phenyl)-benzooxazol-2-yl]-(3,4,5-trimethoxy-phenyl)-amine $R_t$=1.94 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 406 $(M+1)^+$; m.p. 188-190° C.

EXAMPLE 14

[7-(2-Amino-phenyl)-benzooxazol-2-yl]-(3,4,5-trimethoxy-phenyl)-amine $R_t$=2.06 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 392 $(M+1)^+$

EXAMPLE 15

(7-Quinolin-6-yl-benzooxazol-2-yl)-(3,4,5-trimethoxy-phenyl)-amine $R_t$=1.91 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 428 $(M+1)^+$; m.p. 187-190° C.

EXAMPLE 16

4-[2-(3,4,5-Trimethoxy-phenylamino)-benzooxazol-7-yl]-benzamide $R_t$=2.08 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 420 $(M+1)^+$; m.p.>280° C.

EXAMPLE 17

[7-(4-Methanesulfonyl-phenyl)-benzooxazol-2-yl]-(3,4,5-trimethoxy-phenyl)-amine $R_t$=2.26 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 455 $(M+1)^+$; m.p. 205-207° C.

EXAMPLE 18

4-[2-(3,4,5-Trimethoxy-phenylamino)-benzooxazol-7-yl]-benzenesulfonamide $R_t$=2.16 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 456 $(M+1)^+$; m.p. 247-252° C.

EXAMPLE 19

4-[2-(3,4,5-Trimethoxy-phenylamino)-benzooxazol-7-yl]-benzonitrile $R_t$=2.42 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 402 $(M+1)^+$; m.p. 222-223° C.

EXAMPLE 20

[7-(2H-Pyrazol-3-yl)-benzooxazol-2-yl]-(3,4,5-trimethoxy-phenyl)-amine $R_t$=2.00 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 367 $(M+1)^+$; m.p. 185-189° C.

EXAMPLE 21

N-Methyl-4-[2-(3,4,5-trimethoxy-phenylamino)-benzooxazol-7-yl]-benzenesulfonamide $R_t$=2.26 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 470 $(M+1)^+$; m.p. 260-262° C.

EXAMPLE 22

N,N-Dimethyl-4-[2-(3,4,5-trimethoxy-phenylamino)-benzooxazol-7-yl]-benzenesulfonamide $R_t$=2.39× min (Waters Symmetry C8, 2.1×50 mm, detection 210-250 nM, 5% to 100% $CH_3CN$ in $H_2O$ in 2 min+0.05% TFA, flow rate 1.0 ml/min); MS: 484 $(M+1)^+$; m.p. 230-233° C.

EXAMPLE 23

{7-[4-(Morpholine-4-sulfonyl)-phenyl]-benzooxazol-2-yl}-(3,4,5-trimethoxy-phenyl)-amine $R_t$=2.36 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 526 $(M+1)^+$; m.p. 201-203° C.

EXAMPLE 24

N-Methyl-4-[2-(3,4,5-trimethoxy-phenylamino)-benzooxazol-7-yl]-benzamide $R_t$=2.13 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 434 $(M+1)^+$; m.p. 258-259° C.

EXAMPLE 25

N,N-Dimethyl-4-[2-(3,4,5-trimethoxy-phenylamino)-benzooxazol-7-yl]-benzamide $R_t$=2.19 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 448 $(M+1)^+$; m.p.>280° C.

EXAMPLE 26

N-{4-[2-(3,4,5-Trimethoxy-phenylamino)-benzooxazol-7-yl]-phenyl}-methanesulfonamide A mixture of 0.12 g (0.307 mmol) [7-(4-amino-phenyl)-benzooxazol-2-yl]-(3,4,5-trimethoxy-phenyl)-amine (example 11) and 0.041 g (0.36 mmol) methanesulfonyl chloride in 6 ml pyridine is stirred for 1.5 h at room temperature. Then the reaction mixture is poured on water and extracted 3× with EtOAc. The combined organic layers are washed with 0.1N NaOH solution and water, dried over $MgSO_4$, filtered and the filtrate is concentrated in vacuo. The residue is purified by crystallisation from dichloromethane/diethyl ether to afford the title compound as off-white crystals. $R_t$=2.22 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 470 $(M+1)^+$; m.p. 222-225° C.

EXAMPLE 27

N-{4-[2-(3,4,5-Trimethoxy-phenylamino)-benzooxazol-7-yl]-phenyl}-acetamide

A mixture of 0.075 g (0.1927 mmol) [7-(4-amino-phenyl)-benzooxazol-2-yl]-(3,4,5-trimethoxy-phenyl)-amine (example 11), 0.027 ml triethylamine and 0.016 g (0.199 mmol) acetyl chloride in 4 ml dichloromethane is stirred for 1 h at room temperature. Then the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, EtOAc) to afford the title compound as orange crystals. $R_t$=2.16 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 434 $(M+1)^+$; m.p. 265-270° C.

Using the same reaction conditions the following example is prepared from [7-(3-amino-phenyl)-benzooxazol-2-yl]-(3,4,5-trimethoxy-phenyl)-amine (Example 10):

EXAMPLE 28

N-{3-[2-(3,4,5-Trimethoxy-phenylamino)-benzooxazol-7-yl]-phenyl}-acetamide $R_t$=2.21 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 434 $(M+1)^+$; m.p. 170-172° C.

EXAMPLE 29

[7-(4-Aminomethyl-phenyl)-benzooxazol-2-yl]-(3,4,5-trimethoxy-phenyl)-amine

To a solution of 0.117 g (0.291 mmol) 4-[2-(3,4,5-trimethoxy-phenylamino)-benzooxazol-7-yl]-benzonitrile (example 19) in 5 ml MeOH (MeOH contains 5% $NH_3$), 5 ml THF and 30 mg Ra—Ni (B113W EtOH, Degussa) are added. Then this mixture is hydrogenated under normal pressure for 20 h at room temperature. The reaction mixture is filtered (2 glass fiber filters used) and the filtrate is concentrated in vacuo. The residue is purified by crystallization from dichloromethane/diethyl ether to afford the title compound as a light grey solid. $R_t$=1.85 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 406 $(M+1)^+$; m.p. 208-211° C.

EXAMPLE 30

N-{4-[2-(3,4,5-Trimethoxy-phenylamino)-benzooxazol-7-yl]-benzyl}-acetamide

A mixture of 0.070 g (0.173 mmol) [7-(4-aminomethyl-phenyl)-benzooxazol-2-yl]-(3,4,5-trimethoxy-phenyl)-amine (example 29), 1 ml pyridine and 0.016 g (0.199 mmol) acetyl chloride is stirred for 1.5 h at room temperature. Then the reaction mixture is poured on water and extracted 2× with EtOAc. The combined organic layers are washed with water and 0.1N NaOH solution, dried over $MgSO_4$, filtered and the filtrate is concentrated in vacuo and co-evaporated twice with toluene. The residue is purified by crystallization from dichloromethane/diethyl ether to afford the title compound as a light brown solid. $R_t$=2.12 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 448 $(M+1)^+$; m.p. 237-239° C.

EXAMPLE 31

N-{4-[2-(3,4,5-Trimethoxy-phenylamino)-benzooxazol-7-yl]-benzyl}-methanesulfonamide A mixture of 0.10 g (0.247 mmol) [7-(4-aminomethyl-phenyl)-benzooxazol-2-yl]-(3,4,5-trimethoxy-phenyl)-amine (example 29) and 0.037 g (0.32 mmol) methanesulfonyl chloride in 4 ml pyridine is stirred for 1.5 h at room temperature. Then the reaction mixture is poured on water and extracted 3× with EtOAc. The combined organic layers are washed with 0.1N NaOH solution and water, dried over $MgSO_4$, filtered and the filtrate is concentrated in vacuo and co-evaporated twice with toluene. The residue is purified by crystallisation from dichloromethane to afford the title compound as off-white crystals. $R_t$=2.20 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 474 $(M+1)^+$.

Using the synthetic methods described in examples 29 and 30, the following examples are prepared:

EXAMPLE 32

[7-(3-Aminomethyl-phenyl)-benzooxazol-2-yl]-(3,4,5-trimethoxy-phenyl)-amine $R_t$=1.86 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 406 $(M+1)^+$; m.p. 145-150° C.

EXAMPLE 33

N-{3-[2-(3,4,5-Trimethoxy-phenylamino)-benzooxazol-7-yl]-benzyl}-acetamide $R_t$=2.16 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 448 $(M+1)^+$; m.p. 203-204° C.

EXAMPLE 34

4-[2-(3,4,5-Trimethoxy-phenylamino)-benzooxazol-7-yl]-thiophene-2-carboxylic acid methylamide A mixture of 0.04 g (0.083 mmol) 4-[2-(3,4,5-trimethoxy-phenylamino)-benzooxazol-7-yl]-thiophene-2-carboxylic acid, 0.025 g (0.127 mmol) EDC-HCl, 0.016 g (0.128 mmol) DMAP, 0.83 ml (1.7 mmol) methylamine THF solution (2M), 0.012 g (0.088 mmol) HOBt and 4 ml dichloromethane is stirred at room temperature for 72 h. Then EtOAc is added to the reaction mixture and the organic layer is washed with water (2×), dried over $MgSO_4$, filtered and the filtrate is concentrated in vacuo. The residue is purified by chromatography (silicagel, hexane:EtOAc=1:2), followed by crystallization from dichloromethane/diethyl ether to afford the title compound as off-white crystals. $R_t$=2.15 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 440 $(M+1)^+$; m.p. 260-262° C.

The starting material 4-[2-(3,4,5-trimethoxy-phenylamino)-benzooxazol-7-yl]-thiophene-2-carboxylic acid is prepared from 2-carboxythiophene-4-boronic acid pinacol ester as described in Example 1.

EXAMPLE 35

[7-(1H-Benzoimidazol-5-yl)-benzooxazol-2-yl]-(3,4,5-trimethoxy-phenyl)-amine

A solution of 0.182 g (0.243 mmol) N-{2-amino-4-[2-(3,4,5-trimethoxy-phenylamino)-benzooxazol-7-yl]-phenyl}-formamide in 3 ml acetic acid is stirred at 100° C. for 1 h. Then EtOAc is added to the reaction mixture and the organic layer is washed with 4N NaOH solution (2×) and with water (2×), dried over $MgSO_4$, filtered and the filtrate is concentrated in vacuo. The residue is purified by chromatography (silicagel, EtOAc=>EtOAc:MeOH=95:5) to afford the title compound as an orange solid. $R_t$=1.86 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 417 $(M+1)^+$; m.p. 150-156° C.

The starting material N-{2-amino-4-[2-(3,4,5-trimethoxy-phenylamino)-benzooxazol-7-yl]-phenyl}-formamide is prepared as follows:

A mixture of 0.16 g (0.228 mmol) 4-[2-(3,4,5-trimethoxy-phenylamino)-benzooxazol-7-yl]-benzene-1,2-diamine, 0.068 g (0.346 mmol) EDC-HCl, 0.043 g (0.345 mmol) DMAP, 0.012 g (0.27 mmol) formic acid), and 7 ml dichloromethane is stirred at room temperature for 20 h. Then the reaction mixture is concentrated in vacuo. The residue is purified by chromatography (silicagel, EtOAc:MeOH=9:1) to afford ca. the title compound. 4-[2-(3,4,5-trimethoxy-phenylamino)-benzooxazol-7-yl]-benzene-1,2-diamine is prepared from 4-(4,4,5,5-tetramethyl-[1,3,2]dioxaborolan-2-yl)-benzene-1,2-diamine as described in Example 1.

4-(4,4,5,5-tetramethyl-[1,3,2]dioxaborolan-2-yl)-benzene-1,2-diamine is prepared from the commercially available 2-nitro-4-(4,4,5,5-tetramethyl-[1,3,2]dioxaborolan-2-yl)-phenylamine using the Ra—Ni catalyzed nitro reduction method described in Example 1 (step c).

EXAMPLE 36

[4-(4-Amino-phenyl)-oxazolo[5,4-c]pyridin-2-yl]-(3,4,5-trimethoxy-phenyl)-amine 0.082 g (0.209 mmol) (4-bromo-oxazolo[5,4-c]pyridin-2-yl)-(3,4,5-trimethoxy-phenyl)-amine and 0.04 g (0.22 mmol) (4-aminophenyl) boronic acid are dissolved in 3 ml 1,2-dimethoxy-ethane, a solution of 0.044 g (0.425 mmol) $Na_2CO_3$ (in 0.6 ml water) is added and a stream of argon is bubbled through the mixture in order to exclude oxygen from the reaction mixture. Tetrakis (triphenylphosphine) palladium (0.0259 g, 0.021 mmol) is added and the reaction mixture is stirred at 100° C. or 83 h. After that the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, hexane=>EtOAc) and recrystallisation from dichloromethane/diethyl ether to afford the title compound. $R_t$=1.70 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 393 $(M+1)^+$; m.p. 148-151° C.

The starting materials can be prepared as follows:

a) (4-Bromo-oxazolo[5,4-c]pyridin-2-yl)-(3,4,5-trimethoxy-phenyl)-amine 0.6 g (2.61 mmol) 4-bromo-2-methylsulfanyl-oxazolo[5,4-c]pyridine are heated to 100° C. until it liquefies, then 0.977 g (5.23 mmol) 3,4,5-trimethoxyanilin is added in small portions with stirring. Stirring is continued for 2 h. The reaction mixture is cooled to room temperature and purified by chromatography (silicagel, hexane=>EtOAc) to afford the title compound.

b) 4-Bromo-2-methylsulfanyl-oxazolo[5,4-c]pyridine

A mixture of 1.21 g (5.24 mmol) 4-bromo-oxazolo[5,4-c]pyridine-2-thiol, 0.8 g (5.76 mmol) $K_2CO_3$, 0.9 g (6.28 mmol) MeI in 12 ml DMF is stirred at room temperature for 1 h. The reaction mixture is then poured on water and extracted 2× with EtOAc. The combined organic layers are washed with water and saturated NaCl solution, dried over $MgSO_4$, filtered and the filtrate is concentrated in vacuo to afford the title compound in quantitative yield.

c) 4-Bromo-oxazolo[5,4-c]pyridine-2-thiol 1.34 g (7.09 mmol) 4-amino-2-bromo-pyridin-3-ol are dissolved in 13 ml EtOH and 1.86 g (11.3 mmol) potassium ethyl xanthogenate are added. This mixture is stirred for 18 h at reflux temperature. After cooling to room temperature, the reaction mixture is concentrated in vacuo and 5 ml water are added. With the addition of acetic acid, a pH of 5 is adjusted. The product starts to crystallize and is filtered off, washed 2× with water and dried to afford the title compound.

d) 4-Amino-2-bromo-pyridin-3-ol

A solution of 5.3 g (22.7 mmol) 2-bromo-4-nitro-pyridin-3-ol in 100 ml MeOH:THF=1:2 is hydrogenated in the presence of 0.5 g Pt/C (5%, Engelhard 4709). The reaction mixture is filtered (2 glass fiber filters used) and the filtrate is concentrated in vacuo to afford the crude title compound as a brown solid.

e) 2-Bromo-4-nitro-pyridin-3-ol

To a solution of 13 g (73.2 mmol) 2-bromo-3-pyridinol (Fluka 18292) in 40 ml of cone, sulfuric acid 5.1 ml (74 mmol) of nitric acid (65%) are added at 0° C. The reaction mixture is stirred at 0° C. for 12 h, then poured on water and extracted 2× with EtOAc. The combined organic layers are washed with water and saturated NaCl solution, dried over $MgSO_4$, filtered and the filtrate is concentrated in vacuo. The residue is purified by chromatography (silicagel, EtOAc) to afford 5.3 g of 2-bromo-4-nitro-pyridin-3-ol and 2 g of 2-bromo-6-nitro-pyridin-3-ol.

Using the same synthetic methods as described in Example 36, reaction of (4-bromo-oxazolo[5,4-c]pyridin-2-yl)-(3,4,5-trimethoxy-phenyl)-amine and the appropriate boronic acid derivative leads to the following examples:

EXAMPLE 37

[4-(3-Amino-phenyl)-oxazolo[5,4-c]pyridin-2-yl]-(3,4,5-trimethoxy-phenyl)-amine $R_t$=1.63 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 393 $(M+1)^+$; m.p. 120-126° C.

EXAMPLE 38

4-[2-(3,4,5-Trimethoxy-phenylamino)-oxazolo[5,4-c]pyridin-4-yl]-benzenesulfonamide $R_t$=1.71 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 457 $(M+1)^+$; m.p.>280° C.

Using the appropriately substituted isothiocyanate derivative in the synthetic methods described in example 1 (step b), the following derivatives are obtained:

EXAMPLE 39

[7-(3-Methoxy-phenyl)-benzooxazol-2-yl]-(4-morpholin-4-yl-phenyl)-amine. (from 4-morpholinophenyl-isothiocyanate)

$R_t$=2.14 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 402 $(M+1)^+$; m.p. 180-182° C.

EXAMPLE 40

[7-(4-Aminophenyl)-benzooxazol-2-yl]-(4-morpholin-4-yl-phenyl)-amine. (from 4-morpholinophenyl-isothiocyanate)

$R_t$=1.65 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 387 $(M+1)^+$; m.p. 241-243° C.

EXAMPLE 41

N-{4-[2-(4-Morpholin-4-yl-phenylamino)-benzooxazol-7-yl]-phenyl}-methane-sulfonamide. (from 4-morpholinophenyl-isothiocyanate)

$R_t$=1.94 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 387 $(M+1)^+$; m.p. 258-265° C.

EXAMPLE 42

[7-(3-Amino-phenyl)-benzooxazol-2-yl]-(6-morpholin-4-yl-pyridin-3-yl)-amine. (from 4-(5-Isothiocyanato-pyridin-2-yl)-morpholine)

$R_t$=1.576 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 388 $(M+1)^+$; m.p. 235-237° C.

The following compounds are prepared in analogy to the methods described herein:

EXAMPLE 43

[7-(3-Amino-phenyl)-benzooxazol-2-yl]-(4-morpholin-4-yl-phenyl)-amine

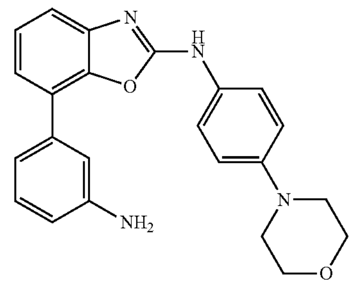 [SMILES: Nc1cccc(-c2cccc3nc(Nc4ccc(N5CCOCC5)cc4)oc23)c1]

$R_t$=1.66 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 387 $(M+1)^+$.

EXAMPLE 44

(7-o-Tolyl-benzooxazol-2-yl)-(3,4,5-trimethoxy-phenyl)-amine

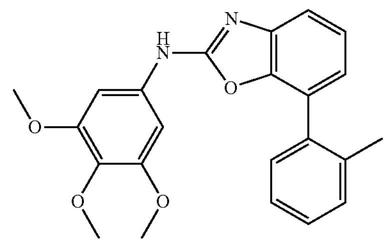

$R_t$=2.53 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 391 $(M+1)^+$.

EXAMPLE 45

3-[2-(3,4,5-Trimethoxy-phenylamino)-benzooxazol-7-yl]-benzonitrile

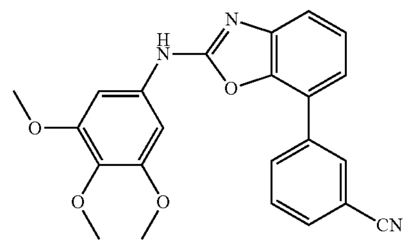 [SMILES: COc1cc(Nc2nc3cccc(-c4cccc(C#N)c4)c3o2)cc(OC)c1OC]

$R_t$=2.43 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 402 $(M+1)^+$.

EXAMPLE 46

(7-Pyridin-2-yl-benzooxazol-2-yl)-(3,4,5-trimethoxy-phenyl)-amine

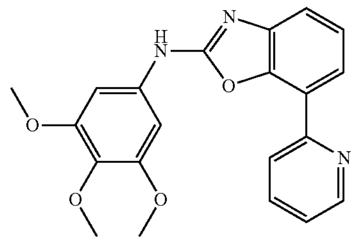 [SMILES: COc1cc(Nc2nc3cccc(-c4ccccn4)c3o2)cc(OC)c1OC]

$R_t$=1.87 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 378 $(M+1)^+$.

EXAMPLE 47

3-[2-(3,4,5-Trimethoxy-phenylamino)-benzooxazol-7-yl]-benzamide

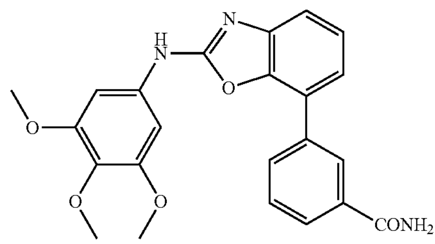 [SMILES: COc1cc(Nc2nc3cccc(-c4cccc(C(N)=O)c4)c3o2)cc(OC)c1OC]

$R_t$=2.12 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 420 $(M+1)^+$.

EXAMPLE 48

[7-(3-Nitro-phenyl)-benzooxazol-2-yl]-(3,4,5-trimethoxy-phenyl)-amine

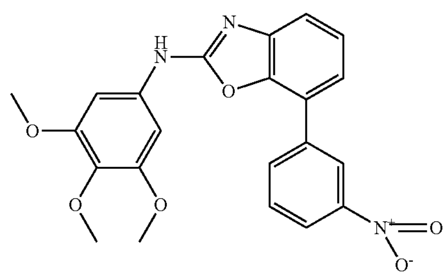 [SMILES: COc1cc(Nc2nc3cccc(-c4cccc([N+](=O)[O-])c4)c3o2)cc(OC)c1OC]

$R_t$=2.49 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 422 $(M+1)^+$.

EXAMPLE 49

[7-(3-Methanesulfonyl-phenyl)-benzooxazol-2-yl]-(3,4,5-trimethoxy-phenyl)-amine

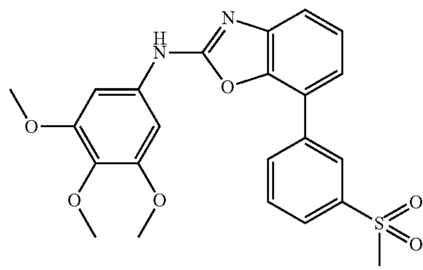 [SMILES: COc1cc(Nc2nc3cccc(-c4cccc(S(C)(=O)=O)c4)c3o2)cc(OC)c1OC]

$R_t$=2.28 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 455 $(M+1)^+$.

EXAMPLE 50

N-Methyl-3-[2-(3,4,5-trimethoxy-phenylamino)-benzooxazol-7-yl]-benzene-sulfonamide

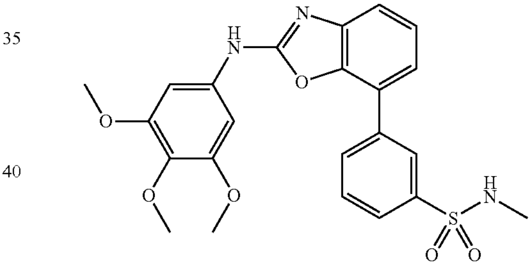

$R_t$=2.29 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 470 $(M+1)^+$.

EXAMPLE 51

[7-(4-Methoxy-3-nitro-phenyl)-benzooxazol-2-yl]-(3,4,5-trimethoxy-phenyl)-amine

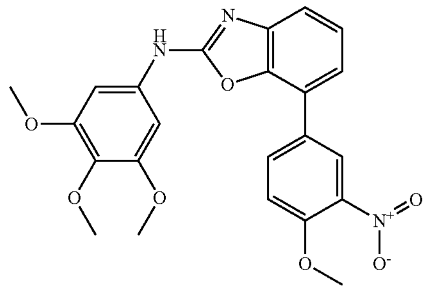 [SMILES: COc1ccc(-c2cccc3nc(Nc4cc(OC)c(OC)c(OC)c4)oc23)cc1[N+](=O)[O-]]

$R_t$=2.45 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 452 $(M+1)^+$.

EXAMPLE 52

[7-(3-Amino-4-chloro-phenyl)-benzooxazol-2-yl]-(3,4,5-trimethoxy-phenyl)-amine

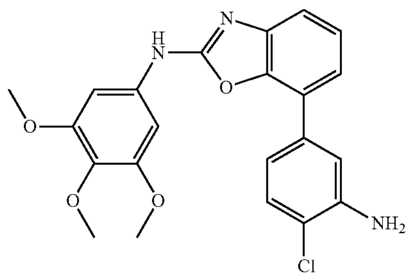 [SMILES: COc1cc(Nc2nc3cccc(-c4ccc(Cl)c(N)c4)c3o2)cc(OC)c1OC]

$R_t$=2.4 min (Waters Symmetry C8, 2.1×50 mm, detection 210-250 nM, 5% to 100% $CH_3CN$ in $H_2O$ in 2 min+0.05%, TFA, flow rate 1.0 ml/min); MS: 426 $(M+1)^+$.

EXAMPLE 53

[7-(3-Amino-4-methoxy-phenyl)-benzooxazol-2-yl]-(3,4,5-trimethoxy-phenyl)-amine

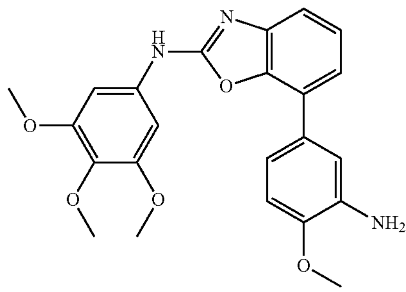 [SMILES: COc1ccc(-c2cccc3nc(Nc4cc(OC)c(OC)c(OC)c4)oc23)cc1N]

$R_t$=1.91 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 422 $(M+1)^+$.

EXAMPLE 54

[7-(4-Dimethylamino-phenyl)-benzooxazol-2-yl]-(3,4,5-trimethoxy-phenyl)-amine

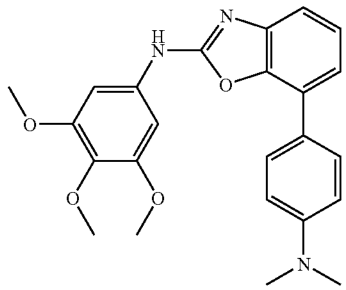

$R_t$=1.98 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 420 $(M+1)^+$.

EXAMPLE 55

N-{3-[2-(3,4,5-Trimethoxy-phenylamino)-benzooxazol-7-yl]-phenyl}-methanesulfonamide

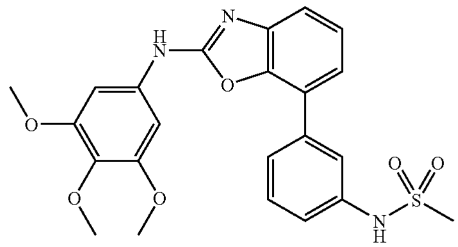

$R_t$=2.24 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 470 $(M+1)^+$.

The following Examples are prepared in analogy to the procedures described above:

EXAMPLE 56

N-(2-Methoxy-ethyl)-4-[7-(4-sulfamoyl-phenyl)-benzooxazol-2-ylamino]-benzamide

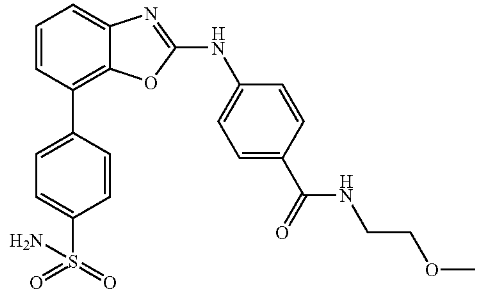 [SMILES: COCCNC(=O)c1ccc(Nc2nc3cccc(-c4ccc(S(N)(=O)=O)cc4)c3o2)cc1]

$R_t$=2.00 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 467 $(M+1)^+$.

EXAMPLE 57

N-(2-Dimethylamino-ethyl)-4-[7-(4-sulfamoyl-phenyl)-benzooxazol-2-ylamino]-benzamide

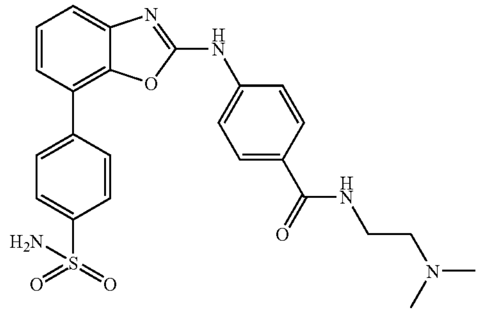 [SMILES: CN(C)CCNC(=O)c1ccc(Nc2nc3cccc(-c4ccc(S(N)(=O)=O)cc4)c3o2)cc1]

$R_t$=1.77 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 480 $(M+1)^+$.

EXAMPLE 58

4-[2-(3,4-Dimethoxy-phenylamino)-benzooxazol-7-yl]-benzenesulfonamide

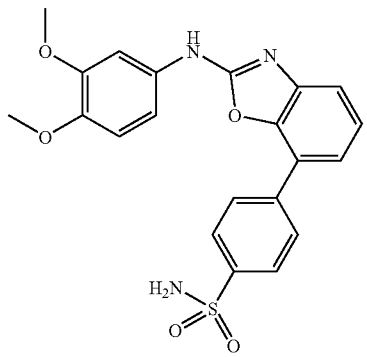 [SMILES: COc1ccc(Nc2nc3cccc(-c4ccc(S(N)(=O)=O)cc4)c3o2)cc1OC]

$R_t$=2.07 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 426 $(M+1)^+$.

EXAMPLE 59

4-[2-(3,4-Dimethoxy-phenylamino)-benzooxazol-7-yl]-N-methyl-benzenesulfonamide

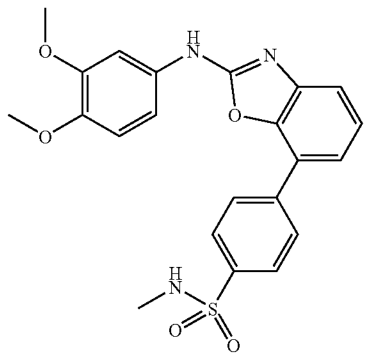 [SMILES: CNS(=O)(=O)c1ccc(-c2cccc3nc(Nc4ccc(OC)c(OC)c4)oc23)cc1]

$R_t$=2.19 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 440 $(M+1)^+$.

EXAMPLE 60

4-[2-(3,5-Dimethoxy-phenylamino)-benzooxazol-7-yl]-benzenesulfonamide

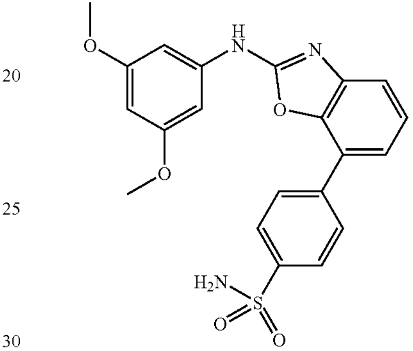

$R_t$=2.26 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 426 $(M+1)^+$.

EXAMPLE 61

N-Methyl-2-{4-[2-(3,4,5-trimethoxy-phenylamino)-benzooxazol-7-yl]-phenyl}-acetamide

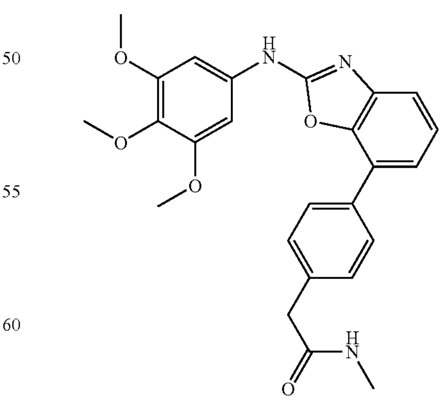

$R_t$=2.11 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 448 $(M+1)^+$.

EXAMPLE 62

N-{4-[2-(3,4,5-Trimethoxy-phenylamino)-oxazolo[5,4-c]pyridin-4-yl]-benzyl}-methanesulfonamide

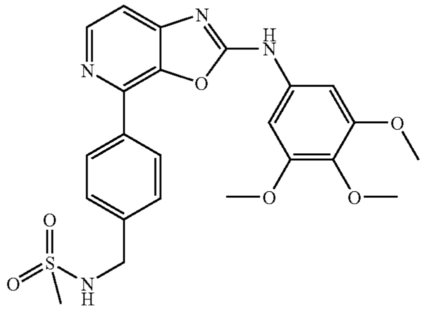 [SMILES: COc1cc(Nc2nc3ccnc(-c4ccc(CNS(C)(=O)=O)cc4)c3o2)cc(OC)c1OC]

$R_t$=1.73 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 485332 $(M+1)^+$.

EXAMPLE 63

[7-(4-Methanesulfinylmethyl-phenyl)-benzooxazol-2-yl]-(3,4,5-trimethoxy-phenyl)-amine

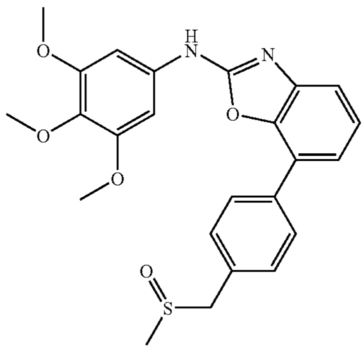 [SMILES: COc1cc(Nc2nc3cccc(-c4ccc(CS(C)=O)cc4)c3o2)cc(OC)c1OC]

$R_t$=2.08 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 453 $(M+1)^+$.

EXAMPLE 64

4-[7-(3-Fluoro-4-morpholin-4-ylmethyl-phenyl)-benzooxazol-2-ylamino]-2,N,N-trimethyl-benzamide

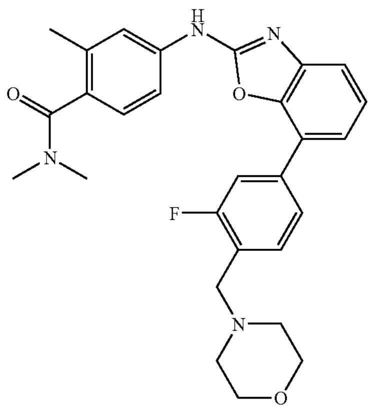 [SMILES: Cc1cc(Nc2nc3cccc(-c4ccc(CN5CCOCC5)c(F)c4)c3o2)ccc1C(=O)N(C)C]

0.1 g (0.267 mmol) 4-(7-bromo-benzooxazol-2-ylamino)-2,N,N-trimethyl-benzamide and 0.17 g (0.305 mmol) 4-(2- fluoro-4-trimethylstannanyl-benzyl)-morpholine are dissolved in 2 ml 1,2-dimethoxy-ethane and a stream of argon is bubbled through the mixture in order to exclude oxygen from the reaction mixture. Tetrakis (triphenylphosphine) palladium (0.020 g, 0.016 mmol) is added and the reaction mixture is stirred at 150° C. for 1 h. After that the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, EtOAc:MeOH=95:5; column chromatography followed by thick-layer chromatography) to afford the title compound. $R_t$=1.67 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 375 $(M+1)^+$.

Preparation of Starting Materials:

a) 4-(7-Bromo-benzooxazol-2-ylamino)-2,N,N-trimethyl-benzamide

To a solution of 0.49 g (2.01 mmol) 7-bromo-2-methylsulfanyl-benzooxazole in 30 ml dichloromethane, 3-chloroperbenzoic acid (0.494 g, 2.01 mmol) is added. This mixture is stirred for 1 h at room temperature. Then, 0.325 g (1.82 mmol) 4-amino-2,N,N-trimethyl-benzamide is added and the reaction mixture is heated to 40° C. with stirring continued for 20 h. The reaction mixture is concentrated in vacuo and the residue is purified by chromatography (silicagel, hexane:EtOAc=1:1=>1:4) to afford the title compound as an off-white crystalline solid.

b) 7-Bromo-2-methylsulfanyl-benzooxazole

A mixture of 6 g (26.1 mmol) 7-bromo-benzooxazole-2-thiol, 7.28 g (52.2 mmol) $K_2CO_3$, 4.1 g (28.7 mmol) MeI in 80 ml DMF is stirred at room temperature for 1 h. The reaction mixture is then poured on water and extracted 2× with EtOAc. The combined organic layers are washed with water and saturated NaCl solution, dried over $MgSO_4$, filtered and the filtrate is concentrated in vacuo to afford the title compound.

c) 7-Bromo-benzooxazole-2-thiol 5 g (26.6 mmol) 2-amino-6-bromo-phenol are dissolved in 20 ml EtOH and 6.52 g (39.9 mmol) potassium ethyl xanthogenate are added. This mixture is stirred for 6 h at reflux temperature. After cooling to room temperature, the reaction mixture is concentrated in vacuo and 50 ml water are added. With the addition of acetic acid, a pH of 5 is adjusted. The product starts to crystallize and is filtered off, washed 2× with water and dried to afford the title compound.

d) 2-Amino-6-bromo-phenol

A solution of 5.3 g (22.7 mmol) 2-bromo-6-nitro-phenol in 100 ml MeOH:THF=1:1 is hydrogenated in the presence of 0.2 g Ra—Ni (in EtOH, Degussa B113W). The reaction mixture is filtered (2 glass fiber filters used) and the filtrate is concentrated in vacuo to afford the crude title compound.

f) 4-Amino-2,N,N-trimethyl-benzamide

A solution of 1.7 g (8.16 mmol) 2,N,N-trimethyl-4-nitrobenzamide in 45 ml MeOH:THF=1:1 is hydrogenated in the presence of 0.2 g 10% Pd/C (Fluka 75990). The reaction mixture is filtered (2 glass fiber filters used) and the filtrate is concentrated in vacuo to afford the crude title compound.

g) 2,N,N-Trimethyl-4-nitro-benzamide

A solution of 2 g (10.7 mmol) 2-methyl-4-nitro-benzoic acid, 1.32 ml (11.8 mmol) N-methyl-morpholine, 2.36 g (12 mmol) EDC-HCl and 2.36 g (12 mmol) HOBt in 50 ml dichloromethane is stirred at RT for 45 min, then dimethylamine solution (5.9 ml, 33% in EtOH) is added and the reaction mixture is heated to 40° C. and stirred at this temperature for 20 h. Another 1.32 ml (11.8 mmol) N-methyl-morpholine, 2.36 g (12 mmol) EDC-HCl and 2.36 g (12 mmol) HOBt (hydroxyl-benzotriazole) are added and stirred for 45 min, the again dimethylamine solution (5.9 ml, 33% in EtOH) is added and the reaction mixture is stirred at 40° C. for 35 h. After that the reaction mixture is cooled to RT and poured onto EtOAc/water. The organic layer is washed with sat. $NAHCO_3$ solution and with water, dried over $MgSO_4$, filtered and the filtrate is concentrated in vacuo. The residue is purified by chromatography (silicagel, hexane:EtOAc=1:1=>EtOAc) to afford the title compound as a yellowish oil.

h) 4-(2-Fluoro-4-trimethylstannanyl-benzyl)-morpholine

A solution of 1 g (3.65 mmol) 4-(4-bromo-2-fluoro-benzyl)-morpholine and 0.95 ml (4.56 mmol) hexamethylditin in 15 ml toluene is prepared and a stream of argon is bubbled through the mixture in order to exclude oxygen from the reaction mixture. Tetrakis (triphenylphosphine) palladium (0.221 g, 0.185 mmol) is added and the reaction mixture is stirred at 110° C. for 5 h. The reaction mixture is allowed to cool to RT and is filtered through a layer of Hyflo. The filtrate is concentrated in vacuo and further dried under high vacuum for 20 h to afford the title compound as a yellowish oil.

EXAMPLE 65

4-{7-[4-(1,1-Dioxo-thiomorpholin-4-ylmethyl)-3,5-difluoro-phenyl]-benzooxazol-2-ylamino}-2,N,N-trimethyl-benzamide

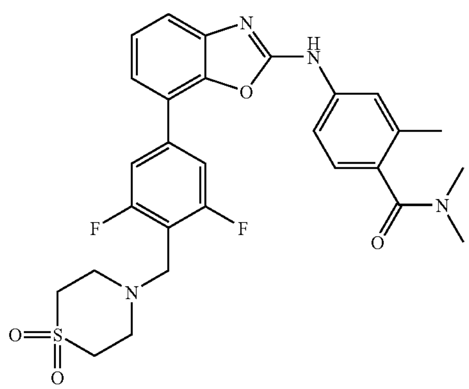 [SMILES: Cc1cc(Nc2nc3cccc(-c4cc(F)c(CN5CCS(=O)(=O)CC5)c(F)c4)c3o2)ccc1C(=O)N(C)C]

A solution of 0.1 g (0.267 mmol) 4-(7-bromo-benzooxazol-2-ylamino)-2,N,N-trimethyl-benzamide, 0.114 g (0.294 mmol) 4-[2,6-difluoro-4-(4,4,5,5-tetramethyl-[1,3,2]dioxaborolan-2-yl)-benzyl]-thiomorpholine 1,1-dioxid and 174 mg $K_3PO_4$ are dissolved in 5 ml 1,2-dimethoxy-ethane, water (0.1 ml) is added and a stream of argon is bubbled through the mixture in order to exclude oxygen from the reaction mixture. Tetrakis (triphenylphosphine) palladium (0.0095 g, 0.0082 mmol) is added and the reaction mixture is stirred at 100° C. for 8 h. After that the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, EtOAc), followed by recrystallisation diethylether/methanol to afford the title compound as white crystals. $R_t$=2.13 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 555 $(M+1)^+$.

Preparation of Starting Materials:

a) 4-[2,6-difluoro-4-(4,4,5,5-tetramethyl-[1,3,2]dioxaborolan-2-yl)-benzyl]-thiomorpholine 1,1-dioxide A solution (degassed with argon) of 1.02 g (3.0 mmol) 4-(4-bromo-2,6-difluoro-benzyl)-thiomorpholine 1,1-dioxide in 4 ml dimethylacetamide is added to a solution (degassed with argon) of 0.855 g (3.3 mmol) bis-(pinacolato)-diboron and 0.594 g (6.0 mmol) dried KOAc in 4 ml dimethylacetamide. After that 0.076 g (0.092 mmol) $Pd(dppf)Cl_2$—$CH_2Cl_2$ is added. The reaction mixture is heated to 80° C. and stirred at this temperature for 4 h. Then the reaction mixture is cooled to room temperature and poured on water and extracted 3× with EtOAc. The combined organic layers are washed with water and saturated NaCl solution, dried over $MgSO_4$, filtered and the filtrate is concentrated in vacuo to afford the title compound as a dark brown oil.

Note: in some cases, (partial) hydrolysis to the free boronic acid derivative occurs, however, this is no problem as the free boronic acid (or a mixture of free boronic acid with the tetramethyl[1,3,2]dioxaborolane derivative work equally well in the Suzuki coupling reaction.

b) 4-(4-Bromo-2,6-difluoro-benzyl)-thiomorpholine 1,1-dioxide

A solution of 3.8 g (11.3 mmol) 5-bromo-2-bromomethyl-1,3-difluoro-benzene, 1.83 g (13.6 mmol) thiomorpholine dioxide and 1.88 ml (13.6 mmol) triethylamine in 40 ml dichloromethane is stirred at room temperature for 20 h. Then the reaction mixture is poured on water and extracted 3× with EtOAc. The combined organic layers are washed with water and saturated NaCl solution, dried over $MgSO_4$, filtered and the filtrate is concentrated in vacuo. The residue is taken up in diethylether, vigorously stirred, and the title compound is obtained after filtration as a white crystalline solid.

c) 5-Bromo-2-bromomethyl-1,3-difluoro-benzene

To a cooled (0° C.) solution of 4 g (17.6 mmol) 4-bromo-2,6-difluorobenzyl alcohol in 50 ml THF, 7 g (26.4 mmol) triphenylphosphine and 8.83 g (26.4 mmol) carbon tetrabromide are added with stirring. Stirring is continued for 10 min at 0° C. and for 1 h at room temperature. After that the reaction mixture is filtered and the filtrate is concentrated in vacuo. The residue is purified by chromatography (silicagel, hexane) to afford the title compound as yellowish oil.

EXAMPLE 66

[4-(2-{4-[4-(2-Methoxy-ethyl)-piperazin-1-yl]-3-methyl-phenylamino}-benzooxazol-7-yl)-2-methyl-phenyl]-morpholin-4-yl-methanone

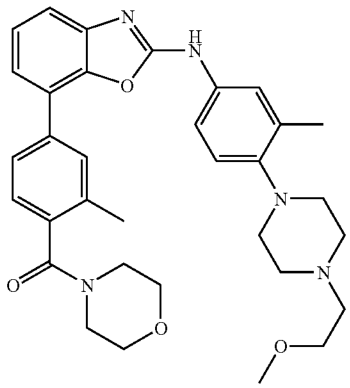 [SMILES: COCCN1CCN(c2ccc(Nc3nc4cccc(-c5ccc(C(=O)N6CCOCC6)c(C)c5)c4o3)cc2C)CC1]

The title compound is prepared from (7-bromo-benzooxazol-2-yl)-{4-[4-(2-methoxy-ethyl)-piperazin-1-yl]-3-methyl-phenyl}-amine and [2-methyl-4-(4,4,5,5-tetramethyl-[1,3,2]dioxa-borolan-2-yl)-phenyl]-morpholin-4-yl-methanone using methodology described in the preparation of example 65. The title compound is obtained as an off-white foam. $R_t$=2.00 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 570 $(M+1)^+$.

Preparation of Starting Materials:

a) (7-Bromo-benzooxazol-2-yl)-{4-[4-(2-methoxy-ethyl)-piperazin-1-yl]-3-methyl-phenyl}-amine The title compound is prepared from 4-[4-(2-methoxy-ethyl)-piperazin-1-yl]-3-methyl-phenylamine and 7-bromo-2-methylsulfanyl-benzooxazole using methodology described in the preparation of example 64.

b) 4-[4-(2-Methoxy-ethyl)-piperazin-1-yl]-3-methyl-phenylamine

A solution of 0.85 g (3.04 mmol) 1-(2-methoxy-ethyl)-4-(2-methyl-4-nitro-phenyl)-piperazine in 20 ml MeOH:THF=1:1 is hydrogenated in the presence of 0.2 g 10% Pd/C (Engelhard 4505). The reaction mixture is filtered (2 glass fiber filters used) and the filtrate is concentrated in vacuo to afford the title compound as an oil.

c) 1-(2-Methoxy-ethyl)-4-(2-methyl-4-nitro-phenyl)-piperazine

A solution of 0.95 g (6.06 mmol) 2-fluoro-5-nitrotoluene and 0.99 g (6.67 mmol) 1-(2-methoxyethyl)piperazine in 10 ml dimethylacetamide is stirred at 120° C. for 20 h. After that the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, EtOAc) to afford the title compound as an oil.

d) (4-Bromo-2-methyl-phenyl)-morpholin-4-yl-methanone

A solution of 10.6 ml (47 mmol) oxalyl chloride in 30 ml dichloromethane is added dropwise to a iced-cooled solution of 5.21 g (23.5 mmol) 4-bromo-2-methyl-benzoic acid and 0.0087 ml DMF in 100 ml $CH_2Cl_2$. After complete addition, the cooling bath is removed and stirring maintained for 2 h at RT. The solvent is evaporated to dryness and the residue is dried in vacuo and dissolved in 100 ml dichloromethane and 8.21 ml N-ethyl-diisopropylamine is added. To this solution 2.5 ml (28 mmol) morpholine is added slowly. Stirring is continued for 0.5 h, then the reaction mixture is poured on water and extracted 3× with EtOAc. The combined organic layers are washed with water and saturated NaCl solution, dried over $MgSO_4$, filtered and the filtrate is concentrated in vacuo to afford the title compound which is used in the next step without further purification.

e) [2-Methyl-4-(4,4,5,5-tetramethyl-[1,3,2]dioxaborolan-2-yl)-phenyl]-morpholin-4-yl-methanone A solution (degassed with argon) of 3.0 g (10.6 mmol) (4-bromo-2-methyl-phenyl)-morpholin-4-yl-methanone in 15 ml dimethylacetamide is added to a solution (degassed with argon) of 3.01 g (11.6 mmol) bis-(pinacolato)-diboron and 2.09 g (21.1 mmol) dried KOAc in 15 ml dimethylacetamide. After that 0.261 g (0.317 mmol) $Pd(dppf)Cl_2$—$CH_2Cl_2$ is added. The reaction mixture is heated to 80° C. and stirred at this temperature for 4 h. After that the reaction mixture is cooled to room temperature and poured on water and extracted 3× with EtOAc. The combined organic layers are washed with water and saturated NaCl solution, dried over $MgSO_4$, filtered and the filtrate is concentrated in vacuo and further dried under high vacuum to afford the title compound as a dark brown oil.

Using the reaction conditions described for the preparation of the previously listed examples, especially as described in examples 64, 65 and 66, the following examples can be prepared. The starting materials are either commercially available or can be prepared from commercially available reagents using synthetic methodology as described in "preparation of starting materials" of examples 64, 65 and 66:

EXAMPLE 67

{4-[7-(3-Fluoro-4-morpholin-4-ylmethyl-phenyl)-benzooxazol-2-ylamino]-2-methyl-phenyl}-pyrrolidin-1-yl-methanone

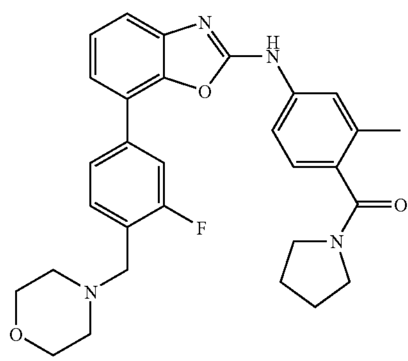 [SMILES: Cc1cc(Nc2nc3cccc(-c4ccc(CN5CCOCC5)c(F)c4)c3o2)ccc1C(=O)N1CCCC1]

$R_t$=1.96 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 515 $(M+1)^+$.

EXAMPLE 68

4-[7-(3,5-Difluoro-4-morpholin-4-ylmethyl-phenyl)-benzooxazol-2-ylamino]-2,N,N-trimethyl-benzamide

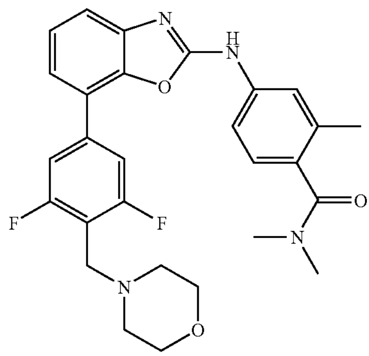 [SMILES: Cc1cc(Nc2nc3cccc(-c4cc(F)c(CN5CCOCC5)c(F)c4)c3o2)ccc1C(=O)N(C)C]

$R_t$=1.90 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 507 $(M+1)^+$.

EXAMPLE 69

2,N,N-Trimethyl-4-{7-[4-(morpholine-4-carbonyl)-phenyl]-benzooxazol-2-ylamino}-benzamide

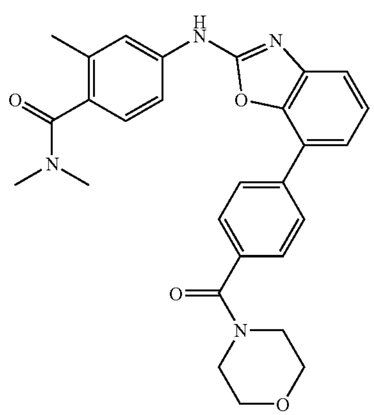 [SMILES: Cc1cc(Nc2nc3cccc(-c4ccc(C(=O)N5CCOCC5)cc4)c3o2)ccc1C(=O)N(C)C]

$R_t$=1.87 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 485 $(M+1)^+$.

EXAMPLE 70

2,N,N-Trimethyl-4-{7-[4-(2-morpholin-4-yl-2-oxo-ethyl)-phenyl]-benzooxazol-2-ylamino}-benzamide

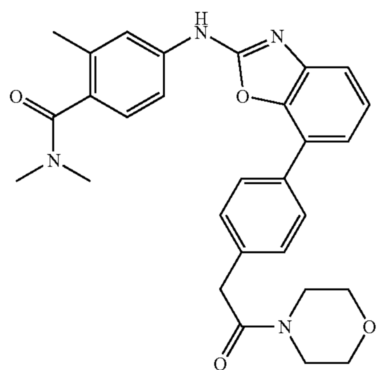 [SMILES: Cc1cc(Nc2nc3cccc(-c4ccc(CC(=O)N5CCOCC5)cc4)c3o2)ccc1C(=O)N(C)C]

$R_t$=1.896 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 499 $(M+1)^+$.

EXAMPLE 71

4-[7-(4-Methanesulfonylmethyl-phenyl)-benzooxazol-2-ylamino]-N,N-dimethyl-benzamide

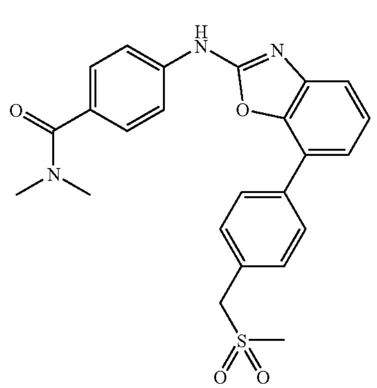 [SMILES: CN(C)C(=O)c1ccc(Nc2nc3cccc(-c4ccc(CS(C)(=O)=O)cc4)c3o2)cc1]

$R_t$=1.89 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 450 $(M+1)^+$.

EXAMPLE 72

2-(4-{2-[3-Methyl-4-(4-methyl-piperazine-1-carbonyl)-phenylamino]-benzooxazol-7-yl}-phenyl)-1-morpholin-4-yl-ethanone

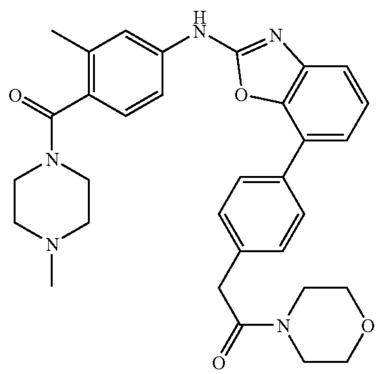 [SMILES: Cc1cc(Nc2nc3cccc(-c4ccc(CC(=O)N5CCOCC5)cc4)c3o2)ccc1C(=O)N1CCN(C)CC1]

$R_t$=1.855 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 554 $(M+1)^+$.

EXAMPLE 73

2-(2-Fluoro-4-{2-[3-methyl-4-(4-methyl-piperazine-1-carbonyl)-phenylamino]-benzooxazol-7-yl}-phenyl)-1-morpholin-4-yl-ethanone

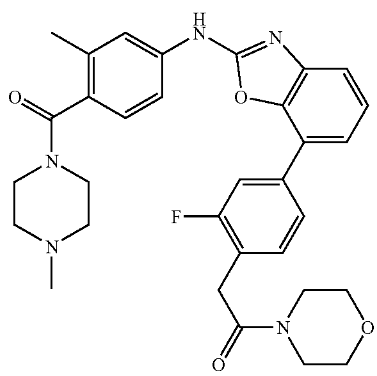 [SMILES: Cc1cc(Nc2nc3cccc(-c4ccc(CC(=O)N5CCOCC5)c(F)c4)c3o2)ccc1C(=O)N1CCN(C)CC1]

$R_t$=1.697 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 572 $(M+1)^+$.

EXAMPLE 74

2-(4-{2-[4-(4-Methyl-piperazin-1-yl)-phenylamino]-benzooxazol-7-yl}-phenyl)-1-morpholin-4-yl-ethanone

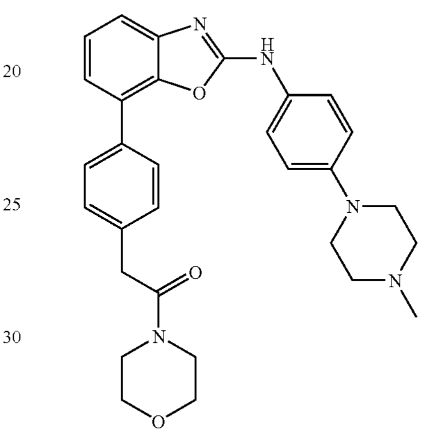

$R_t$=1.65 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 512 $(M+1)^+$.

EXAMPLE 75

(2-Fluoro-4-{2-[4-(4-methyl-piperazin-1-yl)-phenylamino]-benzooxazol-7-yl}-phenyl)-morpholin-4-yl-methanone

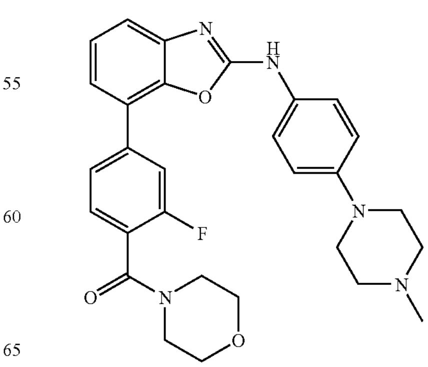

$R_t$=1.90 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 516 $(M+1)^+$.

EXAMPLE 76

4-{7-[2-Fluoro-4-(morpholine-4-carbonyl)-phenyl]-benzooxazol-2-ylamino}-2,N,N-trimethyl-benzamide

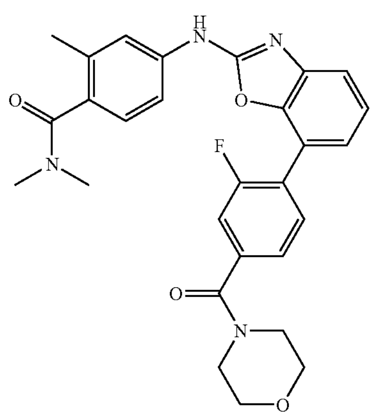 [SMILES: Cc1cc(Nc2nc3cccc(-c4ccc(C(=O)N5CCOCC5)cc4F)c3o2)ccc1C(=O)N(C)C]

$R_t$=1.892 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 503 $(M+1)^+$.

EXAMPLE 77

4-(7-{4-[2-(1,1-Dioxo-1lambda*6*-thiomorpholin-4-yl)-2-oxo-ethyl]-phenyl}-benzooxazol-2-ylamino)-2, N,N-trimethyl-benzamide

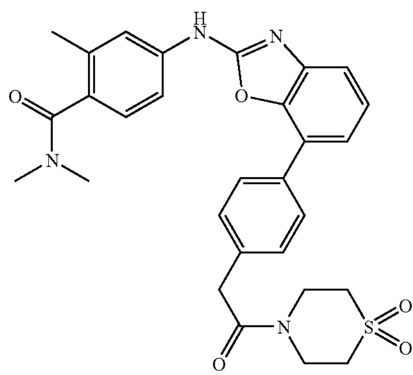 [SMILES: Cc1cc(Nc2nc3cccc(-c4ccc(CC(=O)N5CCS(=O)(=O)CC5)cc4)c3o2)ccc1C(=O)N(C)C]

$R_t$=1.88 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 547 $(M+1)^+$.

EXAMPLE 78

4-{7-[3-Fluoro-4-(morpholine-4-carbonyl)-phenyl]-benzooxazol-2-ylamino}-2, N,N-trimethyl-benzamide

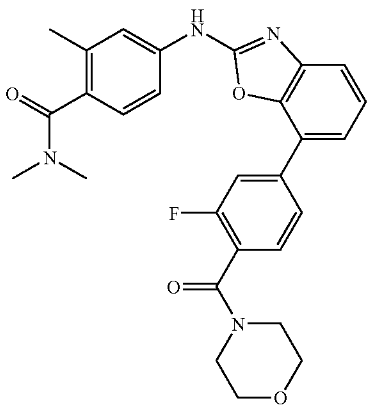 [SMILES: Cc1cc(Nc2nc3cccc(-c4ccc(C(=O)N5CCOCC5)c(F)c4)c3o2)ccc1C(=O)N(C)C]

$R_t$=1.935 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 503 $(M+1)^+$.

EXAMPLE 79

4-{7-[4-(1,1-Dioxo-1lambda*6*-thiomorpholin-4-ylmethyl)-phenyl]-benzooxazol-2-ylamino}-2,N,N-trimethyl-benzamide

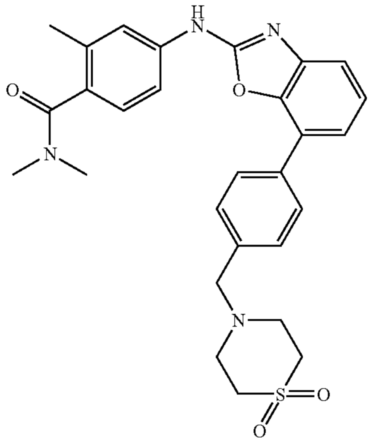 [SMILES: Cc1cc(Nc2nc3cccc(-c4ccc(CN5CCS(=O)(=O)CC5)cc4)c3o2)ccc1C(=O)N(C)C]

$R_t$=1.71 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 519 $(M+1)^+$.

EXAMPLE 80

(1,1-Dioxo-1lambda*6*-thiomorpholin-4-yl)-(2-fluoro-4-{2-[4-(4-methyl-piperazin-1-yl)-phenylamino]-benzooxazol-7-yl}-phenyl)-methanone

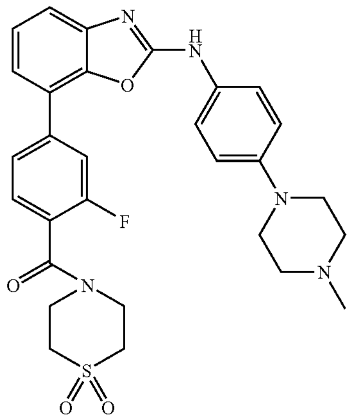 [SMILES: CN1CCN(c2ccc(Nc3nc4cccc(-c5ccc(C(=O)N6CCS(=O)(=O)CC6)c(F)c5)c4o3)cc2)CC1]

$R_t$=1.64 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 564 $(M+1)^+$.

EXAMPLE 81

4-[7-(4-Methanesulfinylmethyl-phenyl)-benzooxazol-2-ylamino]-2,N,N-trimethyl-benzamide

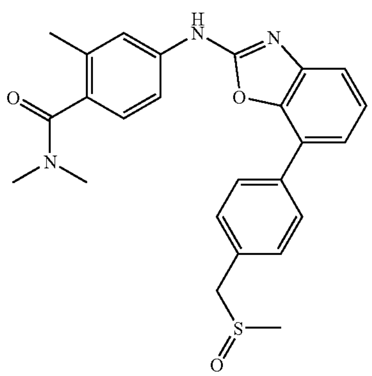 [SMILES: Cc1cc(Nc2nc3cccc(-c4ccc(CS(C)=O)cc4)c3o2)ccc1C(=O)N(C)C]

$R_t$=1.79 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 448 $(M+1)^+$.

EXAMPLE 82

(2-Methyl-4-{2-[4-(4-methyl-piperazin-1-yl)-phenylamino]-benzooxazol-7-yl}-phenyl)-morpholin-4-yl-methanone

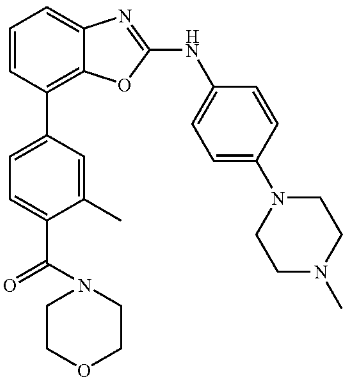 [SMILES: Cc1cc(-c2cccc3nc(Nc4ccc(N5CCN(C)CC5)cc4)oc23)ccc1C(=O)N1CCOCC1]

$R_t$=1.88 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 512 $(M+1)^+$.

EXAMPLE 83

4-(7-{4-[2-(1,1-Dioxo-1lambda*6*-thiomorpholin-4-yl)-2-oxo-ethyl]-3-fluoro-phenyl}-benzooxazol-2-ylamino)-2,N,N-trimethyl-benzamide

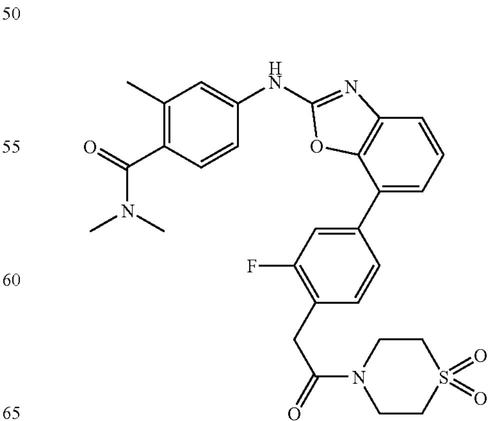

$R_t$=1.924 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 565 $(M+1)^+$.

EXAMPLE 84

4-{7-[4-(1,1-Dioxo-1lambda*6*-thiomorpholin-4-ylmethyl)-3-fluoro-phenyl]-benzooxazol-2-ylamino}-2,N,N-trimethyl-benzamide

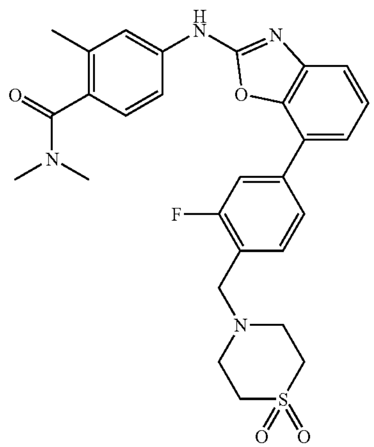 [SMILES: Cc1cc(Nc2nc3cccc(-c4ccc(CN5CCS(=O)(=O)CC5)c(F)c4)c3o2)ccc1C(=O)N(C)C]

$R_t$=1.786 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 537 $(M+1)^+$.

EXAMPLE 85

2,N,N-Trimethyl-4-{7-[3-methyl-4-(morpholine-4-carbonyl)-phenyl]-benzooxazol-2-ylamino}-benzamide

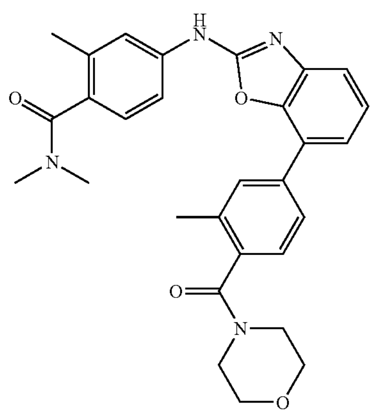 [SMILES: Cc1cc(Nc2nc3cccc(-c4ccc(C(=O)N5CCOCC5)c(C)c4)c3o2)ccc1C(=O)N(C)C]

$R_t$=1.914 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 499 $(M+1)^+$.

EXAMPLE 86

2,N,N-Trimethyl-4-[7-(4-morpholin-4-ylmethyl-3-trifluoromethyl-phenyl)-benzooxazol-2-ylamino]-benzamide

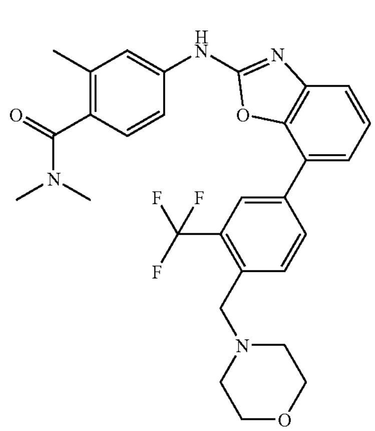 [SMILES: Cc1cc(Nc2nc3cccc(-c4ccc(CN5CCOCC5)c(C(F)(F)F)c4)c3o2)ccc1C(=O)N(C)C]

$R_t$=1.75 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 539 $(M+1)^+$.

EXAMPLE 87

[4-(4-Ethyl-piperazin-1-yl)-3-methyl-phenyl]-[7-(3-fluoro-4-morpholin-4-ylmethyl-phenyl)-benzooxazol-2-yl]-amine

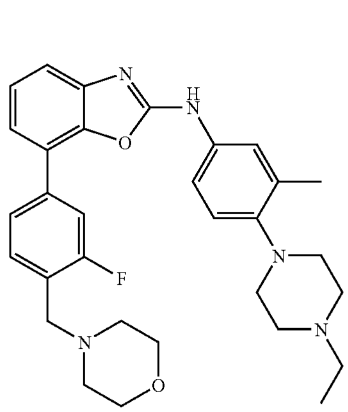 [SMILES: CCN1CCN(c2ccc(Nc3nc4cccc(-c5ccc(CN6CCOCC6)c(F)c5)c4o3)cc2C)CC1]

$R_t$=1.57 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 530 $(M+1)^+$.

EXAMPLE 88

{7-[4-(1,1-Dioxo-1lambda*6*-thiomorpholin-4-ylmethyl)-3-fluoro-phenyl]-benzooxazol-2-yl}-[4-(4-ethyl-piperazin-1-yl)-3-methyl-phenyl]-amine

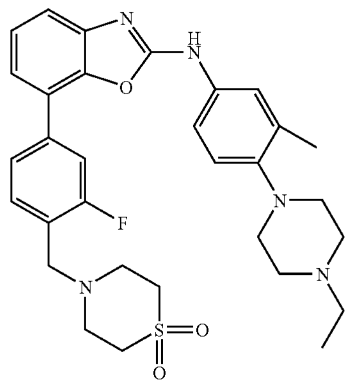 [SMILES: CCN1CCN(c2ccc(Nc3nc4cccc(-c5ccc(CN6CCS(=O)(=O)CC6)c(F)c5)c4o3)cc2C)CC1]

$R_t$=1.64 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 578 $(M+1)^+$.

EXAMPLE 89

{7-[4-(1,1-Dioxo-1lambda*6*-thiomorpholin-4-ylmethyl)-phenyl]-benzooxazol-2-yl}-[4-(4-methyl-piperazin-1-yl)-phenyl]-amine

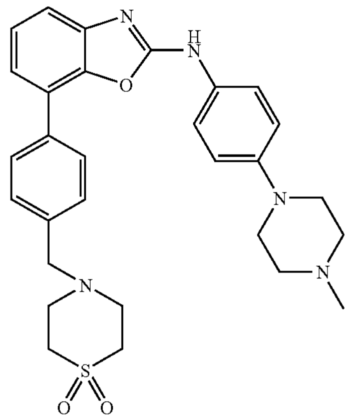 [SMILES: CN1CCN(c2ccc(Nc3nc4cccc(-c5ccc(CN6CCS(=O)(=O)CC6)cc5)c4o3)cc2)CC1]

$R_t$=1.52 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 532 $(M+1)^+$.

EXAMPLE 90

5-{7-[3-Fluoro-4-(morpholine-4-caronyl)-phenyl]-benzooxazol-2-ylamino}-2-(4-methyl-piperazin-1-yl)-benzonitrile

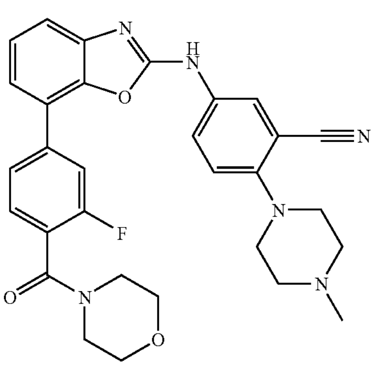 [SMILES: CN1CCN(c2ccc(Nc3nc4cccc(-c5ccc(C(=O)N6CCOCC6)c(F)c5)c4o3)cc2C#N)CC1]

$R_t$=1.76 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 1.76 $(M+1)^+$.

EXAMPLE 91

{2-Fluoro-4-[2-(4-piperazin-1-yl-phenylamino)-benzooxazol-7-yl]-phenyl}-morpholin-4-yl-methanone

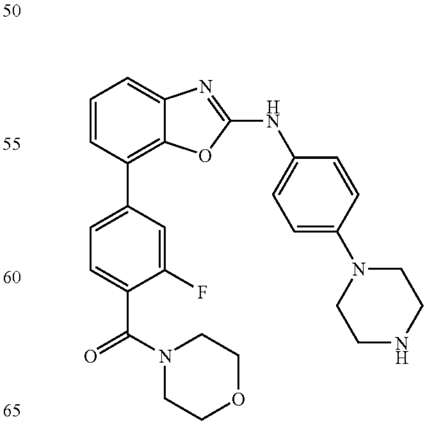

$R_t$=1.89 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 502 $(M+1)^+$.

EXAMPLE 92

[4-(4-Ethyl-piperazin-1-yl)-3-methyl-phenyl]-[7-(4-methanesulfonyl-phenyl)-benzooxazol-2-yl]-amine

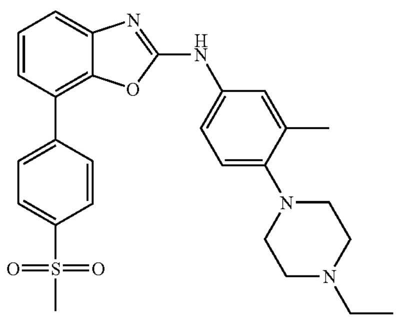 [SMILES: CCN1CCN(c2ccc(Nc3nc4cccc(-c5ccc(S(C)(=O)=O)cc5)c4o3)cc2C)CC1]

$R_t$=2.00 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 491 $(M+1)^+$.

EXAMPLE 93

4-{2-[4-(4-Methyl-piperazin-1-yl)-phenylamino]-benzooxazol-7-yl}-benzenesulfonamide

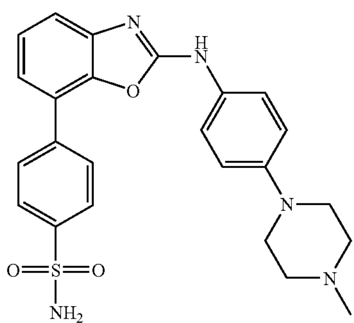 [SMILES: CN1CCN(c2ccc(Nc3nc4cccc(-c5ccc(S(N)(=O)=O)cc5)c4o3)cc2)CC1]

$R_t$=1.81 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 464 $(M+1)^+$.

EXAMPLE 94

(4-{2-[4-(4-Ethyl-piperazin-1-yl)-3-methyl-phenylamino]-benzooxazol-7-yl}-2-fluoro-phenyl)-morpholin-4-yl-methanone

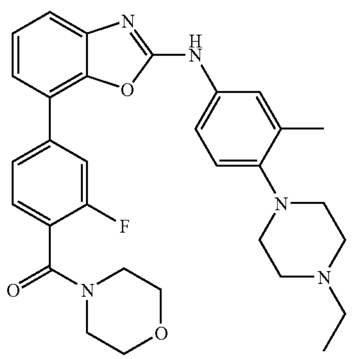 [SMILES: CCN1CCN(c2ccc(Nc3nc4cccc(-c5ccc(C(=O)N6CCOCC6)c(F)c5)c4o3)cc2C)CC1]

$R_t$=2.00 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 544 $(M+1)^+$.

EXAMPLE 95

{7-[4-(1,1-Dioxo-1lambda*6*-thiomorpholin-4-ylmethyl)-3,5-difluoro-phenyl]-benzooxazol-2-yl}-[4-(4-methyl-piperazin-1-yl)-phenyl]-amine

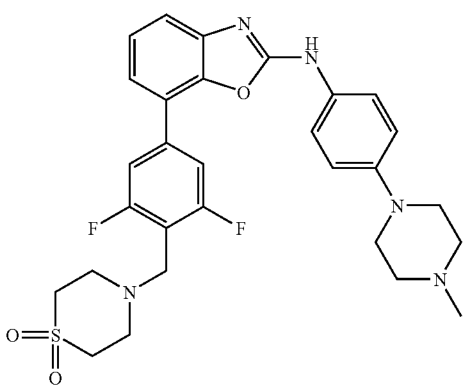 [SMILES: CN1CCN(c2ccc(Nc3nc4cccc(-c5cc(F)c(CN6CCS(=O)(=O)CC6)c(F)c5)c4o3)cc2)CC1]

$R_t$=1.50 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 568 $(M+1)^+$.

EXAMPLE 96

(4-{7-[4-(1,1-Dioxo-1lambda*6*-thiomorpholin-4-ylmethyl)-3,5-difluoro-phenyl]-benzooxazol-2-ylamino}-2-methyl-phenyl)-pyrrolidin-1-yl-methanone

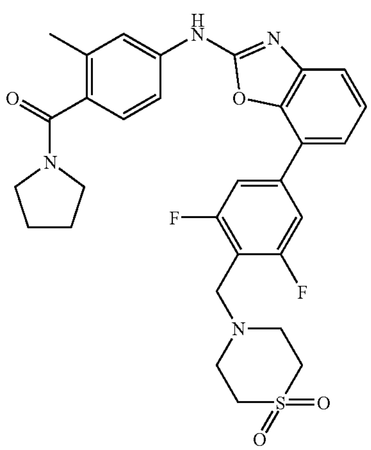 [SMILES: Cc1cc(Nc2nc3cccc(-c4cc(F)c(CN5CCS(=O)(=O)CC5)c(F)c4)c3o2)ccc1C(=O)N1CCCC1]

$R_t$=2.20 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 581 $(M+1)^+$.

EXAMPLE 97

(4-{2-[4-(4-Cyclopropyl-piperazin-1-yl)-phenylamino]-benzooxazol-7-yl}-2-methyl-phenyl)-morpholin-4-yl-methanone

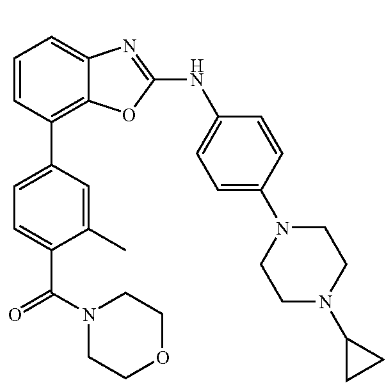 [SMILES: Cc1cc(-c2cccc3nc(Nc4ccc(N5CCN(C6CC6)CC5)cc4)oc23)ccc1C(=O)N1CCOCC1]

$R_t$=2.00 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 538 $(M+1)^+$.

EXAMPLE 98

[7-(3,5-Difluoro-4-morpholin-4-ylmethyl-phenyl)-benzooxazol-2-yl]-[4-(4-ethyl-piperazin-1-yl)-3-methyl-phenyl]-amine

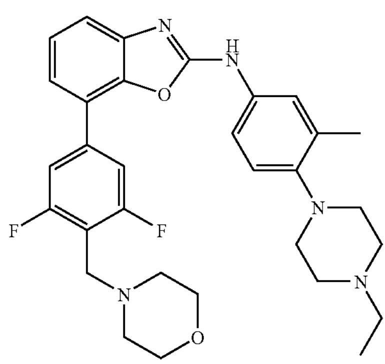

$R_t$=1.58 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 548 $(M+1)^+$.

EXAMPLE 99

{4-[7-(3,5-Difluoro-4-morpholin-4-ylmethyl-phenyl)-benzooxazol-2-ylamino]-2-methyl-phenyl}-pyrrolidin-1-yl-methanone

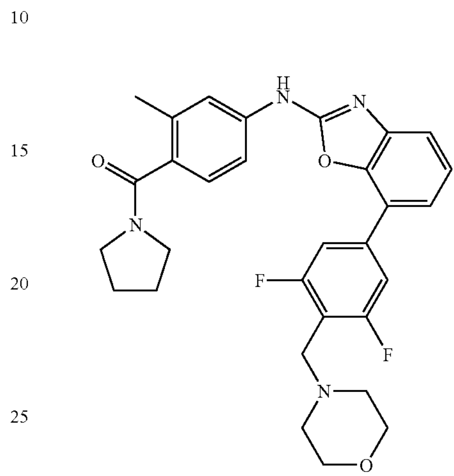

$R_t$=1.96 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 533 $(M+1)^+$.

EXAMPLE 100

{4-[4-(2-Dimethylamino-ethyl)-piperazin-1-yl]-3-methyl-phenyl}-[7-(4-methanesulfonyl-phenyl)-benzooxazol-2-yl]-amine

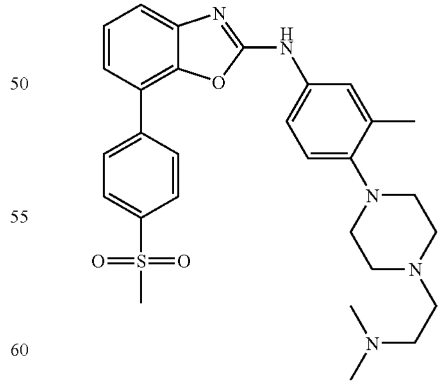

$R_t$=1.86 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 534 $(M+1)^+$.

EXAMPLE 101

{7-[4-(1,1-Dioxo-1lambda*6*-thiomorpholin-4-ylmethyl)-3,5-difluoro-phenyl]-benzooxazol-2-yl}-[4-(4-isopropyl-piperazin-1-yl)-3-methyl-phenyl]-amine

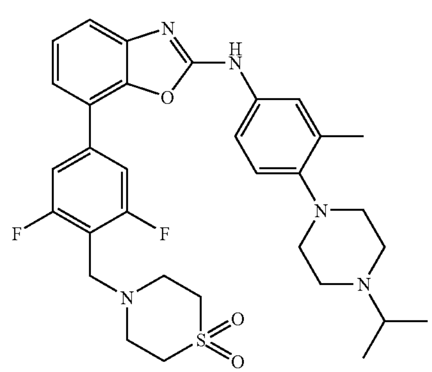 [SMILES: Cc1cc(Nc2nc3cccc(-c4cc(F)c(CN5CCS(=O)(=O)CC5)c(F)c4)c3o2)ccc1N1CCN(C(C)C)CC1]

$R_t$=2.02 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 610 $(M+1)^+$.

EXAMPLE 102

[4-(2-{4-[4-(2-Dimethylamino-ethyl)-piperazin-1-yl]-3-methyl-phenylamino}-benzooxazol-7-yl)-2-methyl-phenyl]-morpholin-4-yl-methanone

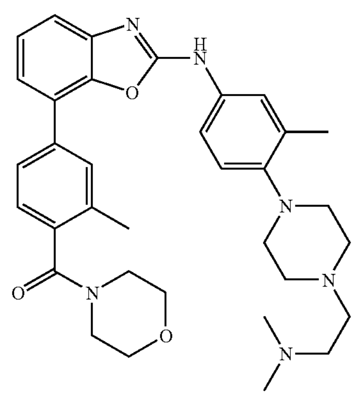 [SMILES: Cc1cc(-c2cccc3nc(Nc4ccc(N5CCN(CCN(C)C)CC5)c(C)c4)oc23)ccc1C(=O)N1CCOCC1]

$R_t$=1.86 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 583 $(M+1)^+$.

EXAMPLE 103

4-[7-(3,5-Difluoro-4-morpholin-4-ylmethyl-phenyl)-benzooxazol-2-ylamino]-N,N-diethyl-2-methyl-benzamide

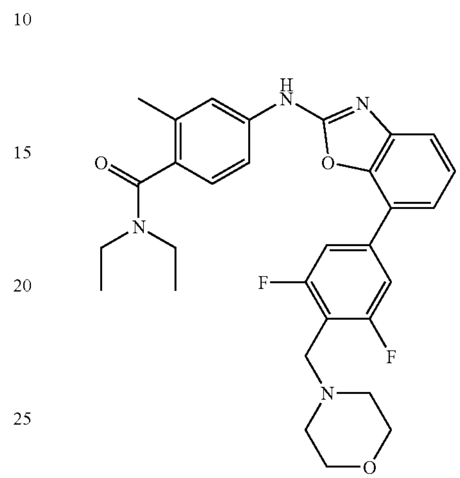

$R_t$=2.04 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 535 $(M+1)^+$.

EXAMPLE 104

{4-[7-(3,5-Difluoro-4-morpholin-4-ylmethyl-phenyl)-benzooxazol-2-ylamino]-2-methyl-phenyl}-(4-ethyl-piperazin-1-yl)-methanone

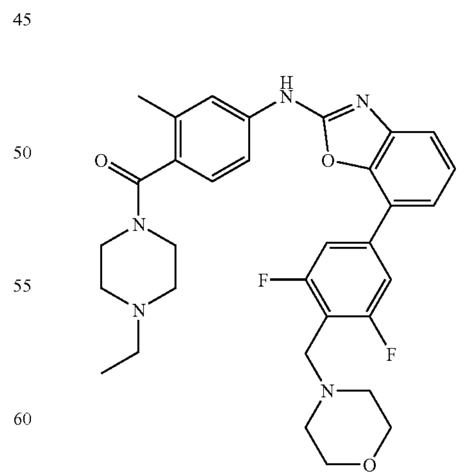

$R_t$=1.71 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 576 $(M+1)^+$.

EXAMPLE 105

[4-(4-Isopropyl-piperazin-1-yl)-3-methyl-phenyl]-[7-(4-methanesulfonyl-phenyl)-benzooxazol-2-yl]-amine

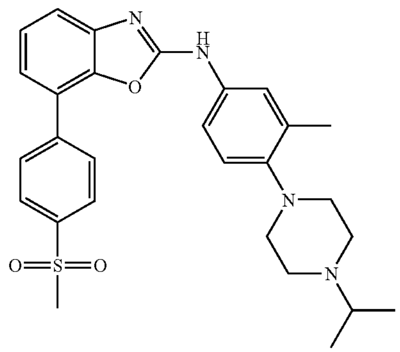 [SMILES: Cc1cc(Nc2nc3cccc(-c4ccc(S(C)(=O)=O)cc4)c3o2)ccc1N1CCN(C(C)C)CC1]

$R_t$=2.04 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 505 $(M+1)^+$.

EXAMPLE 106

(4-{2-[4-(4-Isopropyl-piperazin-1-yl)-3-methyl-phenylamino]-benzooxazol-7-yl}-2-methyl-phenyl)-morpholin-4-yl-methanone

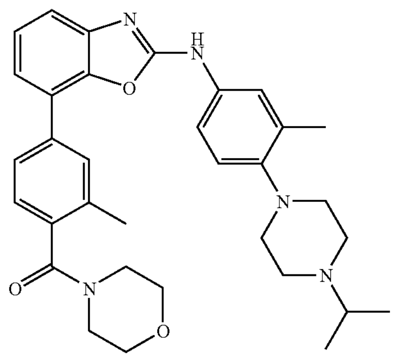 [SMILES: Cc1cc(-c2cccc3nc(Nc4ccc(N5CCN(C(C)C)CC5)c(C)c4)oc23)ccc1C(=O)N1CCOCC1]

$R_t$=2.01 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 554 $(M+1)^+$.

EXAMPLE 107

{4-[4-(2-Dimethylamino-ethyl)-piperazin-1-yl]-3-methyl-phenyl}-{7-[4-(1,1-dioxo-1lambda*6*-thiomorpholin-4-ylmethyl)-3,5-difluoro-phenyl]-benzooxazol-2-yl}-amine

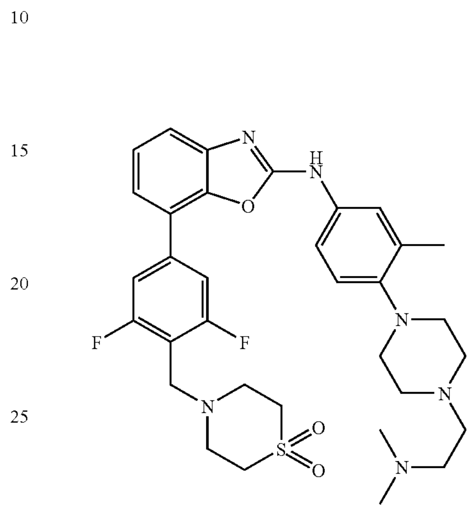

$R_t$=1.87 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 639 $(M+1)^+$.

EXAMPLE 108

{7-[4-(1,1-Dioxo-1lambda*6*-thiomorpholin-4-ylmethyl)-3,5-difluoro-phenyl]-benzooxazol-2-yl}-{4-[4-(2-methoxy-ethyl)-piperazin-1-yl]-3-methyl-phenyl}-amine

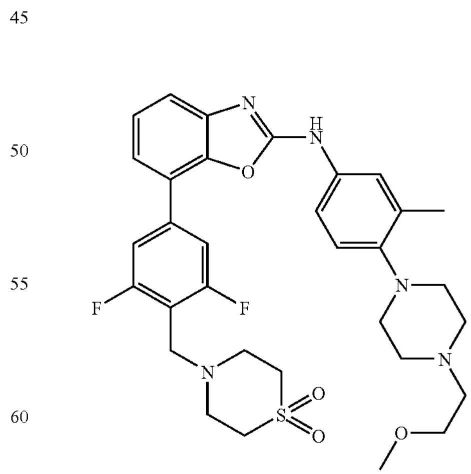

$R_t$=2.01 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 626 $(M+1)^+$.

EXAMPLE 109

(4-{2-[4-(4-Ethyl-piperazin-1-yl)-3-methyl-phenylamino]-benzooxazol-7-yl}-2,6-difluoro-phenyl)-morpholin-4-yl-methanone

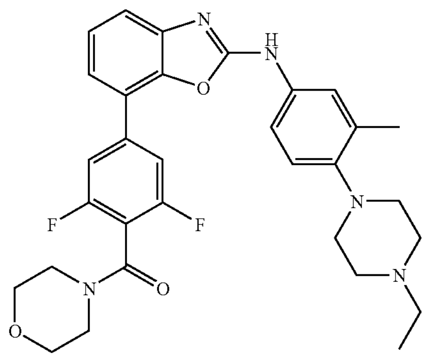 [SMILES: CCN1CCN(c2ccc(Nc3nc4cccc(-c5cc(F)c(C(=O)N6CCOCC6)c(F)c5)c4o3)cc2C)CC1]

$R_t$=2.04 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 562 $(M+1)^+$.

EXAMPLE 110

{2-Methyl-4-[7-(3-methyl-4-morpholin-4-ylmethyl-phenyl)-benzooxazol-2-ylamino]-phenyl}-pyrrolidin-1-yl-methanone

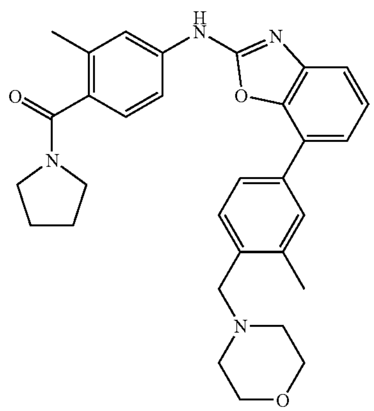 [SMILES: Cc1cc(-c2cccc3nc(Nc4ccc(C(=O)N5CCCC5)c(C)c4)oc23)ccc1CN1CCOCC1]

$R_t$=1.98 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 511 $(M+1)^+$.

EXAMPLE 111

2-(4-{2-[4-(4-Ethyl-piperazin-1-yl)-3-methyl-phenylamino]-benzooxazol-7-yl}-phenyl)-2-methyl-1-morpholin-4-yl-propan-1-one

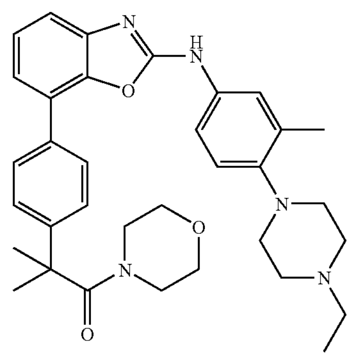 [SMILES: CCN1CCN(c2ccc(Nc3nc4cccc(-c5ccc(C(C)(C)C(=O)N6CCOCC6)cc5)c4o3)cc2C)CC1]

$R_t$=2.08 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 568 $(M+1)^+$.

EXAMPLE 112

4-{2-[4-(4-Ethyl-piperazin-1-yl)-3-methyl-phenylamino]-benzooxazol-7-yl}-benzenesulfonamide

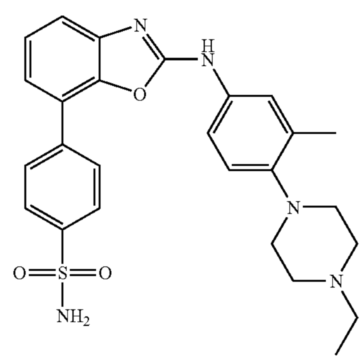 [SMILES: CCN1CCN(c2ccc(Nc3nc4cccc(-c5ccc(S(N)(=O)=O)cc5)c4o3)cc2C)CC1]

$R_t$=1.92 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 492 $(M+1)^+$.

EXAMPLE 113

[4-(4-Cyclopropyl-piperazin-1-yl)-phenyl]-[7-(4-methanesulfonyl-phenyl)-benzooxazol-2-yl]-amine

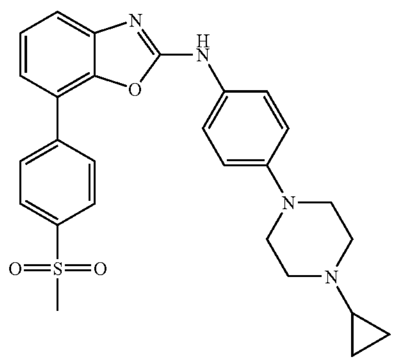 [SMILES: CS(=O)(=O)c1ccc(-c2cccc3nc(Nc4ccc(N5CCN(C6CC6)CC5)cc4)oc23)cc1]

$R_t$=1.95 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 489 $(M+1)^+$.

EXAMPLE 114

[4-(4-Cyclopropyl-piperazin-1-yl)-phenyl]-{7-[4-(1,1-dioxo-1lambda*6*-thiomorpholin-4-ylmethyl)-3,5-difluoro-phenyl]-benzooxazol-2-yl}-amine

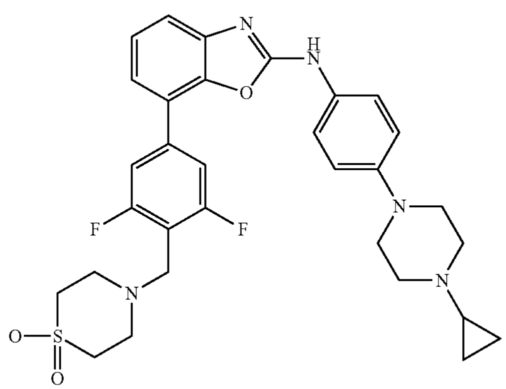

$R_t$=1.95 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 594 $(M+1)^+$.

EXAMPLE 115

[7-(4-Methanesulfonyl-phenyl)-benzooxazol-2-yl]-{4-[4-(2-methoxy-ethyl)-piperazin-1-yl]-3-methyl-phenyl}-amine

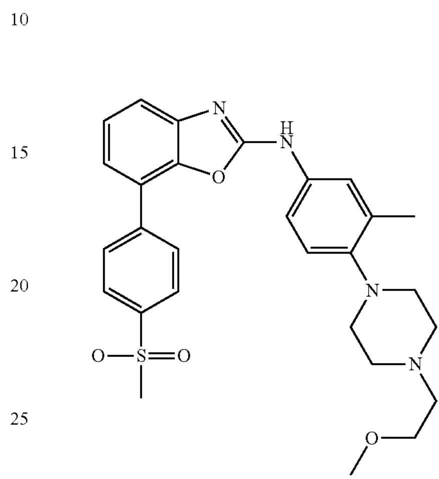

$R_t$=2.02 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 521 $(M+1)^+$.

EXAMPLE 116

(1,1-Dioxo-1lambda*6*-thiomorpholin-4-yl)-(4-{2-[4-(4-ethyl-piperazin-1-yl)-3-methyl-phenylamino]-benzooxazol-7-yl}-phenyl)-methanone

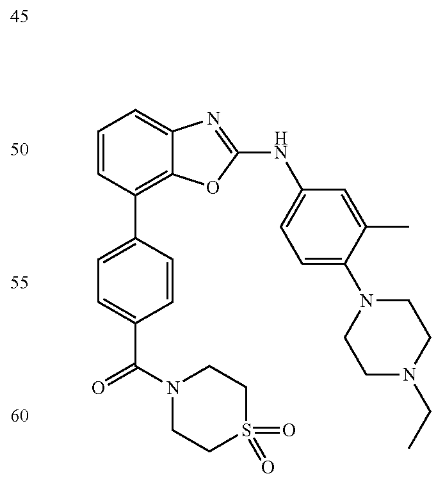

$R_t$=1.94 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 574 $(M+1)^+$.

EXAMPLE 117

4-{7-[4-(4-Acetyl-piperazin-1-ylmethyl)-3,5-difluoro-phenyl]-benzooxazol-2-ylamino}-N,N-diethyl-2-methyl-benzamide

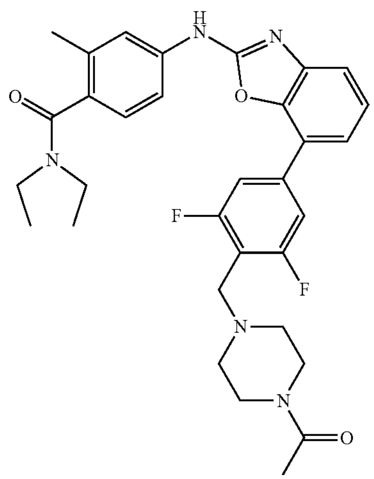 [SMILES: CCN(CC)C(=O)c1ccc(Nc2nc3cccc(-c4cc(F)c(CN5CCN(C(C)=O)CC5)c(F)c4)c3o2)cc1C]

$R_t$=2.014 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 576 $(M+1)^+$.

EXAMPLE 118

4-[7-(3,5-Difluoro-4-piperazin-1-ylmethyl-phenyl)-benzooxazol-2-ylamino]-N,N-diethyl-2-methyl-benzamide

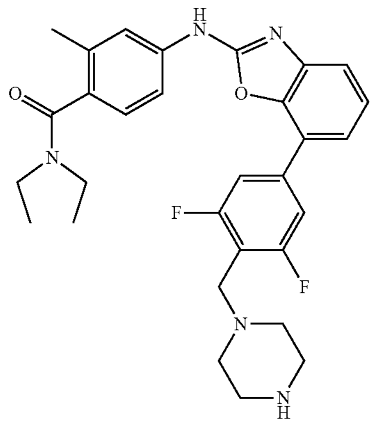 [SMILES: CCN(CC)C(=O)c1ccc(Nc2nc3cccc(-c4cc(F)c(CN5CCNCC5)c(F)c4)c3o2)cc1C]

$R_t$=1.96 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 534 $(M+1)^+$.

Example 118 is prepared from 4-{4-[2-(4-diethylcarbamoyl-3-methyl-phenylamino)-benzooxazol-7-yl]-2,6-difluoro-benzyl}-piperazine-1-carboxylic acid tert-butyl ester as follows:

A mixture of 0.146 g (0.224 mmol) 4-{4-[2-(4-diethylcarbamoyl-3-methyl-phenylamino)-benzooxazol-7-yl]-2,6-difluoro-benzyl}-piperazine-1-carboxylic acid tert-butyl ester, 2 ml trifluoroacetic acid and 10 ml dichloromethane is stirred at room temperature for 2 h. Then the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, 100% EtOAc=>EtOAc:MeOH=1:1+1% triethylamine) to afford 0.04 g of the title compound as a white solid.

EXAMPLE 119

(4-{2-[4-(4-Ethyl-piperazin-1-ylmethyl)-3-methyl-phenylamino]-benzooxazol-7-yl}-2-fluoro-phenyl)-morpholin-4-yl-methanone

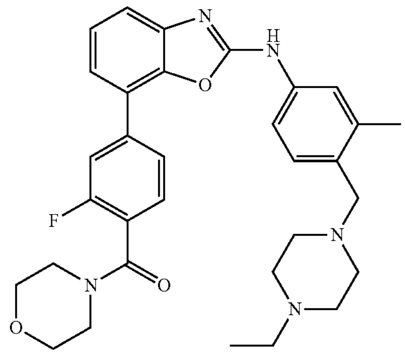 [SMILES: CCN1CCN(Cc2ccc(Nc3nc4cccc(-c5ccc(C(=O)N6CCOCC6)c(F)c5)c4o3)cc2C)CC1]

$R_t$=1.85 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 558 $(M+1)^+$.

The 1-ethyl-4-(2-methyl-4-nitro-benzyl)-piperazine used for the preparation of Example 119 is prepared as follows:

a) (2-Methyl-4-nitro-phenyl)-methanol

To a solution of 5.08 g (27.2 mmol) 2-methyl-4-nitrobenzoic acid in 50 ml dry THF, 41 ml (41 mmol) borane-THF complex (1M solution in THF) is added drop-wise at 0° C. After completion of the borane addition, the reaction mixture is stirred at room temperature for 20 h. After that a $K_2CO_3$ solution (1.33 g in 49 ml water) is slowly added under stirring. Then the reaction mixture is poured on water and extracted 3× with EtOAc. The combined organic layers are washed with water and saturated NaCl solution, dried over $MgSO_4$, filtered and the filtrate is concentrated in vacuo. The residue is taken up in diethylether, vigorously stirred, and the title compound is obtained after filtration as a yellow crystalline solid.

b) 1-Bromomethyl-2-methyl-4-nitro-benzene

To a solution of 4.55 g (27.2 mmol) (2-methyl-4-nitro-phenyl)-methanol 10.8 g (40.8 mmol) triphenylphosphine and 13.7 g (40.8 mmol) carbon tetrabromide is added at 0° C. The reaction mixture is stirred at room temperature for 1 h. After that the reaction mixture is filtered and the filtrate is concentrated in vacue. The residue is purified by chromatography (silicagel, 100% hexane=>100% EtOAc) to afford the title compound as an oil.

c) 1-Ethyl-4-(2-methyl-4-nitro-benzyl)-piperazine

A solution of 1 g (3.78 mmol) 1-bromomethyl-2-methyl-4-nitro-benzene, 0.539 ml (4.16 mmol) 1-ethylpiperazine and 0.63 ml (4.54 mmol) triethylamine in 15 ml dichloromethane is stirred at room temperature for 0.5 h. Then the reaction mixture is poured on water and extracted 3× with EtOAc. The combined organic layers are washed with water and saturated NaCl solution, dried over $MgSO_4$, filtered and the filtrate is concentrated in vacuo. The residue is purified by chromatography (silicagel, 100% EtOAc=>EtOAc:MeOH=7:3) to afford the title compound as a solid.

EXAMPLE 120

4-[7-(3,5-Difluoro-4-morpholin-4-ylmethyl-phenyl)-benzooxazol-2-ylamino]-2,N-dimethyl-benzamide

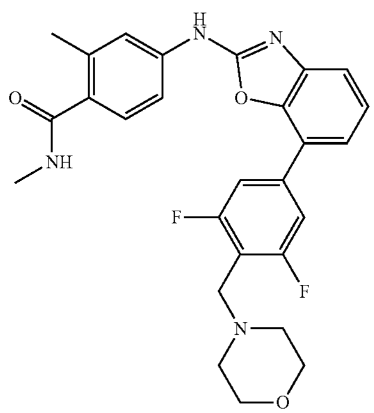 [SMILES: CNC(=O)c1ccc(Nc2nc3cccc(-c4cc(F)c(CN5CCOCC5)c(F)c4)c3o2)cc1C]

$R_t$=1.83 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 493 $(M+1)^+$.

EXAMPLE 121

[7-(3,5-Difluoro-4-morpholin-4-ylmethyl-phenyl)-benzooxazol-2-yl]-{3-methyl-4-[4-(3,3,3-trifluoro-propyiypiperazin-1-yl]-phenyl}-amine

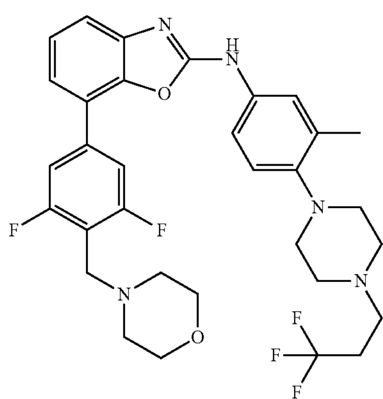 [SMILES: Cc1cc(Nc2nc3cccc(-c4cc(F)c(CN5CCOCC5)c(F)c4)c3o2)ccc1N1CCN(CCC(F)(F)F)CC1]

$R_t$=1.90 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 616 $(M+1)^+$.

EXAMPLE 122

4-[7-(3,5-Difluoro-4-morpholin-4-ylmethyl-phenyl)-benzooxazol-2-ylamino]-N-(2-dimethylamino-ethyl)-2-methyl-benzamide

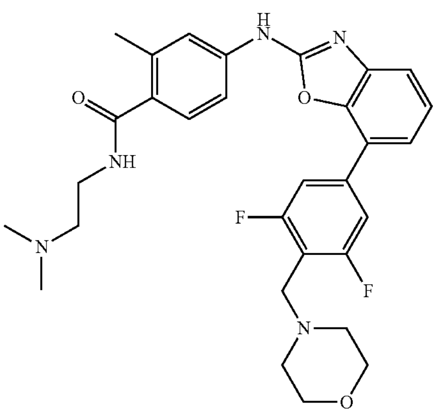 [SMILES: Cc1cc(Nc2nc3cccc(-c4cc(F)c(CN5CCOCC5)c(F)c4)c3o2)ccc1C(=O)NCCN(C)C]

$R_t$=1.71 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 550 $(M+1)^+$.

EXAMPLE 123

4-(7-{4-[2-(1,1-Dioxo-1lambda*6*-thiomorpholin-4-yl)-2-oxo-ethyl]-phenyl}-benzooxazol-2-ylamino)-N,N-diethyl-2-methoxy-benzamide $R_t$=2.02 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 591 $(M+1)^+$.

EXAMPLE 124

2-{4-[2-(4-Methanesulfonyl-phenylamino)-benzooxazol-7-yl]-phenyl}-1-morpholin-4-yl-ethanone

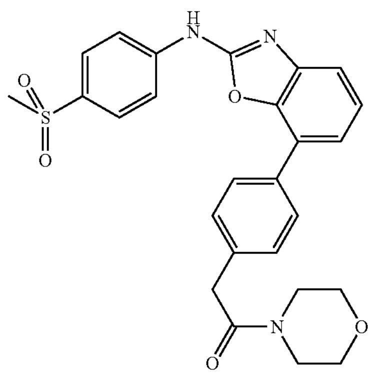 [SMILES: CS(=O)(=O)c1ccc(Nc2nc3cccc(-c4ccc(CC(=O)N5CCOCC5)cc4)c3o2)cc1]

$R_t$=1.97 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 492 $(M+1)^+$.

EXAMPLE 125

1-(4-{7-[4-(1,1-Dioxo-1lambda*6*-thiomorpholin-4-ylmethyl)-3,5-difluoro-phenyl]-benzooxazol-2-ylamino}-phenyl)-pyrrolidin-2-one

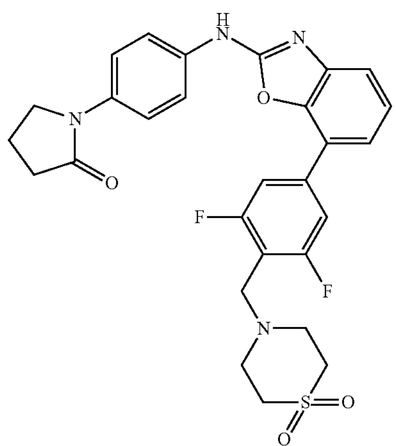 [SMILES: O=C1CCCN1c1ccc(Nc2nc3cccc(-c4cc(F)c(CN5CCS(=O)(=O)CC5)c(F)c4)c3o2)cc1]

$R_t$=2.144 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 553 $(M+1)^+$.

EXAMPLE 126

1-{4-[7-(3,5-Difluoro-4-morpholin-4-ylmethyl-phenyl)-benzooxazol-2-ylamino]-phenyl}-pyrrolidin-2-one

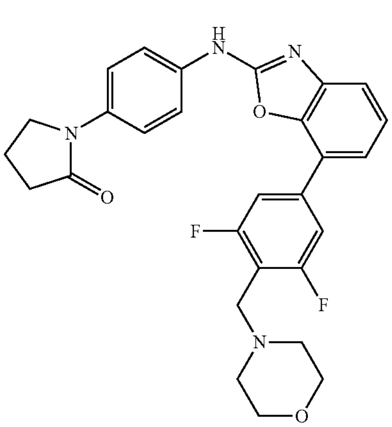 [SMILES: O=C1CCCN1c1ccc(Nc2nc3cccc(-c4cc(F)c(CN5CCOCC5)c(F)c4)c3o2)cc1]

$R_t$=1.93 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 505 $(M+1)^+$.

EXAMPLE 127

(4-{2-[4-Methoxy-3-(4-methyl-piperazin-1-yl)-phenylamino]-benzooxazol-7-yl}-2-methyl-phenyl)-morpholin-4-yl-methanone

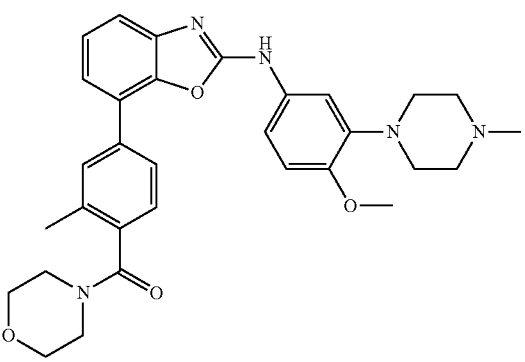 [SMILES: COc1ccc(Nc2nc3cccc(-c4ccc(C(=O)N5CCOCC5)c(C)c4)c3o2)cc1N1CCN(C)CC1]

$R_t$=1.92 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 542 $(M+1)^+$.

EXAMPLE 128

{7-[4-(1,1-Dioxo-1lambda*6*-thiomorpholin-4-ylmethyl)-3,5-difluoro-phenyl]-benzooxazol-2-yl}-[3-(4-methyl-piperazin-1-yl)-phenyl]-amine

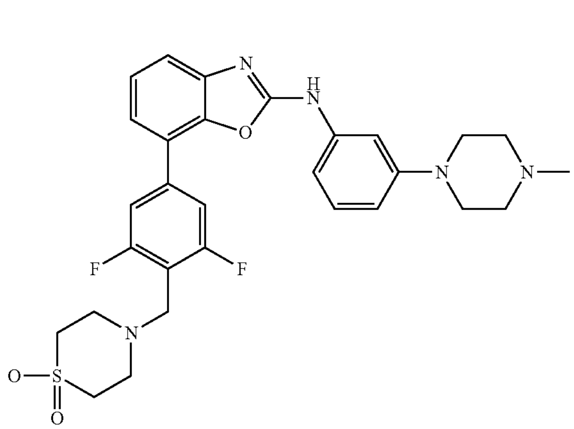

$R_t$=1.94 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 568 $(M+1)^+$.

EXAMPLE 129

(2-Methyl-4-{2-[3-(4-methyl-piperazin-1-yl)-phenylamino]-benzooxazol-7-yl}-phenyl)-morpholin-4-yl-methanone

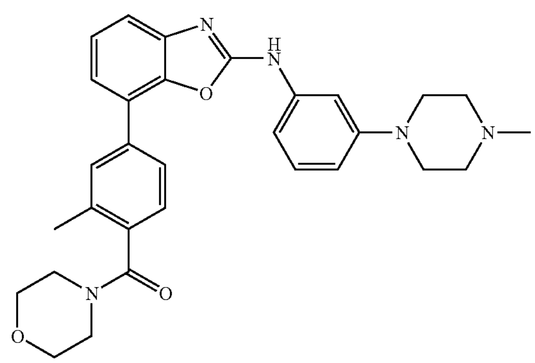 [SMILES: Cc1cc(-c2cccc3nc(Nc4cccc(N5CCN(C)CC5)c4)oc23)ccc1C(=O)N1CCOCC1]

$R_t$=1.94 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 512 $(M+1)^+$.

EXAMPLE 130

{7-[4-(1,1-Dioxo-1lambda*6*-thiomorpholin-4-ylmethyl)-3,5-difluoro-phenyl]-benzooxazol-2-yl}-[4-methoxy-3-(4-methyl-piperazin-1-yl)-phenyl]-amine

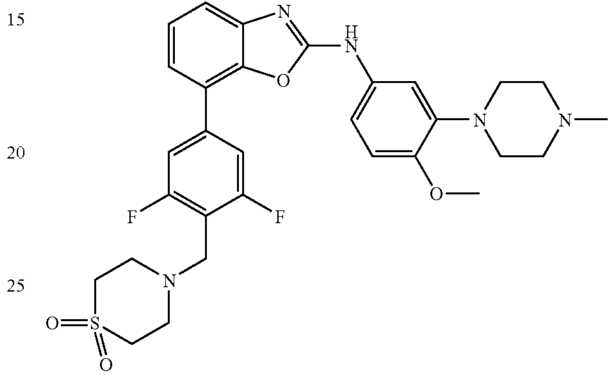

$R_t$=1.92 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 598 $(M+1)^+$.

EXAMPLE 131

{2-Fluoro-4-[2-(3-methyl-4-morpholin-4-ylmethyl-phenylamino)-benzooxazol-7-yl]-phenyl}-morpholin-4-yl-methanone

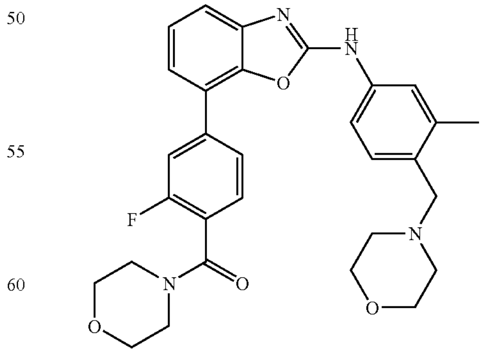

$R_t$=1.95 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 531 $(M+1)^+$.

The 4-(2-methyl-4-nitro-benzyl)-morpholine used in the preparation of example 131 is prepared as described in example 119 by using morpholine instead of 1-ethyl-piperazine.

EXAMPLE 132

N-{5-[7-(3-Fluoro-4-morpholin-4-ylmethyl-phenyl)-benzooxazol-2-ylamino]-indan-2-yl}-acetamide

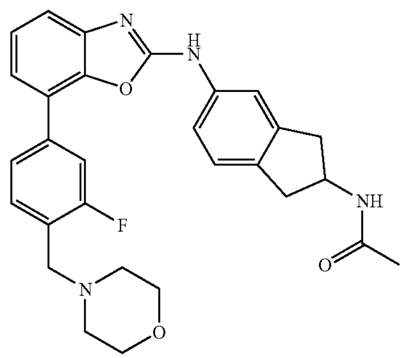 [SMILES: CC(=O)NC1Cc2ccc(Nc3nc4cccc(-c5ccc(CN6CCOCC6)c(F)c5)c4o3)cc2C1]

$R_t$=1.64 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 501 $(M+1)^+$.

EXAMPLE 133

N-(5-{7-[4-(1,1-Dioxo-1lambda*6*-thiomorpholin-4-ylmethyl)-phenyl]-benzooxazol-2-ylamino}-indan-2-yl)-acetamide

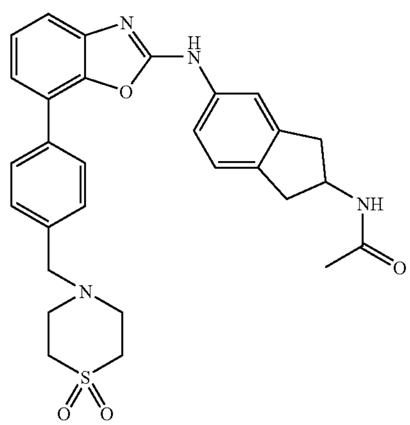 [SMILES: CC(=O)NC1Cc2ccc(Nc3nc4cccc(-c5ccc(CN6CCS(=O)(=O)CC6)cc5)c4o3)cc2C1]

$R_t$=1.67 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 530 $(M+1)^+$.

EXAMPLE 134

5-[7-(3,5-Difluoro-4-morpholin-4-ylmethyl-phenyl)-benzooxazol-2-ylamino]-1,3-dihydro-indol-2-one

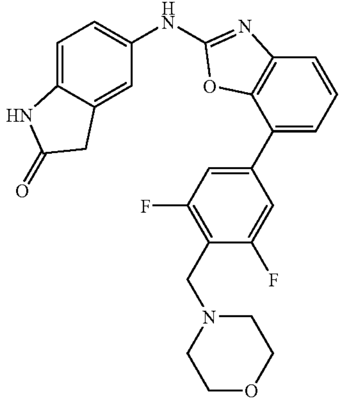 [SMILES: O=C1Cc2cc(Nc3nc4cccc(-c5cc(F)c(CN6CCOCC6)c(F)c5)c4o3)ccc2N1]

$R_t$=1.78 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 477 $(M+1)^+$.

EXAMPLE 135

2-{4-[2-(4-Methanesulfinyl-phenylamino)-benzooxazol-7-yl]-phenyl}-1-morpholin-4-yl-ethanone

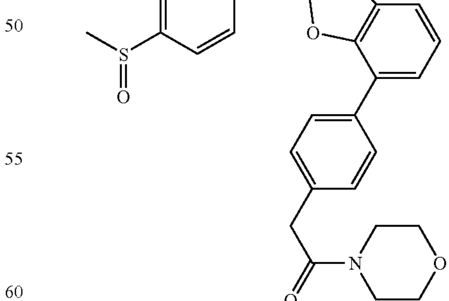

$R_t$=1.82 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 476 $(M+1)^+$.

4-Methanesulfinyl-phenylamine that is needed for the preparation of example 135 can be prepared as described by C. Almansa et al. in Journal of Medicinal Chemistry (2003), 46(16), 3463-3475.

EXAMPLE 136

[7-(4-Imidazol-1-ylmethyl-phenyl)-benzooxazol-2-yl]-(3,4,5-trimethoxy-phenyl)-amine

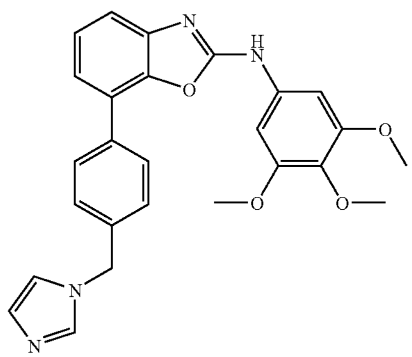 [SMILES: COc1cc(Nc2nc3cccc(-c4ccc(Cn5ccnc5)cc4)c3o2)cc(OC)c1OC]

$R_t$=1.93 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 457 $(M+1)^+$.

EXAMPLE 137

{7-[4-(4-Methyl-piperazin-1-ylmethyl)-phenyl]-benzooxazol-2-yl}3,4,5-trimethoxy-phenyl)-amine

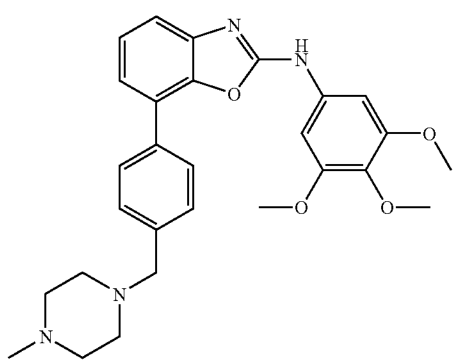

$R_t$=1.80 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 489 $(M+1)^+$.

EXAMPLE 138

[7-(4-Morpholin-4-ylmethyl-phenyl)-benzooxazol-2-yl]-(3,4,5-trimethoxy-phenyl)-amine

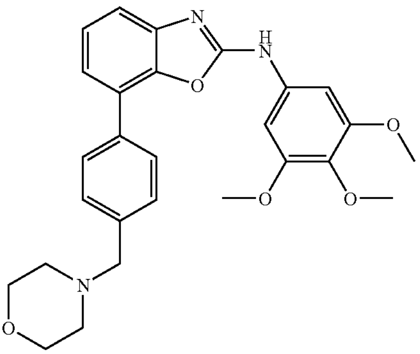 [SMILES: COc1cc(Nc2nc3cccc(-c4ccc(CN5CCOCC5)cc4)c3o2)cc(OC)c1OC]

$R_t$=1.904 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 476 $(M+1)^+$.

EXAMPLE 139

4-[2-(4-Methoxy-phenylamino)-benzooxazol-7-yl]-N-methyl-benzenesulfonamide

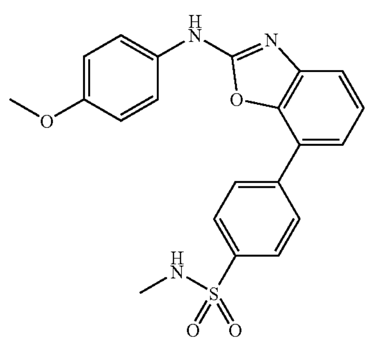 [SMILES: CNS(=O)(=O)c1ccc(-c2cccc3nc(Nc4ccc(OC)cc4)oc23)cc1]

$R_t$=2.28 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 410 $(M+1)^+$.

EXAMPLE 140

1-Morpholin-4-yl-2-{4-[2-(3,4,5-trimethoxy-phenylamino)-benzooxazol-7-yl]-phenyl}-ethanone

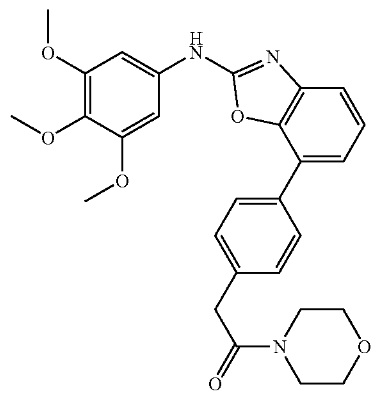 [SMILES: COc1cc(Nc2nc3cccc(-c4ccc(CC(=O)N5CCOCC5)cc4)c3o2)cc(OC)c1OC]

$R_t$=2.186 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 504 $(M+1)^+$.

EXAMPLE 141

Morpholin-4-yl-{4-[2-(3,4,5-trimethoxy-phenylamino)-benzooxazol-7-yl]-phenyl}-methanone

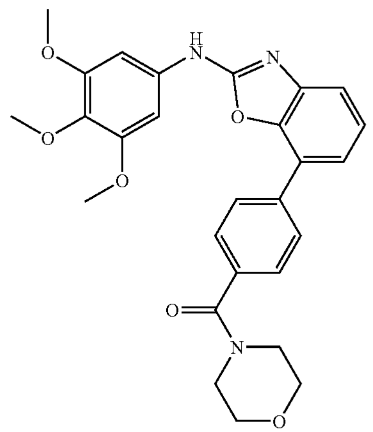 [SMILES: COc1cc(Nc2nc3cccc(-c4ccc(C(=O)N5CCOCC5)cc4)c3o2)cc(OC)c1OC]

$R_t$=2.176 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 490 $(M+1)^+$.

EXAMPLE 142

(4-Methyl-piperazin-1-yl)-{4-[2-(3,4,5-trimethoxy-phenylamino)-benzooxazol-7-yl]-phenyl}-methanone

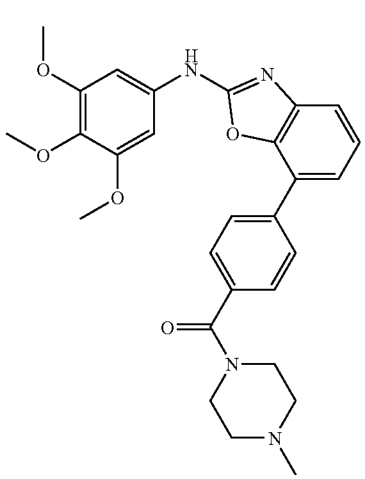 [SMILES: COc1cc(Nc2nc3cccc(-c4ccc(C(=O)N5CCN(C)CC5)cc4)c3o2)cc(OC)c1OC]

$R_t$=1.87 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 503 $(M+1)^+$.

EXAMPLE 143

{4-[2-(3,4,5-Trimethoxy-phenylamino)-benzooxazol-7-yl]-phenyl}-methanol

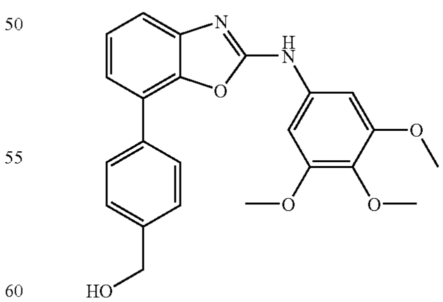

$R_t$=2.16 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 407 $(M+1)^+$.

EXAMPLE 144

4-[2-(3-Methoxy-4-methyl-phenylamino)-benzooxazol-7-yl]-methyl-benzenesulfonamide

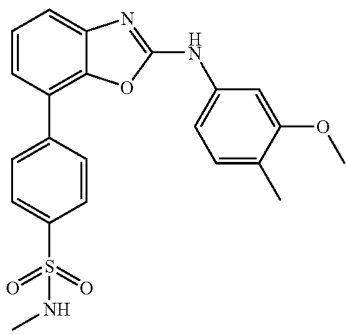 [SMILES: CNS(=O)(=O)c1ccc(-c2cccc3nc(Nc4ccc(C)c(OC)c4)oc23)cc1]

$R_t$=2.44 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 424 $(M+1)^+$.

EXAMPLE 145

N-(2-Methoxy-ethyl)-4-{7-[4-(morpholine-4-carbonyl)-phenyl]-benzooxazol-2-ylamino}-benzamide

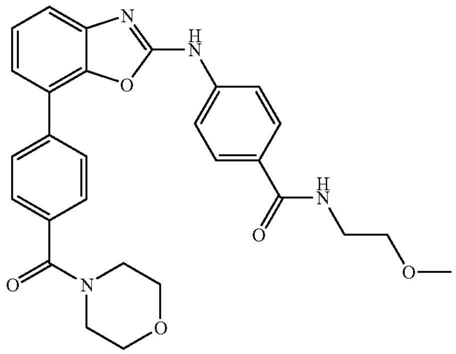 [SMILES: COCCNC(=O)c1ccc(Nc2nc3cccc(-c4ccc(C(=O)N5CCOCC5)cc4)c3o2)cc1]

$R_t$=2.035 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 501 $(M+1)^+$.

EXAMPLE 146

N,N-Dimethyl-4-[7-(4-sulfamoyl-phenyl)-benzooxazol-2-ylamino]-benzamide

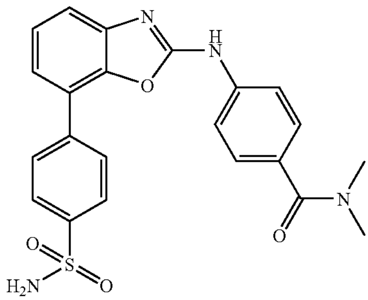 [SMILES: CN(C)C(=O)c1ccc(Nc2nc3cccc(-c4ccc(S(N)(=O)=O)cc4)c3o2)cc1]

$R_t$=2.02 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 437 $(M+1)^+$.

EXAMPLE 147

N-(2-Methoxy-ethyl)-4-{7-[4-(2-morpholin-4-yl-2-oxo-ethyl)-phenyl]-benzooxazol-2-ylamino}-benzamide

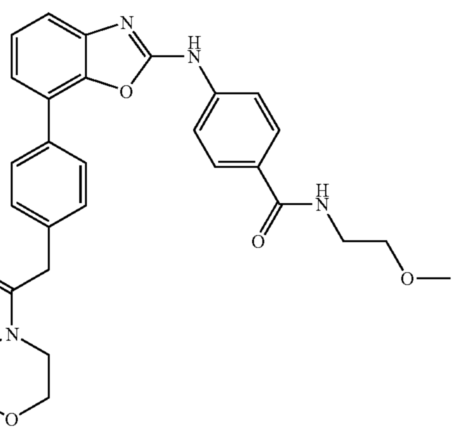

$R_t$=2.04 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 515 $(M+1)^+$.

EXAMPLE 148

N-(3-{7-[4-(Morpholine-4-carbonyl)-phenyl]-benzooxazol-2-ylamino}-phenyl)-methanesulfonamide

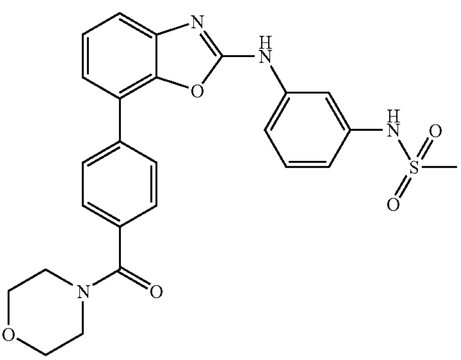 [SMILES: CS(=O)(=O)Nc1cccc(Nc2nc3cccc(-c4ccc(C(=O)N5CCOCC5)cc4)c3o2)c1]

$R_t$=2.07 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 493 $(M+1)^+$.

EXAMPLE 149

2-Methoxy-4-{7-[4-(morpholine-4-carbonyl)-phenyl]-benzooxazol-2-ylamino}-benzoic acid methyl ester

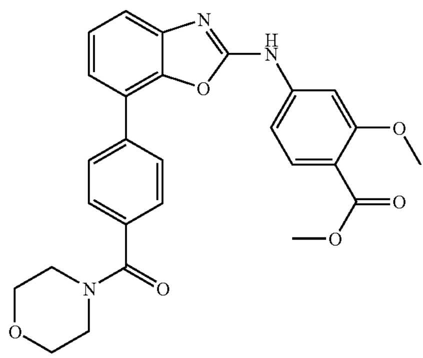 [SMILES: COC(=O)c1ccc(Nc2nc3cccc(-c4ccc(C(=O)N5CCOCC5)cc4)c3o2)cc1OC]

$R_t$=2.04 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 488 $(M+1)^+$.

EXAMPLE 150

2-Methoxy-N,N-dimethyl-4-{7-[4-(morpholine-4-carbonyl)-phenyl]-benzooxazol-2-ylamino}-benzamide

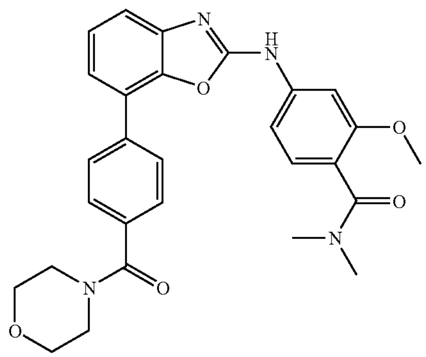 [SMILES: COc1cc(Nc2nc3cccc(-c4ccc(C(=O)N5CCOCC5)cc4)c3o2)ccc1C(=O)N(C)C]

$R_t$=1.87 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 501 $(M+1)^+$.

EXAMPLE 151

2-Methyl-2-(4-{2-[4-(4-methyl-piperazin-1-yl)-phenylamino]-benzooxazol-7-yl}-phenyl)-1-morpholin-4-yl-propan-1-one

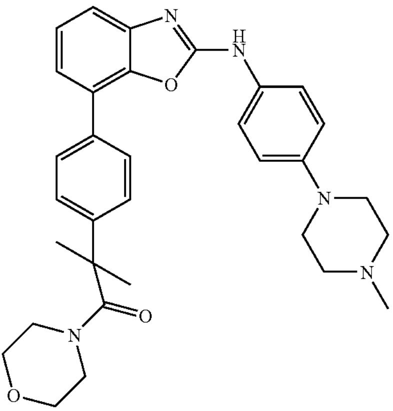 [SMILES: CN1CCN(c2ccc(Nc3nc4cccc(-c5ccc(C(C)(C)C(=O)N6CCOCC6)cc5)c4o3)cc2)CC1]

$R_t$=2.06 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 540 $(M+1)^+$.

EXAMPLE 152

[4-(3,5-Difluoro-4-morpholin-4-ylmethyl-phenyl)-oxazolo[5,4-c]pyridin-2-yl]-[4-(4-ethyl-piperazin-1-yl)-3-methyl-phenyl]-amine

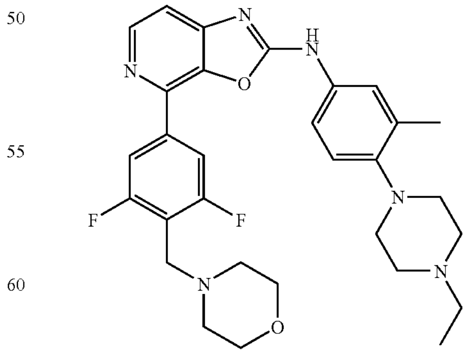

$R_t$=1.58 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 549 $(M+1)^+$.

EXAMPLE 153

{4-[4-(1,1-Dioxo-1lambda*6*-thiomorpholin-4-ylmethyl)-3,5-difluoro-phenyl]-oxazolo[5,4-c]pyridin-2-yl}-[4-(4-ethyl-piperazin-1-yl)-3-methyl-phenyl]-amine

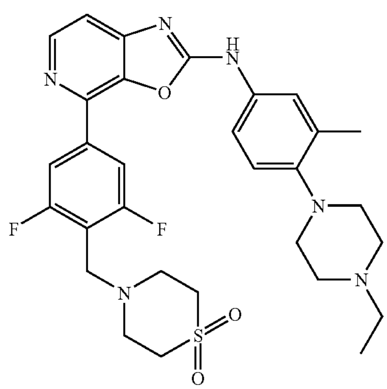 [SMILES: CCN1CCN(c2ccc(Nc3nc4ccnc(-c5cc(F)c(CN6CCS(=O)(=O)CC6)c(F)c5)c4o3)cc2C)CC1]

$R_t$=1.71 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 597 $(M+1)^+$.

EXAMPLE 154

[4-(4-Cyclopropyl-piperazin-1-yl)-3-methyl-phenyl]-{7-[4-(1,1-dioxo-1lambda*6*-thiomorpholin-4-ylmethyl)-3,5-difluoro-phenyl]-benzooxazol-2-yl}-amine

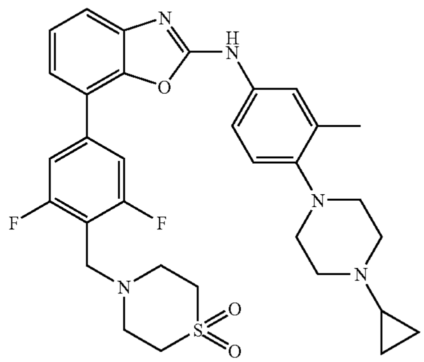 [SMILES: Cc1cc(Nc2nc3cccc(-c4cc(F)c(CN5CCS(=O)(=O)CC5)c(F)c4)c3o2)ccc1N1CCN(C2CC2)CC1]

$R_t$=2.02 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 608 $(M+1)^+$.

EXAMPLE 155

(4-{2-[4-(4-Cyclopropyl-piperazin-1-yl)-3-methyl-phenylamino]-benzooxazol-7-yl}-2-methyl-phenyl)-morpholin-4-yl-methanone

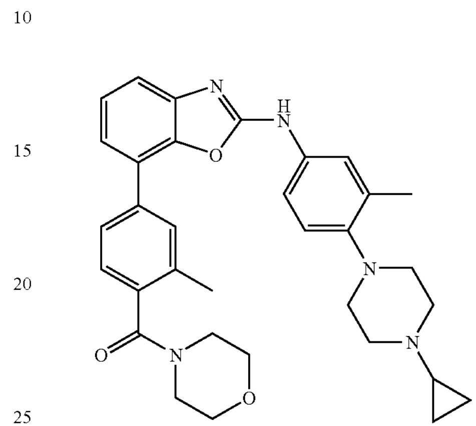

$R_t$=2.01 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 552 $(M+1)^+$.

EXAMPLE 156

(4-{2-[4-(4-Cyclopropyl-piperazin-1-yl)-3-methyl-phenylamino]-benzooxazol-7-yl}-2-fluoro-phenyl)-morpholin-4-yl-methanone

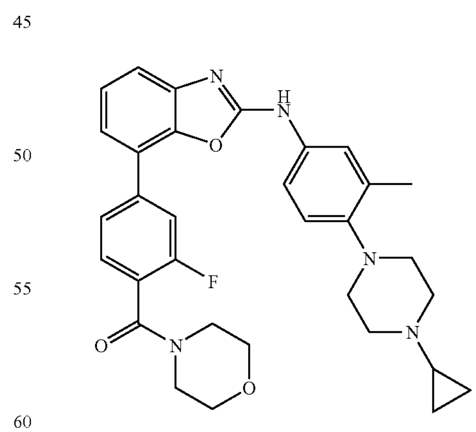

$R_t$=2.01 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 556 $(M+1)^+$.

EXAMPLE 157

2-(4-{2-[4-(4-Cyclopropyl-piperazin-1-yl)-3-methyl-phenylamino]-benzooxazol-7-yl}-phenyl)-2-methyl-1-morpholin-4-yl-propan-1-one

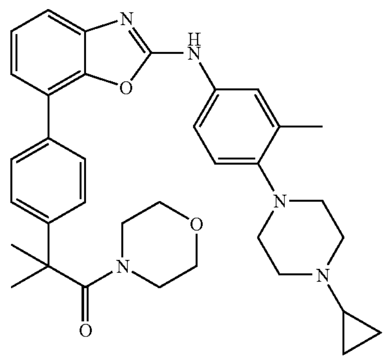 [SMILES: Cc1cc(Nc2nc3cccc(-c4ccc(C(C)(C)C(=O)N5CCOCC5)cc4)c3o2)ccc1N1CCN(C2CC2)CC1]

$R_t$=2.11 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 580 $(M+1)^+$.

EXAMPLE 158

4-[7-(3,5-Difluoro-4-morpholin-4-ylmethyl-phenyl)-benzooxazol-2-ylamino]-N-(2-dimethylamino-ethyl)-2,N-dimethyl-benzamide

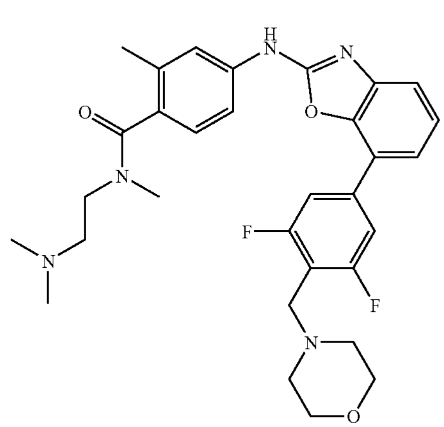 [SMILES: Cc1cc(Nc2nc3cccc(-c4cc(F)c(CN5CCOCC5)c(F)c4)c3o2)ccc1C(=O)N(C)CCN(C)C]

$R_t$=1.72 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 564 $(M+1)^+$.

EXAMPLE 159

N-(2-Dimethylamino-ethyl)-4-{7-[4-(1,1-dioxo-1lambda*6*-thiomorpholin-4-ylmethyl)-3,5-difluoro-phenyl]-benzooxazol-2-ylamino}-2,N-dimethyl-benzamide

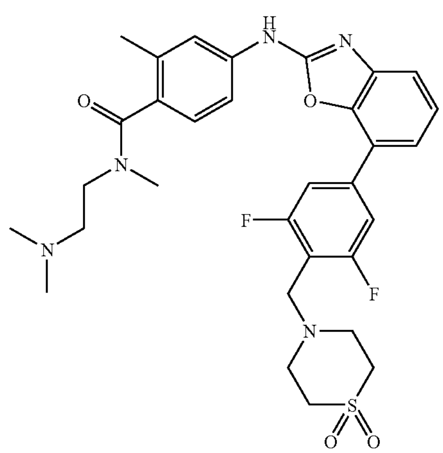 [SMILES: Cc1cc(Nc2nc3cccc(-c4cc(F)c(CN5CCS(=O)(=O)CC5)c(F)c4)c3o2)ccc1C(=O)N(C)CCN(C)C]

$R_t$=1.91 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 612 $(M+1)^+$.

EXAMPLE 160

[4-(4-Cyclopropyl-piperazin-1-yl)-3-methyl-phenyl]-[7-(3,5-difluoro-4-morpholin-4-ylmethyl-phenyl)-benzooxazol-2-yl]-amine

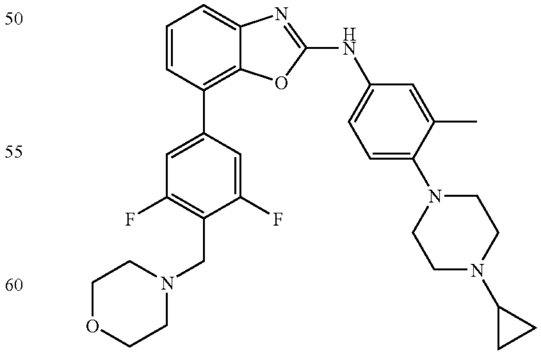

$R_t$=1.82 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 560 $(M+1)^+$.

EXAMPLE 161

5-[7-(3,5-Difluoro-4-morpholin-4-ylmethyl-phenyl)-benzooxazol-2-ylamino]-1,3-dimethyl-1H-pyridin-2-one

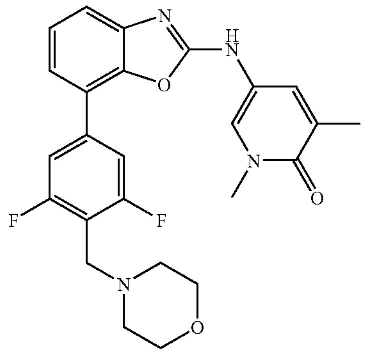 [SMILES: Cc1cc(Nc2nc3cccc(-c4cc(F)c(CN5CCOCC5)c(F)c4)c3o2)cn(C)c1=O]

$R_t$=1.72 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 467 $(M+1)^+$.

The 5-amino-1,3-dimethyl-1H-pyridin-2-one needed for the preparation of the title compound is as follows:

a) 5-Amino-1,3-dimethyl-1H-pyridin-2-one

A solution of 1.0 g (5.77 mmol) 1,3-dimethyl-5-nitro-1H-pyridin-2-one in 40 ml MeOH:THF=1:1 is hydrogenated in the presence of 0.18 g 10% Pd/C (Engelhard 4505). The reaction mixture is filtered (2 glass fiber filters used) and the filtrate is concentrated in vacuo to afford the crude title compound as an oil.

b) 1,3-Dimethyl-5-nitro-1H-pyridin-2-one

A mixture of 1 g (6.49 mmol) 1-hydroxy-3-methyl-5-nitropyridine, 0.197 g (7.8 mmol) NaH and 0.61 ml (9.73 mmol) MeI in 20 ml DMF is stirred at room temperature for 20 h. Then the reaction mixture is poured on water and extracted 3× with EtOAc. The combined organic layers are washed with water and saturated NaCl solution, dried over $MgSO_4$, filtered and the filtrate is concentrated in vacuo to afford the title compound as off-white crystals.

EXAMPLE 162

(4-{2-[4-(4-Cyclopropyl-piperazin-1-yl)-3-methyl-phenylamino]-benzooxazol-7-yl}-2-methyl-phenyl)-(1,1-dioxo-1lambda*6*-thiomorpholin-4-yl)-methanone

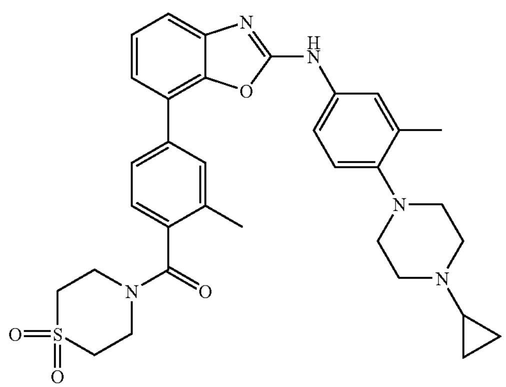 [SMILES: Cc1cc(-c2cccc3nc(Nc4ccc(N5CCN(C6CC6)CC5)c(C)c4)oc23)ccc1C(=O)N1CCS(=O)(=O)CC1]

$R_t$=2.03 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 600 $(M+1)^+$.

EXAMPLE 163

[7-(3,5-Difluoro-4-morpholin-4-ylmethyl-phenyl)-benzooxazol-2-yl]-(3-methyl-4-morpholin-4-yl-phenyl)-amine

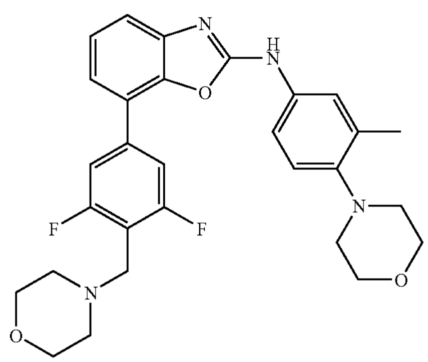 [SMILES: Cc1cc(Nc2nc3cccc(-c4cc(F)c(CN5CCOCC5)c(F)c4)c3o2)ccc1N1CCOCC1]

$R_t$=1.92 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 521 $(M+1)^+$.

EXAMPLE 164

{7-[4-(1,1-Dioxo-1lambda*6*-thiomorpholin-4-ylmethyl)-3,5-difluoro-phenyl]-benzooxazol-2-yl}-(3-methyl-4-morpholin-4-yl-phenyl)-amine

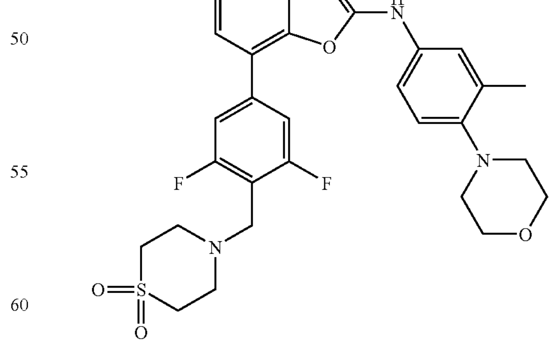

$R_t$=2.02 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 569 $(M+1)^+$.

EXAMPLE 165

(1,1-Dioxo-1lambda*6*-thiomorpholin-4-yl)-{4-[2-(3-methyl-4-morpholin-4-ylmethyl-phenylamino)-benzooxazol-7-yl]-phenyl}-methanone

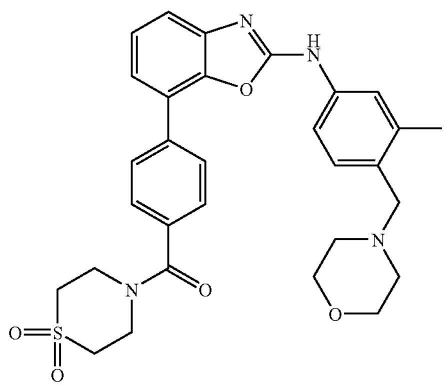 [SMILES: Cc1cc(Nc2nc3cccc(-c4ccc(C(=O)N5CCS(=O)(=O)CC5)cc4)c3o2)ccc1CN1CCOCC1]

$R_t$=1.89 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 561 $(M+1)^+$.

EXAMPLE 166

{2-Methyl-4-[2-(3-methyl-4-morpholin-4-ylmethyl-phenylamino)-benzooxazol-7-yl]-phenyl}-morpholin-4-yl-methanone

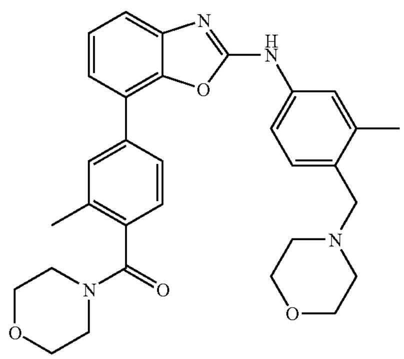 [SMILES: Cc1cc(Nc2nc3cccc(-c4ccc(C(=O)N5CCOCC5)c(C)c4)c3o2)ccc1CN1CCOCC1]

$R_t$=1.92 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 527 $(M+1)^+$.

EXAMPLE 167

2-Methyl-2-{4-[2-(3-methyl-4-morpholin-4-ylmethyl-phenylamino)-benzooxazol-7-yl]-phenyl}-1-morpholin-4-yl-propan-1-one

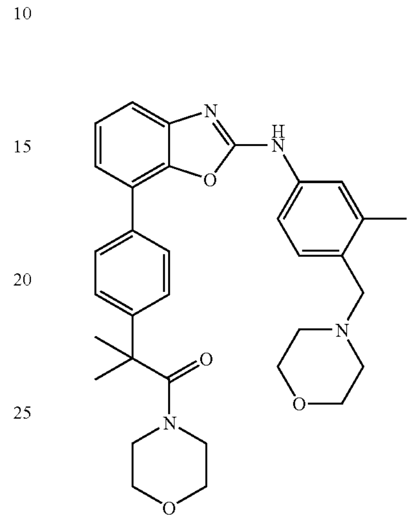

$R_t$=2.06 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 555 $(M+1)^+$.

EXAMPLE 168

4-{4-[4-(1,1-Dioxo-1lambda*6*-thiomorpholin-4-ylmethyl)-3,5-difluoro-phenyl]-oxazolo[5,4-c]pyridin-2-ylamino}-2,N,N-trimethyl-benzamide

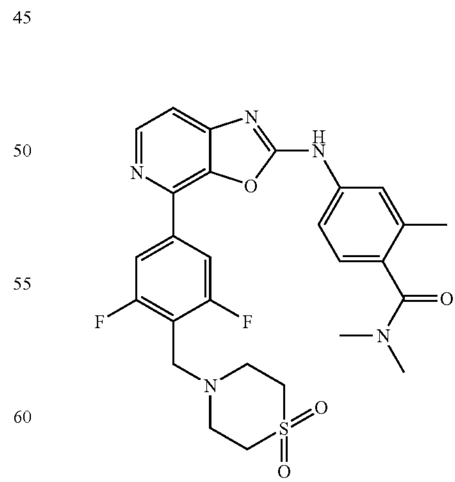

$R_t$=1.80 min (Waters Symmetry C8, 2.1×50 mm, detection 210-250 nM, 5% to 100% $CH_3CN$ in $H_2O$ in 2 min+0.05% TFA, flow rate 1.0 ml/min); MS: 556 $(M+1)^+$.

EXAMPLE 169

4-{7-[3,5-Difluoro-4-(3-oxo-piperazin-1-ylmethyl)-phenyl]-benzooxazol-2-ylamino}-2,N,N-trimethyl-benzamide

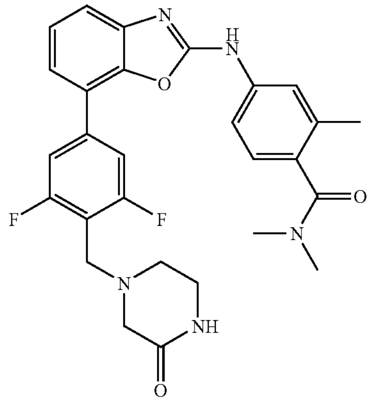 [SMILES: Cc1cc(Nc2nc3cccc(-c4cc(F)c(CN5CCNC(=O)C5)c(F)c4)c3o2)ccc1C(=O)N(C)C]

EXAMPLE 170

4-{2,6-Difluoro-4-[2-(3-methyl-4-morpholin-4-yl-phenylamino)-benzooxazol-7-yl]-benzyl}-piperazin-2-one

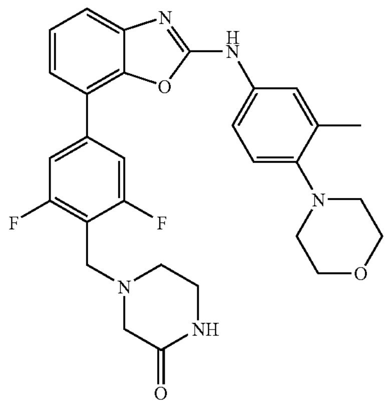 [SMILES: Cc1cc(Nc2nc3cccc(-c4cc(F)c(CN5CCNC(=O)C5)c(F)c4)c3o2)ccc1N1CCOCC1]

EXAMPLE 171

4-(4-{2-[4-(4-Cyclopropyl-piperazin-1-yl)-3-methyl-phenylamino]-benzooxazol-7-yl}-2,6-difluoro-benzyl)-piperazin-2-one

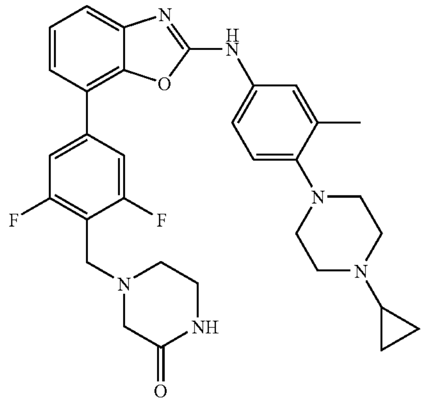 [SMILES: Cc1cc(Nc2nc3cccc(-c4cc(F)c(CN5CCNC(=O)C5)c(F)c4)c3o2)ccc1N1CCN(C2CC2)CC1]

EXAMPLE 172

4-{7-[3,5-Difluoro-4-(4-methyl-3-oxo-piperazin-1-ylmethyl)-phenyl]-benzooxazol-2-ylamino}-2,N,N-trimethyl-benzamide

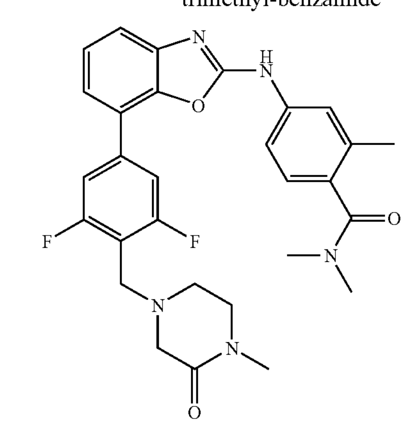

EXAMPLE 173

4-{2,6-Difluoro-4-[2-(3-methyl-4-morpholin-4-yl-phenylamino)-benzooxazol-7-yl]-benzyl}-1-methyl-piperazin-2-one

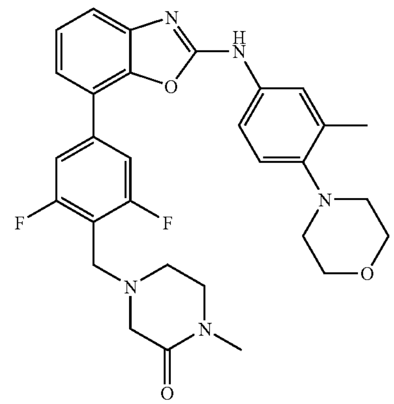 [SMILES: Cc1cc(Nc2nc3cccc(-c4cc(F)c(CN5CCN(C)C(=O)C5)c(F)c4)c3o2)ccc1N1CCOCC1]

EXAMPLE 174

4-(4-{2-[4-(4-Cyclopropyl-piperazin-1-yl)-3-methyl-phenylamino]-benzooxazol-7-yl}-2,6-difluoro-benzyl)-1-methyl-piperazin-2-one

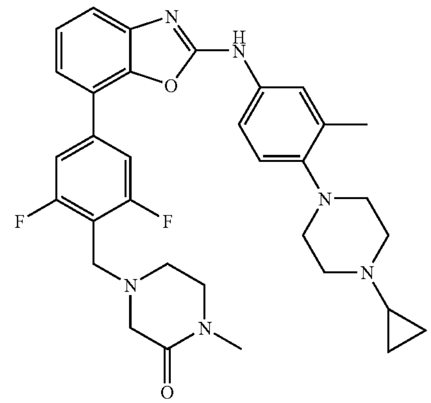 [SMILES: Cc1cc(Nc2nc3cccc(-c4cc(F)c(CN5CCN(C)C(=O)C5)c(F)c4)c3o2)ccc1N1CCN(C2CC2)CC1]

EXAMPLE 175

4-[7-(4-Methanesulfinylmethyl-3-methyl-phenyl)-benzooxazol-2-ylamino]-2,N,N-trimethyl-benzamide

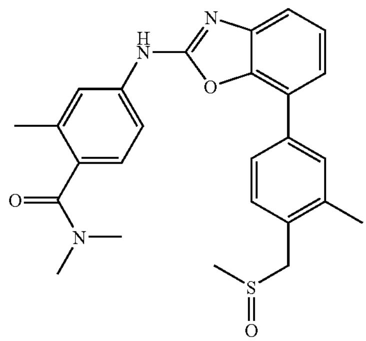

EXAMPLE 176

[4-(4-Cyclopropyl-piperazin-1-yl)-3-methyl-phenyl]-[7-(4-methanesulfonylmethyl-3-methyl-phenyl)-benzooxazol-2-yl]-amine

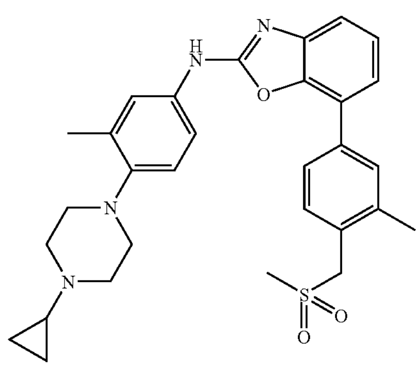 [SMILES: Cc1cc(-c2cccc3nc(Nc4ccc(N5CCN(C6CC6)CC5)c(C)c4)oc23)ccc1CS(C)(=O)=O]

EXAMPLE 177

[7-(4-Methanesulfinylmethyl-3-methyl-phenyl)-benzooxazol-2-yl]-(4-methyl-3-morpholin-4-yl-phenyl)-amine

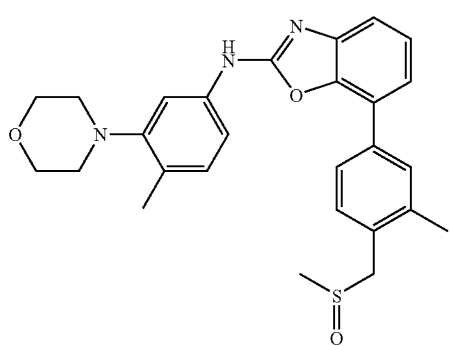 [SMILES: Cc1cc(-c2cccc3nc(Nc4ccc(C)c(N5CCOCC5)c4)oc23)ccc1CS(C)=O]

EXAMPLE 178

{4-[7-(3,5-Difluoro-4-morpholin-4-ylmethyl-phenyl)-benzooxazol-2-ylamino]-2-methyl-phenyl}-morpholin-4-yl-methanone

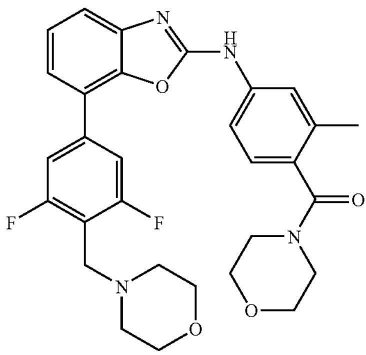 [SMILES: Cc1cc(Nc2nc3cccc(-c4cc(F)c(CN5CCOCC5)c(F)c4)c3o2)ccc1C(=O)N1CCOCC1]

EXAMPLE 179

4-[7-(3,5-Difluoro-4-morpholin-4-ylmethyl-phenyl)-benzooxazol-2-ylamino]-N-(2-methoxy-ethyl)-2-methyl-benzamide

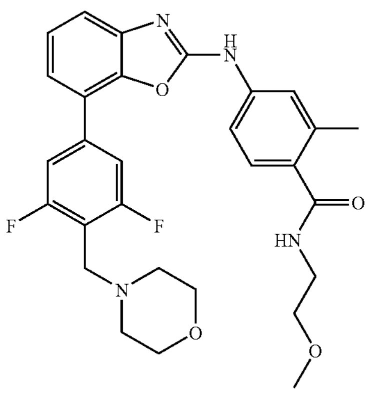 [SMILES: COCCNC(=O)c1ccc(Nc2nc3cccc(-c4cc(F)c(CN5CCOCC5)c(F)c4)c3o2)cc1C]

EXAMPLE 180

4-[7-(3,5-Difluoro-4-morpholin-4-ylmethyl-phenyl)-benzooxazol-2-ylamino]-N-(3-dimethylamino-propyl)-2-methyl-benzamide

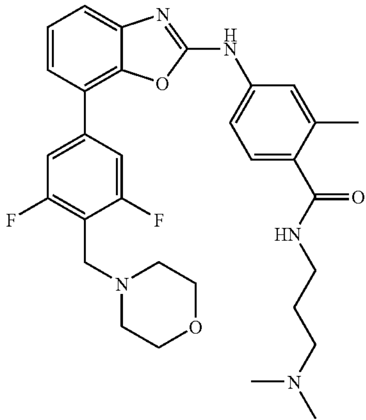 [SMILES: Cc1cc(Nc2nc3cccc(-c4cc(F)c(CN5CCOCC5)c(F)c4)c3o2)ccc1C(=O)NCCCN(C)C]

EXAMPLE 181

[7-(3,5-Difluoro-4-morpholin-4-ylmethyl-phenyl)-benzooxazol-2-yl]-(6-methoxy-5-methyl-pyridin-3-yl)-amine

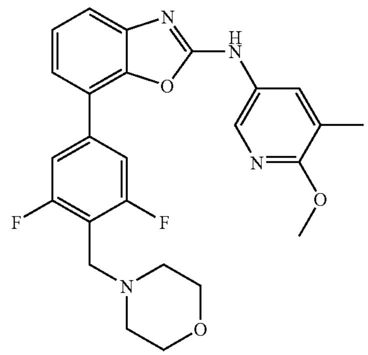 [SMILES: COc1ncc(Nc2nc3cccc(-c4cc(F)c(CN5CCOCC5)c(F)c4)c3o2)cc1C]

EXAMPLE 182

4-[7-(3,5-Difluoro-4-morpholin-4-ylmethyl-phenyl)-benzooxazol-2-ylamino]-2,6,N,N-tetramethyl-benzamide

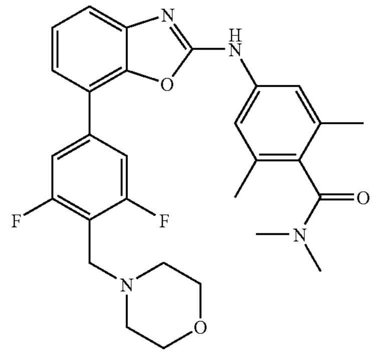 [SMILES: Cc1cc(Nc2nc3cccc(-c4cc(F)c(CN5CCOCC5)c(F)c4)c3o2)cc(C)c1C(=O)N(C)C]

EXAMPLE 183

4-[7-(3,5-Difluoro-4-morpholin-4-ylmethyl-phenyl)-benzooxazol-2-ylamino]-2-ethyl-N,N-dimethyl-benzamide

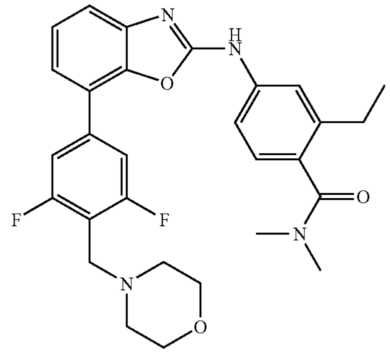 [SMILES: CCc1cc(Nc2nc3cccc(-c4cc(F)c(CN5CCOCC5)c(F)c4)c3o2)ccc1C(=O)N(C)C]

EXAMPLE 184

4-[7-(3,5-Difluoro-4-morpholin-4-ylmethyl-phenyl)-benzooxazol-2-ylamino]-N-(2-methoxy-ethyl)-2,N-dimethyl-benzamide

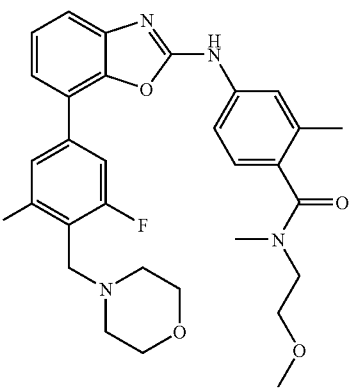

EXAMPLE 185

4-[7-(3,5-Difluoro-4-morpholin-4-ylmethyl-phenyl)-benzooxazol-2-ylamino]-2-morpholin-4-yl-benzonitrile

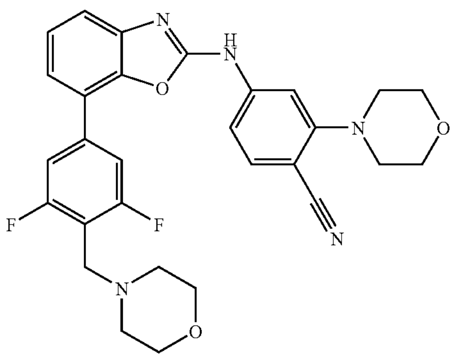 [SMILES: N#Cc1ccc(Nc2nc3cccc(-c4cc(F)c(CN5CCOCC5)c(F)c4)c3o2)cc1N1CCOCC1]

EXAMPLE 186

Soft Capsules 5000 soft gelatin capsules, each comprising as active ingredient 0.05 g of one of the compounds of formula I mentioned in the preceding Examples, are prepared as follows:

Composition

| | |
|---|---|
| Active ingredient | 250 g |
| Lauroglycol | 2 litres |

Preparation process: The pulverized active ingredient is suspended in Lauroglykol® (propylene glycol laurate, Gattefossé S.A., Saint Priest, France) and ground in a wet pulverizer to produce a particle size of about 1 to 3 μm. 0.419 g portions of the mixture are then introduced into soft gelatin capsules using a capsule-filling machine.

EXAMPLE 187

EPK JAK/TYK-Kinase Family Profiling Assays

The efficacy of the compounds of the invention as inhibitors of JAK/TYK kinase activity can be demonstrated as follows:

All four kinases of the JAK/TYK-kinase family are used as purified recombinant GST-fusion proteins, containing the active kinase domains. GST-JAK1(866-1154), GST-JAK3 (811-1124), and GST-TYK2(888-1187) are expressed and purified by affinity chromatography. GST-JAK2(808-1132) is purchased from Invitrogen (Carlsbad, USA, #4288).

The kinase assays are based on the Caliper mobility shift assay using the LabChip 3000 systems. This technology is similar to capillary electrophoresis and uses charge driven separation of substrate and product in a microfluidic chip.

All kinase reactions are performed in 384 well microtiter plates in a total reaction volume of 18 μl. The assay plates are prepared with 0.1 μl per well of test compound in the appropriate test concentration, as described under the section "preparation of compound dilutions". The reactions are started by combining 9 μl of substrate mix (consisting of peptide and ATP) with 9 μl of kinase dilution. The reactions are incubated for 60 minutes at 30° C. and stopped by adding 70 μl of stop buffer (100 mM Hepes, 5% DMSO, 0.1% Coating reagent, 10 mM EDTA, 0.015% Brij 35).

Fluorescently labeled synthetic peptides are used as substrates in all reactions. A peptide derived from the sequence of IRS-1 (IRS-1 peptide, FITC-Ahx-KKSRGDYMTMQIG-$NH_2$ (SEQ ID NO: 1); see J. Biol. Chem. 268(33), 25146-51 (1993)) is used for JAK1 and TYK2 and a peptide named JAK3tide (FITC-GGEEEEYFELVKKKK-$NH_2$ (SEQ ID NO: 2); Upstate (Millipore), Temecula, Calif., USA)) for JAK2 and JAK3. Specific assay conditions are described in Table 1:

GGEEEYFELVKKKK

TABLE 1

Assay conditions of individual kinase assays

| Kinase | JAK1 | JAK2 | JAK3 | TYK2 |
|---|---|---|---|---|
| Buffer | 50 mM Hepes pH 7.5, 0.02% Tween 20, 1 mM DTT, 0.02% BSA, 12 mM MgCl2 | 50 mM Hepes pH 7.5, 0.02% Tween 20, 1 mM DTT, 0.02% BSA, 9 mM MgCl2 | 50 mM Hepes pH 7.5, 0.02% Tween 20, 1 mM DTT, 0.02% BSA, 1.5 mM $MgCl_2$ | 50 mM Hepes pH 7.5, 0.02% Tween 20, 1 mM DTT, 0.02% BSA, 9 mM MgCl2 |
| DMSO | 0.6% | 0.6% | 0.6% | 0.6% |
| Kinase conc. | 50 nM | 1.8 nM | 6 nM | 40 nM |
| Substrate peptide conc. | 5 μM | 2 μM | 2 μM | 5 μM |
| ATP conc. | 40 μM | 20 μM | 80 μM | 30 μM |

The terminated reactions are transferred to a Caliper LabChip 3000 reader (Caliper Life Sciences, Mountain View, Calif., USA) and the turnover of each reaction is measured by determining the substrate/product ratio.

Preparation of Compound Dilutions

Test compounds are dissolved in DMSO (10 mM) and transferred into 1.4 mL flat bottom or V-shaped Matrix tubes carrying a unique 2D matrix chip by individual compound hubs. The numbers of these chips are distinctively linked to the individual compound identification numbers. The stock solutions are stored at −20° C. if not used immediately. For the test procedure the vials are defrosted and identified by a scanner whereby a working sheet is generated that guides the subsequent working steps.

Compound dilutions are made in 96 well plates. This format enabled the assay of maximally 40 individual test compounds at 8 concentrations (single points) including 4 reference compounds. The dilution protocol includes the production of pre-dilution plates, master plates and assay plates:

Pre-dilution plates: 96 polypropylene well plates are used as pre-dilution plates. A total of 4 pre-dilution plates are prepared including 10 test compounds each on the plate positions A1-A10, one standard compound at A11 and one DMSO control at A12. All dilution steps are done on a Hamilton STAR robot (Hamilton, Co., Reno, Nev., USA).

Master plates: 100 μL of individual compound dilutions including standard compound and controls of the 4 "pre-dilution plates" are transferred into a 384 "master plate" including the following concentrations 1,820, 564, 182, 54.6, 18.2, 5.46, 1.82 and 0.546 μM, respectively in 90% of DMSO.

Assay plates: Identical assay plates are then prepared by pipetting 100 nL each of compound dilutions of the master plates into 384-well "assay plates". In the following the compounds are mixed with 9 μL of assays components plus 9 μL enzyme corresponding to a 1:181 dilution steps enabling the final concentration of 10, 3.0, 1.0, 0.3, 0.1, 0.03, 0.01 and 0.003 μM, respectively. The preparation of the master plates are handled by the Matrix PlateMate Plus robot (Thermo Fisher Scientific, Handforth, Cheshire, United Kingdom) and replication of assay plates by the HummingBird robot (Genomic Solutions, Inc., Ann Arbor, Mich., USA).

On the basis of these studies, a compound of the invention shows therapeutic efficacy especially against disorders dependent on protein kinase, especially proliferative diseases mediated by JAK/TYK kinase activity.

Exemplified compounds show JAK2 enzyme inhibitory activities with IC50-values of 0.1 to 1000 nM as shown in the following table:

| Example | IC50 with Test in present Example (micromole/l) | IC50 with test in general description (named "alternative method to that given in the examples") (micromole/l) ("flash plate") |
|---|---|---|
| 1 | | 0.3366667 |
| 2 | | 0.29625 |
| 3 | | 0.5833333 |
| 4 | | 0.099 |
| 5 | | 0.15 |
| 6 | | 0.1782 |
| 7 | | 0.21 |
| 8 | | 0.368 |
| 9 | | 0.59 |
| 10 | | 0.1316667 |
| 11 | | 0.1474 |
| 12 | | 0.67 |
| 13 | | 0.174 |
| 14 | | 0.61 |
| 15 | | 0.57 |
| 16 | 0.035 | 0.093 |
| 17 | 0.012 | 0.04 |
| 18 | 0.01 | 0.01 |
| 19 | | 0.17 |
| 20 | | 1 |
| 21 | 0.019 | 0.016 |
| 22 | | 0.14 |
| 23 | | 0.19 |
| 24 | 0.019 | 0.079 |
| 25 | | 0.14 |
| 26 | | 0.052 |
| 27 | | 0.2 |
| 28 | | 0.31 |
| 29 | 0.066 | 0.25 |
| 30 | 0.021 | 0.041 |
| 31 | 0.0162333 | 0.0605 |
| 32 | | 0.27 |
| 33 | | 0.29 |
| 34 | | 0.54 |
| 35 | | 0.12 |
| 36 | | 0.12 |
| 37 | | 0.24 |
| 38 | 0.31 | 0.45 |
| 39 | | 1.2 |
| 40 | | 1.1 |
| 41 | | 0.41 |
| 42 | | 1.2 |
| 43 | | 1.9 |
| 44 | | 0.93 |
| 45 | | 0.95 |
| 46 | | 0.35 |
| 47 | | 0.5933333 |
| 48 | | 0.7 |
| 49 | | 0.52 |
| 50 | | 0.61 |
| 51 | | 0.45 |
| 52 | | 0.15 |
| 53 | | 0.5566667 |
| 54 | | 0.35 |
| 55 | | 0.42 |
| 56 | 0.051 | 0.11 |
| 57 | 0.037 | 0.15 |
| 58 | 0.037 | 0.0415 |
| 59 | | 0.041 |
| 60 | 0.17 | 0.16 |
| 61 | | 0.087 |
| 62 | 0.016 | 0.23 |
| 63 | | |
| 64 | 0.0042 | |
| 65 | 0.00825 | |
| 66 | 0.00645 | |
| 67 | 0.014 | |

-continued

| Example | IC50 with Test in present Example (micromole/l) | IC50 with test in general description (named "alternative method to that given in the examples") (micromole/l) ("flash plate") |
|---|---|---|
| 68 | 0.019 | |
| 69 | 0.0079 | |
| 70 | 0.0062 | |
| 71 | 0.015 | |
| 72 | 0.017 | |
| 73 | 0.00515 | |
| 74 | 0.005 | |
| 75 | 0.0065 | |
| 76 | 0.013 | |
| 77 | 0.0033 | |
| 78 | 0.0045 | |
| 79 | <0.003 | |
| 80 | 0.0062 | |
| 81 | 0.017 | |
| 82 | 0.0048 | |
| 83 | <0.003 | |
| 84 | <0.003 | |
| 85 | 0.0093 | |
| 86 | 0.079 | |
| 87 | 0.0048 | |
| 88 | <0.003 | |
| 89 | 0.06 | |
| 90 | 0.0565 | |
| 91 | 0.064 | |
| 92 | 0.0101 | |
| 93 | 0.052 | |
| 94 | 0.0069 | |
| 95 | 0.00685 | |
| 96 | 0.00435 | |
| 97 | 0.0215 | |
| 98 | 0.0052 | |
| 99 | 0.0192 | |
| 100 | 0.0165 | |
| 101 | 0.0036 | |
| 102 | 0.00565 | |
| 103 | 0.014 | |
| 104 | 0.015 | |
| 105 | 0.02 | |
| 106 | 0.00615 | |
| 107 | 0.0043 | |
| 108 | 0.0103 | |
| 109 | 0.011 | |
| 110 | 0.088 | |
| 111 | 0.0165 | |
| 112 | 0.0175 | |
| 113 | 0.27 | |
| 114 | 0.01415 | |
| 115 | 0.039 | |
| 116 | 0.015 | |
| 117 | 0.0295 | |
| 118 | 0.043 | |
| 119 | 0.0195 | |
| 120 | 0.039 | |
| 121 | 0.21 | |
| 122 | 0.01115 | |
| 123 | 0.0054 | |
| 124 | 0.0052 | |
| 125 | 0.0705 | |
| 126 | 0.165 | |
| 127 | 0.03 | |
| 128 | 0.019 | |
| 129 | 0.045 | |
| 130 | 0.00655 | |
| 131 | 0.0195 | |
| 132 | 0.021 | |
| 133 | 0.014 | |
| 134 | 0.098 | |
| 135 | 0.018 | |
| 136 | 0.018 | |
| 137 | 0.16 | |
| 138 | 0.014 | |
| 139 | 0.12 | 0.4 |

-continued

| Example | IC50 with Test in present Example (micromole/l) | IC50 with test in general description (named "alternative method to that given in the examples") (micromole/l) ("flash plate") |
|---|---|---|
| 140 | 0.0037 | 0.14 |
| 141 | 0.0081 | 0.22 |
| 142 | 0.0585 | 0.7 |
| 143 | 0.0165 | |
| 144 | 0.725 | |
| 145 | 0.055 | |
| 146 | 0.0195 | |
| 147 | 0.028 | |
| 148 | 0.05 | |
| 149 | 0.062 | |
| 150 | 0.025 | |
| 151 | 0.0275 | |
| 152 | 0.18 | |
| 153 | 0.026 | |
| 154 | 0.0033 | |
| 155 | 0.0135 | |
| 156 | 0.0205 | |
| 157 | 0.01175 | |
| 158 | 0.021 | |
| 159 | 0.0062 | |
| 160 | 0.018 | |
| 161 | 0.08 | |
| 162 | 0.0089 | |
| 163 | 0.01155 | |
| 164 | 0.00725 | |
| 165 | 0.011 | |
| 166 | 0.01115 | |
| 167 | 0.014 | |
| 168 | 0.13 | |

The invention claimed is:

1. A compound of the formula I,

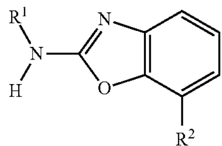

(I)

wherein:

$R^1$ is phenyl, (3,4,5-)trimethoxyphenyl, (3,4- or 3,5-) dimethoxyphenyl, (4-)morpholinophenyl, (4-)N-(2-methoxyethyl)-carbamoylphenyl, or (4-)N,N-(2-dimethylamino-ethyl)-carbamoylphenyl, (4-) dimethylaminocarbonyl-(3-)methyl-phenyl, (4-)-(2-methoxy-ethyl-piperazin-(-1-)yl-(3-)-methyl-phenyl, (4-)pyrrolidin-1-carbonyl-(3-)methyl-phenyl, (3-)methyl-(4-)-4-methylpiperazin-1-carbonyl-phenyl, (3- or 4-)4-methyl-piperazin-1-yl-phenyl, (4-)-4-ethyl-piperazin-1-yl-(3-)methyl-phenyl, (4-)-4-methyl-piperazin-1-yl-(-3-)cyano-phenyl, (4-)-piperazin-1-yl-phenyl, (4-)-4-cyclopropyl-piperazin-1-yl-phenyl, (4-)-4-(2-dimethylaminoethyl)-piperazin-1-yl-(3-)methyl-phenyl, (4-)4-isopropyl-piperazin-1-yl)-(-3-)methyl-phenyl, (4-)N,N-diethylaminocarbonyl-(3-)methyl-phenyl, (4-)-4-ethylpiperazin-1-carbonyl-(3-)methyl-phenyl, (4-)-(4-ethylpiperazin-1-ylmethyl)-(3-)methyl-phenyl, (4-)N-methylaminocarbonyl-(3-)methylphenyl, (4-)-4-(3,3,3-trifluoropropyl)-piperazin-1-yl-(3-)methyl-phenyl, (4-)-4-(2-(N',N'-dimethylamino)ethyl-aminocarbonyl-(3-)methyl-phenyl, (4-)-methanesulfonyl-phenyl, (4-)[(2-)-oxo-pyrrolidin-1-yl]-phenyl, (4-)N,N-diethylaminocarbonyl-(3-)methoxy phenyl, (3-)-4-methylpiperazin-1-yl-(4-)methyl-phenyl, (3-)-4-methylpiperazin-1-yl-(4-)methoxy-phenyl, (3- or 4-)-morpholinomethyl-(4- or 3-)methyl-phenyl, (2-)acetylamino-indan-(5-)yl, (2-)oxo-2,3-dihydroindol-(5-)yl, (4-)methylsulfinylphenyl, (4-)methoxyphenyl, (4-)methyl-(3-)methoxyphenyl, (4-)-N-(2-methoxyethyl)-aminocarbonyl-phenyl, (4-)N,N-dimethylcarbamoyl-phenyl, (3-) methanesulfonylamino-phenyl, (4-)methoxycarbonyl-(-3-)methoxy-phenyl, (4-)N,N-dimethylcarbamoyl-(-3-)methoxy-phenyl, (4-)-(4-cyclopropyl-piperazin-1-yl)-(-3-)methyl-phenyl, (4-)-N-(2-(N',N'-dimethylaminoethyl)-N-methyl-carbamoyl-(3-) methyl-phenyl, 1,3-dimethyl-oxo-1H-pyridine-5-yl, (3- or 4-)morpholino-(-4- or 3-)methyl-phenyl, (4-)morpholinomethyl-(3-)methyl-phenyl, (4-)morpholin-1-carbonyl-(3-)methyl-phenyl, (4-)-N-2-(methoxyethyl) aminocarbonyl-(3-)methyl-phenyl, (4-)-N-(3-N',N'-dimethylaminopropyl)amino-carbonyl-(3-)methyl-phenyl, (5-)-methyl-(6-)methoxy-pyridin-3-yl, (4-) dimethylcarbamoyl-(3,5-)dimethyl-phenyl, (4-) dimethylcarbamoyl-(-3-)ethyl-phenyl, (4-(4-)N,N-dimethylcarbamoyl-(-3-)methyl-phenyl or (4-) morpholino-(-3-)cyano-phenyl;

$R^2$ is phenyl, (4-)methylphenyl, (3-)methylphenyl, (2-)methylphenyl, (4-)-hydroxymethyl-phenyl, (4-)aminomethyl-phenyl, (3-)aminomethyl-phenyl, (4-)acetylaminomethyl-phenyl, (4-)methanesulfonylaminomethyl-phenyl, (3-)acetylaminomethyl-phenyl, (3-)methanesulfonylaminomethyl-phenyl, (4-) methanesulfonylaminomethyl-phenyl, (4-)(N-methylcarbamoyl)-methylphenyl, (4-) methanesulfinylmethylphenyl, (4-) methanesulfonylmethylphenyl, (3-)chlorophenyl, (3-) hydroxyphenyl, (4-)methoxyphenyl, (3-) methoxyphenyl, (2-)methoxyphenyl, (4-)aminophenyl, (3-)aminophenyl, (2-)aminophenyl, (3-)N-methylamino-phenyl, (4-)N,N-dimethylamino-phenyl, (4-) acetylamino-phenyl, (3-)acetylamino-phenyl, (4-)methanesulfonylamino-phenyl, (4-)methanesulfonylamino-phenyl, (3-) methanesulfonylamino-phenyl, (4-) carbamoylphenyl, (3-)carbamoylphenyl, (4-)(N-methyl-carbamoyl)-phenyl, (4-)(N,N-dimethyl-carbamoyl)-phenyl, (4-)methanesulfonylphenyl, (3-) methanesulfonylphenyl, (4-)sulfamoylphenyl, (4-)(N-methylsulfamoyl)-phenyl, (4-)[N,N-(dimethyl)-sulfamoyl]-phenyl, (4-)morpholinosulfonylphenyl, (4-) cyano-phenyl, (3-)cyanophenyl, (3-)nitrophenyl, (3-) amino-4-methyl-phenyl, (3-)amino-4-methoxyphenyl, (3-)amino-4-chlorophenyl, (4-)methoxy-3-nitrophenyl, (4-)morpholin-4-ylmethyl-phenyl, (3-)methyl-(4-)morpholin-4-ylmethyl-phenyl, (3-)fluoro-(4-)morpholin-4-ylmethyl-phenyl, (4-)S,S-dioxo-thiomorpholin-4-ylmethylphenyl, (3,5-)difluoro-(-4-)morpholin-4-ylmethyl-phenyl, (3-)fluoro-(4-)S,S-dioxothiomorpholin-4-ylmethyl-phenyl, (3,5-)difluoro-(4-)S,S-dioxothiomorpholin-4-ylmethyl-phenyl, (3-) trifluoromethyl-(-4-)morpholin-4-ylmethyl-phenyl, (3,5-)difluoro-(4-)[(preferably 4-)acetyl-piperazin-1-yl]methyl-phenyl, (3,5-)difluoro-(4-)piperazin-1-yl] methyl-phenyl, (4-)[(4-)methyl-piperazin-1-yl]methyl-phenyl, (3,5-)difluoro-(4-)[(-3-)oxo-piperazin-1-yl] methyl-phenyl (3,5-)difluoro-(4-)[preferably 4-)methyl-(3-)oxo-piperazin-1-yl]methyl-phenyl, (4-) imidazol-1-ylmethyl-phenyl, (4-)-4-methylpiperazin-1-carbonyl-phenyl, (4-)morpholin-4-carbonyl-phenyl, (2- or 3-)fluoro-(4-)morpholin-4-carbonyl-phenyl, (3-)methyl-(4-)morpholin-4-carbonyl-phenyl, (3,5-)difluoro-(4-)morpholin-4-carbonyl-phenyl, (4-)S,S-dioxothiomorpholin-4-carbonyl-phenyl, (3-)-fluoro-(4-)S,S-dioxothiomorpholin-4-carbonyl-phenyl, (4-)morpholin-4-carbonylmethyl-phenyl, (3-)fluoro-(4-)morpholin-4-carbonylmethyl-phenyl, [(4-)morpholin-4-carbonyl-(1,1,dimethyl)-methyl]phenyl, (4-)S,S-dioxothiomorpholin-4-carbonylmethyl-phenyl, (3-)fluoro-(4-)S,S-dioxothiomorpholin-4-carbonylmethyl-phenyl, 2H-pyrazol-(-3-)yl, (5-)N-methylcarbamoyl-thiophenyl, (4-)pyridyl, (3-)pyridyl, (2-)pyridyl, (6-)methoxy-pyridin-(3-)yl, 1H-benzoimidazol-(5-)yl, quinolin-(6-)yl or isoquinolin-(-4-)yl;

or a pharmaceutically acceptable salt thereof.

2. The compound of claim 1, wherein $R^1$ is (3,4,5-)trimethoxyphenyl or is 4-morpholinophenyl, (3,4- or 3,5)-dimethoxyphenyl, (4-)N-(2-methoxy-ethyl)-carbamoylphenyl, or (4-)-N,N-(2-dimethylamino-ethyl)-carbamoylphenyl; and $R^2$ is phenyl, 4-methylphenyl, 3-methylphenyl, 2-methylphenyl, 4-aminomethyl-phenyl, 3-aminomethyl-phenyl, 4-acetylaminomethyl-phenyl, 4-methanesulfonylaminomethyl-phenyl, 3-acetylaminomethyl-phenyl, 3-methanesulfonylaminomethyl-phenyl, 4-methanesulfonyl-aminomethyl-phenyl, 4-(N-methylcarbamoyl)methyl-phenyl, 4-methanesulfinylmethylphenyl, 4-methanesulfonylmethyl-phenyl, 3-chlorophenyl, 3-hydroxyphenyl, 4-methoxyphenyl, 3-methoxyphenyl, 2-methoxyphenyl, 4-aminophenyl, 3-aminophenyl, 2-aminophenyl, 3-N-methylamino-phenyl, 4-N,N-dimethylamino-phenyl, 4-acetylamino-phenyl, 3-acetylamino-phenyl, 4-methanesulfonylamino-phenyl, 4-methanesulfonylamino-phenyl, 3-methanesulfonylamino-phenyl, 4-carbamoylphenyl, 3-carbamoylphenyl, 4-(N-methyl-carbamoyl)-phenyl, 4-(N,N-dimethyl-carbamoyl)-phenyl, 4-methanesulfonylphenyl, 3-methanesulfonylphenyl, 4-sulfamoylphenyl, 4-(N-methylsulfamoyl)-phenyl, 4-[N,N-(dimethyl)-sulfamoyl]-phenyl, 4-morpholinosulfonylphenyl, 4-cyanophenyl, 3-cyanophenyl, 3-nitrophenyl, 3-amino-4-methyl-phenyl, 3-amino-4-methoxyphenyl, 3-amino-4-chlororphenyl, 4-methoxy-3-nitrophenyl, 2H-pyrazol-3-yl, 5-N-methylcarbamoyl-thiophenyl, 4-pyridyl, 3-pyridyl, 2-pyridyl, 6-methoxy-pyridin-3-yl, 1H-benzoimidazol-5-yl, quinolin-6-yl, or isoquinolin-4-yl;

or a pharmaceutically acceptable salt thereof.

3. A compound selected from the group consisting of:

(7-m-tolyl-benzooxazol-2-yl)-(3,4,5-trimethoxy-phenyl)-amine;

(7-phenyl-benzooxazol-2-yl)-(3,4,5-trimethoxy-phenyl)-amine;

(7-pyridin-3-yl-benzooxazol-2-yl)-(3,4,5-trimethoxy-phenyl)-amine;

[7-(3-methoxy-phenyl)-benzooxazol-2-yl]-(3,4,5-trimethoxy-phenyl)-amine;

[7-(2-methoxy-phenyl)-benzooxazol-2-yl]-(3,4,5-trimethoxy-phenyl)-amine;

[7-(3-hydroxy-phenyl)-benzooxazol-2-yl]-(3,4,5-trimethoxy-phenyl)-amine;

[7-(4-methoxy-phenyl)-benzooxazol-2-yl]-(3,4,5-trimethoxy-phenyl)-amine;

(7-isoquinolin-4-yl-benzooxazol-2-yl)-(3,4,5-trimethoxy-phenyl)-amine;

[7-(3-chloro-phenyl)-benzooxazol-2-yl]-(3,4,5-trimethoxy-phenyl)-amine;

[7-(3-amino-phenyl)-benzooxazol-2-yl]-(3,4,5-trimethoxy-phenyl)-amine;

[7-(4-amino-phenyl)-benzooxazol-2-yl]-(3,4,5-trimethoxy-phenyl)-amine;

[7-(6-methoxy-pyridin-3-yl)-benzooxazol-2-yl]-(3,4,5-trimethoxy-phenyl)-amine;

[7-(3-amino-4-methyl-phenyl)-benzooxazol-2-yl]-(3,4,5-trimethoxy-phenyl)-amine;

[7-(2-amino-phenyl)-benzooxazol-2-yl]-(3,4,5-trimethoxy-phenyl)-amine;

(7-quinolin-6-yl-benzooxazol-2-yl)-(3,4,5-trimethoxy-phenyl)-amine;

4-[2-(3,4,5-trimethoxy-phenylamino)-benzooxazol-7-yl]-benzamide;

7-(4-methanesulfonyl-phenyl)-benzooxazol-2-yl]-(3,4,5-trimethoxy-phenyl)-amine;

4-[2-(3,4,5-trimethoxy-phenylamino)-benzooxazol-7-yl]-benzenesulfonamide;

4-[2-(3,4,5-trimethoxy-phenylamino)-benzooxazol-7-yl]-benzonitrile;

[7-(2H-pyrazol-3-yl)-benzooxazol-2-yl]-(3,4,5-trimethoxy-phenyl)-amine;

N-methyl-4-[2-(3,4,5-trimethoxy-phenylamino)-benzooxazol-7-yl]-benzenesulfonamide;

N,N-dimethyl-4-[2-(3,4,5-trimethoxy-phenylamino)-benzooxazol-7-yl]-benzenesulfonamide;

{7-[4-(morpholine-4-sulfonyl)-phenyl]-benzooxazol-2-yl}-(3,4,5-trimethoxy-phenyl)-amine;

N-methyl-4-[2-(3,4,5-trimethoxy-phenylamino)-benzooxazol-7-yl]-benzamide;

N,N-dimethyl-4-[2-(3,4,5-trimethoxy-phenylamino)-benzooxazol-7-yl]-benzamide;

N-{4-[2-(3,4,5-trimethoxy-phenylamino)-benzooxazol-7-yl]-phenyl}-methanesulfonamide;

N-{4-[2-(3,4,5-trimethoxy-phenylamino)-benzooxazol-7-yl]-phenyl}-acetamide;

N-{3-[2-(3,4,5-trimethoxy-phenylamino)-benzooxazol-7-yl]-phenyl}-acetamide;

[7-(4-aminomethyl-phenyl)-benzooxazol-2-yl]-(3,4,5-trimethoxy-phenyl)-amine;

N-{4-[2-(3,4,5-trimethoxy-phenylamino)-benzooxazol-7-yl]-benzyl}-acetamide;

N-{4-[2-(3,4,5-trimethoxy-phenylamino)-benzooxazol-7-yl]-benzyl}-methanesulfonamide;

[7-(3-aminomethyl-phenyl)-benzooxazol-2-yl]-(3,4,5-trimethoxy-phenyl)-amine;

N-{3-[2-(3,4,5-trimethoxy-phenylamino)-benzooxazol-7-yl]-benzyl}-acetamide;

2-(3,4,5-trimethoxy-phenylamino)-benzooxazol-7-yl]-thiophene-2-carboxylic acid methylamide;

[7-(1H-benzoimidazol-5-yl)-benzooxazol-2-yl]-(3,4,5-trimethoxy-phenyl)-amine;

[4-(4-amino-phenyl)-oxazolo[5,4-c]pyridin-2-yl]-(3,4,5-trimethoxy-phenyl)-amine;

[4-(3-amino-phenyl)-oxazolo[5,4-c]pyridin-2-yl]-(3,4,5-trimethoxy-phenyl)-amine;

4-[2-(3,4,5-trimethoxy-phenylamino)-oxazolo[5,4-c]pyridin-4-yl]-benzenesulfonamide;

[7-(3-methoxy-phenyl)-benzooxazol-2-yl]-(4-morpholin-4-yl-phenyl)-amine;

[7-(4-amino-phenyl)-benzooxazol-2-yl]-(4-morpholin-4-yl-phenyl)-amine;

N-{4-[2-(4-morpholin-4-yl-phenylamino)-benzooxazol-7-yl-phenyl}-methane-sulfonamide;

[7-(3-amino-phenyl)-benzooxazol-2-yl]-(6-morpholin-4-yl-pyridin-3-yl)-amine;

N-(2-methoxy-ethyl)-4-[7-(4-sulfamoyl-phenyl)-benzooxazol-2-ylamino]-benzamide;

N-(2-dimethylamino-ethyl)-4-[7-(4-sulfamoyl-phenyl)-benzooxazol-2-ylamino]-benzamide;

4-[2-(3,4-dimethoxy-phenylamino)-benzooxazol-7-yl]-benzenesulfonamide;

4-[2-(3,4-dimethoxy-phenylamino)-benzooxazol-7-yl]-N-methyl-benzenesulfonamide;

4-[2-(3,5-dimethoxy-phenylamino)-benzooxazol-7-yl]-benzenesulfonamide;

N-methyl-2-{4-[2-(3,4,5-trimethoxy-phenylamino)-benzooxazol-7-yl]-phenyl}-acetamide;

N-{4-[2-(3,4,5-trimethoxy-phenylamino)-benzooxazol-7-yl]-benzyl}-methanesulfonamide;

[7-(4-methanesulfinylmethyl-phenyl)-benzooxazol-2-yl]-(3,4,5-trimethoxy-phenyl)-amine;

(7-o-Tolyl-benzooxazol-2-yl)-(3,4,5-trimethoxy-phenyl)-amine;

3-[2-(3,4,5-Trimethoxy-phenylamino)-benzooxazol-7-yl]-benzonitrile;

(7-Pyridin-2-yl-benzooxazol-2-yl)-(3,4,5-trimethoxy-phenyl)-amine;

3-[2-(3,4,5-Trimethoxy-phenylamino)-benzooxazol-7-yl]-benzamide;

[7-(3-Nitro-phenyl)-benzooxazol-2-yl]-(3,4,5-trimethoxy-phenyl)-amine;

[7-(3-Methanesulfonyl-phenyl)-benzooxazol-2-yl]-(3,4,5-trimethoxy-phenyl)-amine;

N-Methyl-3-[2-(3,4,5-trimethoxy-phenylamino)-benzooxazol-7-yl]-benzenesulfonamide;

[7-(4-Methoxy-3-nitro-phenyl)-benzooxazol-2-yl]-(3,4,5-trimethoxy-phenyl)-amine;

[7-(3-Amino-4-chloro-phenyl)-benzooxazol-2-yl]-(3,4,5-trimethoxy-phenyl)-amine;

[7-(3-Amino-4-methoxy-phenyl)-benzooxazol-2-yl]-(3,4,5-trimethoxy-phenyl)-amine;

[7-(4-Dimethylamino-phenyl)-benzooxazol-2-yl]-(3,4,5-trimethoxy-phenyl)-amine; and N-{3-[2-(3,4,5-Trimethoxy-phenylamino)-benzooxazol-7-yl]-phenyl}-methanesulfonamide;

or a pharmaceutically acceptable salt thereof.

4. A compound selected from the group consisting of:

[7-(3-amino-phenyl)-benzooxazol-2-yl]-(4-morpholin-4-yl-phenyl)-amine;

4-[7-(3-fluoro-4-morpholin-4-ylmethyl-phenyl)-benzooxazol-2-ylamino]-2,N,N-trimethyl-benzamide;

4-{7-[4-(1,1-dioxo-thiomorpholin-4-ylmethyl)-3,5-difluoro-phenyl]-benzooxazol-2-ylamino}-2,N,N-trimethyl-benzamide;

[4-(2-{4-[4-(2-methoxy-ethyl)-piperazin-1-yl]-3-methyl-phenylamino}-benzooxazol-7-yl)-2-methyl-phenyl]-morpholin-4-yl-methanone;

{4-[7-(3-fluoro-4-morpholin-4-ylmethyl-phenyl)-benzooxazol-2-ylamino]-2-methyl-phenyl}-pyrrolidin-1-yl-methanone;

4-[7-(3,5-Difluoro-4-morpholin-4-ylmethyl-phenyl)-benzooxazol-2-ylamino]-2,N,N-trimethyl-benzamide;

2,N,N-trimethyl-4-{7-[4-(morpholine-4-carbonyl)-phenyl]-benzooxazol-2-ylamino}-benzamide;

2,N,N-trimethyl-4-{7-[4-(2-morpholin-4-yl-2-oxo-ethyl)-phenyl]-benzooxazol-2-ylamino}-benzamide;

4-[7-(4-methanesulfonylmethyl-phenyl)-benzooxazol-2-ylamino]-N,N-dimethyl-benzamide;

2-(4-{2-[3-methyl-4-(4-methyl-piperazine-1-carbonyl)-phenylamino]-benzooxazol-7-yl}-phenyl)-1-morpholin-4-yl-ethanone;

2-(2-fluoro-4-{2-[3-methyl-4-(4-methyl-piperazine-1-carbonyl)-phenylamino]benzooxazol-7-yl}-phenyl)-1-morpholin-4-yl-ethanone;

2-(4-{2-[4-(4-methyl-piperazin-1-yl)-phenylamino]-benzooxazol-7-yl}-phenyl)-1-morpholin-4-yl-ethanone;

(2-fluoro-4-{2-[4-(4-methyl-piperazin-1-yl)-phenylamino]-benzooxazol-7-yl}-phenyl)-morpholin-4-yl-methanone;

4-{7-[2-fluoro-4-(morpholine-4-carbonyl)-phenyl]-benzooxazol-2-ylamino}-2,N,N-trimethyl-benzamide;

4-(7-{4-[2-(1,1-dioxo-thiomorpholin-4-yl)-2-oxo-ethyl]-phenyl}-benzooxazol-2-ylamino)-2,N,N-trimethyl-benzamide;

4-{7-[3-fluoro-4-(morpholine-4-carbonyl)-phenyl]benzooxazol-2-ylamino}-2,N,N-trimethyl-benzamide;

4-{7-[4-(1,1-dioxo-thiomorpholin-4-ylmethyl)-phenyl]-benzooxazol-2-ylamino}-2,N,N-trimethyl-benzamide;

(1,1-dioxo-thiomorpholin-4-yl)-(2-fluoro-4-{2-[4-(4-methyl-piperazin-1-yl)-phenylamino]-benzooxazol-7-yl}-phenyl)-methanone;

4-[7-(4-methanesulfinylmethyl-phenyl)-benzooxazol-2-ylamino]-2,N,N-trimethyl-benzamide;

(2-methyl-4-{2-[4-(4-methyl-piperazin-1-yl)-phenylamino]-benzooxazol-7-yl}-phenyl)-morpholin-4-yl-methanone;

4-(7-{4-[2-(1,1-dioxo-thiomorpholin-4-yl)-2-oxo-ethyl]-3-fluoro-phenyl}-benzooxazol-2-ylamino)-2,N,N-trimethyl-benzamide;

4-{7-[4-(1,1-dioxo-thiomorpholin-4-ylmethyl)-3-fluoro-phenyl]-benzooxazol-2-ylamino}-2,N,N-trimethyl-benzamide;

2,N,N-trimethyl-4-{7-[3-methyl-4-(morpholine-4-carbonyl)-phenyl]-benzooxazol-2-ylamino}-benzamide;

2,N,N-trimethyl-4-[7-(4-morpholin-4-ylmethyl-3-trifluoromethyl-phenyl)-benzooxazol-2-ylamino]-benzamide;

[4-(4-ethyl-piperazin-1-yl)-3-methyl-phenyl]-[7-(3-fluoro-4-morpholin-4-ylmethyl-phenyl)-benzooxazol-2-yl]-amine;

{7-[4-(1,1-dioxo-thiomorpholin-4-ylmethyl)-3-fluoro-phenyl]-benzooxazol-2-yl}-[4-(4-ethyl-piperazin-1-yl)-3-methyl-phenyl]-amine;

{7-[4-(1,1-dioxo-thiomorpholin-4-ylmethyl)-phenyl]-benzooxazol-2-yl}-[4-(4-methyl-piperazin-1-yl)-phenyl]-amine;

5-{7-[3-fluoro-4-(morpholine-4-caronyl)-phenyl]-benzooxazol-2-ylamino}-2-(4-methyl-piperazin-1-yl)-benzonitrile;

{2-fluoro-4-[2-(4-piperazin-1-yl-phenylamino)-benzooxazol-7-yl]-phenyl}-morpholin-4-yl-methanone;

[4-(4-ethyl-piperazin-1-yl)-3-methyl-phenyl]-[7-(4-methanesulfonyl-phenyl)-benzooxazol-2-yl]-amine;

4-{2-[4-(4-methyl-piperazin-1-yl)-phenylamino]-benzooxazol-7-yl}-benzenesulfonamide;

(4-{2-[4-(4-ethyl-piperazin-1-yl)-3-methyl-phenylamino]-benzooxazol-7-yl}-2-fluoro-phenyl)-morpholin-4-yl-methanone;

{7-[4-(1,1-dioxo-thiomorpholin-4-ylmethyl)-3,5-difluoro-phenyl]-benzooxazol-2-yl}-[4-(4-methyl-piperazin-1-yl)-phenyl]-amine;

(4-{7-[4-(1,1-dioxo-thiomorpholin-4-ylmethyl)-3,5-difluoro-phenyl]-benzooxazol-2-ylamino}-2-methyl-phenyl)-pyrrolidin-1-yl-methanone;

(4-{2-[4-(4-cyclopropyl-piperazin-1-yl)-phenylamino]-benzooxazol-7-yl}-2-methyl-phenyl)-morpholin-4-yl-methanone;

[7-(3,5-difluoro-4-morpholin-4-ylmethyl-phenyl)-benzooxazol-2-yl]-[4-(4-ethyl-piperazin-1-yl)-3-methyl-phenyl]amine;

{4-[7-(3,5-difluoro-4-morpholin-4-ylmethyl-phenyl)-benzooxazol-2-ylamino]-2-methyl-phenyl}-pyrrolidin-1-yl-methanone;

{4-[4-(2-dimethylamino-ethyl)-piperazin-1-yl]-3-methyl-phenyl}-[7-(4-methanesulfonyl-phenyl)-benzooxazol-2-yl]-amine;

{7-[4-(1,1-dioxo-thiomorpholin-4-ylmethyl)-3,5-difluoro-phenyl]-benzooxazol-2-yl}-[4-(4-isopropyl-piperazin-1-yl)-3-methyl-phenyl]-amine;

[4-(2-{4-[4-(2-dimethylamino-ethyl)-piperazin-1-yl]-3-methyl-phenylamino}-benzooxazol-7-yl)-2-methyl-phenyl]-morpholin-4-yl-methanone;

4-[7-(3,5-difluoro-4-morpholin-4-ylmethyl-phenyl)-benzooxazol-2-ylamino]-N,N-diethyl-2-methyl-benzamide;

{4-[7-(3,5-difluoro-4-morpholin-4-ylmethyl-phenyl)-benzooxazol-2-ylamino]-2-methyl-phenyl}-(4-ethyl-piperazin-1-yl)-methanone;

[4-(4-isopropyl-piperazin-1-yl)-3-methyl-phenyl]-[7-(4-methanesulfonyl-phenyl)-benzooxazol-2-yl]-amine;

(4-{2-[4-(4-isopropyl-piperazin-1-yl)-3-methyl-phenylamino]-benzooxazol-7-yl}-2-methyl-phenyl)-morpholin-4-yl-methanone;

{4-[4-(2-dimethylamino-ethyl)-piperazin-1-yl]-3-methyl-phenyl}-{7-[4-(1,1-dioxothiomorpholin-4-ylmethyl)-3,5-difluoro-phenyl]-benzooxazol-2-yl}-amine;

{7-[4(-1,1-dioxo-thiomorpholin-4-ylmethyl)-3,5-difluoro-phenyl]-benzooxazol-2-yl}-{4-[4-(2-methoxy-ethyl)-piperazin-1-yl]-3-methyl-phenyl}-amine;

(4-{2-[4-(4-ethyl-piperazin-1-yl)-3-methyl-phenylamino]-benzooxazol-7-yl}-2,6-difluorophenyl)-morpholin-4-yl-methanone;

{2-methyl-4-[7-(3-methyl-4-morpholin-4-ylmethyl-phenyl)-benzooxazol-2-ylamino]-phenyl}-pyrrolidin-1-yl-methanone;

2-(4-{2-[4-(4-ethyl-piperazin-1-yl)-3-methyl-phenylamino]-benzooxazol-7-yl}-phenyl)-2-methyl-1-morpholin-4-yl-propan-1-one;

4-{2-[4-(4-ethyl-piperazin-1-yl)-3-methyl-phenylamino]-benzooxazol-7-yl}-benzenesulfonamide;

[4-(4-cyclopropyl-piperazin-1-yl)-phenyl]-[7-(4-methanesulfonyl-phenyl)-benzooxazol-2-yl]-amine;

[4-(4-cyclopropyl-piperazin-1-yl)-phenyl]-{7-[4-(1,1-dioxo-thiomorpholin-4-ylmethyl)-3,5-difluoro-phenyl]-benzooxazol-2-yl}-amine;

[7-(4-methanesulfonyl-phenyl)-benzooxazol-2-yl]-{4-[4-(2-methoxy-ethyl)-piperazin-1-yl]-3-methyl-phenyl}-amine;

(1,1-dioxo-thiomorpholin-4-yl)-(4-{2-[4-(4-ethyl-piperazin-1-yl)-3-methyl-phenylamino]-benzooxazol-7-yl}-phenyl)-methanone;

4-{7-[4-(4-acetyl-piperazin-1-ylmethyl)-3,5-difluoro-phenyl]-benzooxazol-2-ylamino}-N,N-diethyl-2-methyl-benzamide;

4-[7-(3,5-difluoro-4-piperazin-1-ylmethyl-phenyl)-benzooxazol-2-ylamino]-N,N-diethyl-2-methyl-benzamide;

(4-{2-[4-(4-ethyl-piperazin-1-ylmethyl)-3-methyl-phenylamino]-benzooxazol-7-yl}-2-fluoro-phenyl)-morpholin-4-yl-methanone;

4-[7-(3,5-difluoro-4-morpholin-4-ylmethyl-phenyl)-benzooxazol-2-ylamino]-2,N-dimethyl-benzamide;

[7-(3,5-difluoro-4-morpholin-4-ylmethyl-phenyl)-benzooxazol-2-yl]-{3-methyl-4-[4-(3,3,3-trifluoro-propyl)-piperazin-1-yl]-phenyl}-amine;

4-[7-(3,5-difluoro-4-morpholin-4-ylmethyl-phenyl)-benzooxazol-2-ylamino]-N-(2-dimethylamino-ethyl)-2-methyl-benzamide;

4-(7-{4-[2-(1,1-dioxo-thiomorpholin-4-yl)-2-oxo-ethyl]-phenyl}-benzooxazol-2-ylamino)-N,N-diethyl-2-methoxy-benzamide;

2-{4-[2-(4-methanesulfonyl-phenylamino)-benzooxazol-7-yl]-phenyl}-1-morpholin-4-yl-ethanone;

1-(4-{7-[4-(1,1-dioxo-thiomorpholin-4-ylmethyl)-3,5-difluoro-phenyl]-benzooxazol-2-ylamino}-phenyl)-pyrrolidin-2-one;

1-{4-[7-(3,5-difluoro-4-morpholin-4-ylmethyl-phenyl)-benzooxazol-2-ylamino]-phenyl}-pyrrolidin-2-one;

(4-{2-[4-methoxy-3-(4-methyl-piperazin-1-yl)-phenylamino]-benzooxazol-7-yl}-2-methyl-phenyl)-morpholin-4-yl-methanone;

{7-[4-(1,1-dioxo-thiomorpholin-4-ylmethyl)-3,5-difluoro-phenyl]-benzooxazol-2-yl}-[3-(4-methyl-piperazin-1-yl)-phenyl]-amine;

(2-methyl-4-{2-[3-(4-methyl-piperazin-1-yl)-phenylamino]-benzooxazol-7-yl}-phenyl)-morpholin-4-yl-methanone;

{7-[4-(1,1-dioxo-thiomorpholin-4-ylmethyl)-3,5-difluoro-phenyl]-benzooxazol-2-yl}-[4-methoxy-3-(4-methyl-piperazin-1-yl)-phenyl]-amine;

{2-fluoro-4-[2-(3-methyl-4-morpholin-4-ylmethyl-phenylamino)-benzooxazol-7-yl]-phenyl}-morpholin-4-yl-methanone;

N-{-[7-(3-fluoro-4-morpholin-4-ylmethyl-phenyl)-benzooxazol-2-ylamino]-indan-2-yl}-acetamide;

N-(5-{7-[4-(1,1-dioxo-thiomorpholin-4-ylmethyl)-phenyl]-benzooxazol-2-ylamino}-indan-2-yl)-acetamide;

5-[7-(3,5-difluoro-4-morpholin-4-ylmethyl-phenyl)-benzooxazol-2-ylamino]-1,3-dihydro-indol-2-one;

2-{4-[2-(4-methanesulfinyl-phenylamino)-benzooxazol-7-yl]-phenyl}-1-morpholin-4-yl-ethanone;

[7-(4-imidazol-1-ylmethyl-phenyl)-benzooxazol-2-yl]-(3,4,5-trimethoxy-phenyl)-amine;

{7-[4-(4-methyl-piperazin-1-ylmethyl)-phenyl]-benzooxazol-2-yl}-(3,4,5-trimethoxy-phenyl)-amine;

[7-(4-morpholin-4-ylmethyl-phenyl)-benzooxazol-2-yl]-(3,4,5-trimethoxy-phenyl)-amine;

4-[2-(4-methoxy-phenylamino)-benzooxazol-7-yl]-N-methyl-benzenesulfonamide;

1-morpholin-4-yl-2-{4-[2-(3,4,5-trimethoxy-phenylamino)-benzooxazol-7-yl]-phenyl}-ethanone;

morpholin-4-yl-{4-[2-(3,4,5-trimethoxy-phenylamino)-benzooxazol-7-yl]-phenyl}-methanone;

(4-methyl-piperazin-1-yl)-{4-[2-(3,4,5-trimethoxy-phenylamino)-benzooxazol-7-yl]-phenyl}-methanone;

{4-[2-(3,4,5-trimethoxy-phenylamino)-benzooxazol-7-yl]-phenyl}-methanol;

4-[2-(3-methoxy-4-methyl-phenylamino)-benzooxazol-7-yl]-N-methyl-benzenesulfonamide;

N-(2-methoxy-ethyl)-4-{7-[4-(morpholine-4-carbonyl)-phenyl]benzooxazol-2-ylamino}-benzamide;

N,N-dimethyl-4-[7-(4-sulfamoyl-phenyl)-benzooxazol-2-ylamino]-benzamide;

N-(2-methoxy-ethyl)-4-{7-[4-(2-morpholin-4-yl-2-oxo-ethyl)-phenyl]-benzooxazol-2-ylamino}-benzamide;

N-(3-{7-[4-(morpholine-4-carbonyl)-phenyl]-benzooxazol-2-ylamino}-phenyl)-methane sulfonamide;

2-methoxy-4-{7-[4-(morpholine-4-carbonyl)-phenyl]-benzooxazol-2-ylamino}-benzoic acid methyl ester;

2-methoxy-N,N-dimethyl-4-{7-[4-(morpholine-4-carbonyl)-phenyl]-benzooxazol-2-ylamino}-benzamide;

2-methyl-2-(4-{2-[4-(4-methyl-piperazin-1-yl)-phenylamino]-benzooxazol-7-yl}-phenyl)-1-morpholin-4-yl-propan-1-one;

{4-[4-(1,1-dioxo-thiomorpholin-4-ylmethyl)-3,5-difluoro-phenyl]-oxazolo[5,4-c]pyridin-2-yl}-[4-(4-ethyl-piperazin-1-yl)-3-methyl-phenyl]-amine;

[4-(4-cyclopropyl-piperazin-1-yl)-3-methyl-phenyl]-{7-[4-(1,1-dioxo-thiomorpholin-4-ylmethyl)-3,5-difluoro-phenyl]-benzooxazol-2-yl}-amine;

(4-{2-[4-(4-cyclopropyl-piperazin-1-yl)-3-methyl-phenylamino]-benzooxazol-7-yl}-2-methyl-phenyl)-morpholin-4-yl-methanone;

(4-{2-[4-(4-cyclopropyl-piperazin-1-yl)-3-methyl-phenylamino]-benzooxazol-7-yl}-2-fluoro-phenyl)-morpholin-4-yl-methanone;

2-(4-{2-[4-(4-cyclopropyl-piperazin-1-yl)-3-methyl-phenylamino]-benzooxazol-7-yl}-phenyl)-2-methyl-1-morpholin-4-yl-propan-1-one;

4-[7-(3,5-difluoro-4-morpholin-4-ylmethyl-phenyl)-benzooxazol-2-ylamino]-N-(2-dimethylamino-ethyl)-2,N-dimethyl-benzamide;

N-(2-dimethylamino-ethyl)-4-{7-[4(1,1-dioxo-thiomorpholin-4-ylmethyl)-3,5-difluoro-phenyl]-benzooxazol-2-ylamino}-2,N-dimethyl-benzamide;

[4-(4-cyclopropyl-piperazin-1-yl)-3-methyl-phenyl]-[7-(3,5-difluoro-4-morpholin-4-ylmethyl-phenyl)-benzooxazol-2-yl]-amine;

5-[7-(3,5-difluoro-4-morpholin-4-ylmethyl-phenyl)-benzooxazol-2-ylamino]-1,3-dimethyl-1H-pyridin-2-one;

(4-{2-[4-(4-cyclopropyl-piperazin-1-yl)-3-methyl-phenylamino]-benzooxazol-7-yl}-2-methyl-phenyl)-(1,1-dioxo-thiomorpholin-4-yl)-methanone;

[7-(3,5-difluoro-4-morpholin-4-ylmethyl-phenyl)-benzooxazol-2-yl]-(3-methyl-4-morpholin-4-yl-phenyl)-amine;

{7-[4-(1,1-dioxo-thiomorpholin-4-ylmethyl)-3,5-difluoro-phenyl]-benzooxazol-2-yl}-(3-methyl-4-morpholin-4-yl-phenyl)-amine;

(1,1-dioxo-thiomorpholin-4-yl)-{-[2-(3-methyl-4-morpholin-4-ylmethyl-phenylamino)-benzooxazol-7-yl]-phenyl}-methanone;

{2-methyl-4-[2-(3-methyl-4-morpholin-4-ylmethyl-phenylamino)-benzooxazol-7-yl]-phenyl}-morpholin-4-yl-methanone;

2-methyl-2-{4-[2-(3-methyl-4-morpholin-4-ylmethyl-phenylamino)-benzooxazol-7-yl]-phenyl}-1-morpholin-4-yl-propan-1-one;

4-{7-[3,5-difluoro-4-(3-oxo-piperazin-1-ylmethyl)-phenyl]-benzooxazol-2-ylamino}-2,N,N-trimethyl-benzamide;

4-{2,6-difluoro-4-[2-(3-methyl-4-morpholin-4-yl-phenylamino)-benzooxazol-7-yl]-benzyl}-piperazin-2-one;

4-(4-{2-[4-(4-cyclopropyl-piperazin-1-yl)-3-methyl-phenylamino]-benzooxazol-7-yl}-2,6-difluoro-benzyl)-piperazin-2-one;

4-{7-[3,5-difluoro-4-(4-methyl-3-oxo-piperazin-1-ylmethyl)-phenyl]-benzooxazol-2-ylamino}-2,N,N-trimethyl-benzamide;

4-{2,6-difluoro-4-[2-(3-methyl-4-morpholin-4-yl-phenylamino)-benzooxazol-7-yl]-benzyl}-1-methyl-piperazin-2-one;

4-(4-{2-[4-(4-cyclopropyl-piperazin-1-yl)-3-methyl-phenylamino]-benzooxazol-7-yl}-2,6-difluoro-benzyl)-1-methyl-piperazin-2-one;

4-[7-(4-methanesulfinylmethyl-3-methyl-phenyl)-benzooxazol-2-ylamino]-2,N,N-trimethyl-benzamide;

[4-(4-cyclopropyl-piperazin-1-yl)-3-methyl-phenyl]-[7-(4-methanesulfonylmethyl-3-methyl-phenyl)-benzooxazol-2-yl]-amine;

[7-(4-methanesulfinylmethyl-3-methyl-phenyl)-benzooxazol-2-yl]-(4-methyl-3-morpholin-4-yl-phenyl)-amine;

{4-[7-(3,5-difluoro-4-morpholin-4-ylmethyl-phenyl)-benzooxazol-2-ylamino]-2-methyl-phenyl}-morpholin-4-yl-methanone;

4-[7-(3,5-difluoro-4-morpholin-4-ylmethyl-phenyl)-benzooxazol-2-ylamino]-N-(2-methoxy-ethyl)-2-methyl-benzamide;

4-[7-(3,5-difluoro-4-morpholin-4-ylmethyl-phenyl)-benzooxazol-2-ylamino]-N-(3-dimethylamino-propyl)-2-methyl-benzamide;

[7-(3,5-difluoro-4-morpholin-4-ylmethyl-phenyl)-benzooxazol-2-yl]-(6-methoxy-5-methyl-pyridin-3-yl)-amine;

4-[7-(3,5-difluoro-4-morpholin-4-ylmethyl-phenyl)-benzooxazol-2-ylamino]-2,6,N,N-tetramethyl-benzamide;

4-[7-(3,5-difluoro-4-morpholin-4-ylmethyl-phenyl)-benzooxazol-2-ylamino]-2-ethyl-N,N-dimethyl-benzamide;

4-[7-(3,5-difluoro-4-morpholin-4-ylmethyl-phenyl)-benzooxazol-2-ylamino]-N-(2-methoxy-ethyl)-2,N-dimethyl-benzamide; and 4-[7-(3,5-difluoro-4-morpholin-4-ylmethyl-phenyl)-benzooxazol-2-ylamino]-2-morpholin-4-yl-benzonitrile;

or a pharmaceutically acceptable salt thereof.

5. A pharmaceutical composition comprising a compound according to claim 1, or a pharmaceutically acceptable salt thereof, and a pharmaceutically acceptable carrier material.

6. A process for the manufacture of a compound of claim 1, comprising either a) reacting a compound of the formula II,

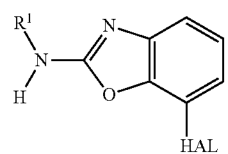

(II)

wherein $R^1$ is as defined in claim 1, and Hal is halo under Suzuki coupling conditions with a boronic acid of the formula III,

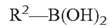

$R^2$—B(OH)$_2$ (III)

wherein $R^2$ is as defined in claim 1 or b) reacting a compound of the formula II,

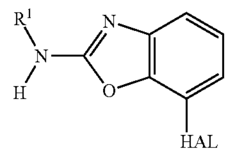

(II)

wherein $R^1$ is as defined in claim 1, and Hal is halo, under Stille coupling conditions with an organotin compound of the formula III*

$$R^2\text{—Sn(alk)}_3 \quad \text{(III*)}$$

wherein $R^2$ is as defined in claim 1, and alk is alkyl.

7. A method for the treatment of a JAK2 mediated disease in a warm-blooded animal, which comprises administering to the warm blooded animal an effective amount of a compound according to claim 1, or a pharmaceutically acceptable salt thereof, wherein the JAK2 mediated disease is a tumor disease, leukaemia, polycythemia vera, essential thrombocythemia, or myelofibrosis with myeloid metaplasia.

8. The method according to claim 7 wherein the JAK2 mediated disease is leukaemia.

9. The method according to claim 7 wherein the JAK2 mediated disease is polycythemia vera.

10. The method according to claim 7 wherein the JAK2 mediated disease is essential thrombocythemia.

11. The method according to claim 7 wherein the JAK2 mediated disease is myelofibrosis with myeloid metaplasia.

* * * * *